(12) United States Patent
Bohana-Kashtan et al.

(10) Patent No.: US 11,987,810 B2
(45) Date of Patent: May 21, 2024

(54) RPE CELL POPULATIONS AND METHODS OF GENERATING SAME

(71) Applicant: Cell Cure Neurosciences Ltd., Jerusalem (IL)

(72) Inventors: Osnat Bohana-Kashtan, Tel-Mond (IL); Lior Ann Rosenberg Belmaker, Shoham (IL); Ofer Wiser, Jerusalem (IL)

(73) Assignee: CELL CURE NEUROSCIENCES LTD., Jerusalem (IL)

( * ) Notice: Subject to any disclaimer, the term of this patent is extended or adjusted under 35 U.S.C. 154(b) by 0 days.

(21) Appl. No.: 17/546,013

(22) Filed: Dec. 8, 2021

(65) Prior Publication Data

US 2022/0154141 A1    May 19, 2022

Related U.S. Application Data

(62) Division of application No. 15/539,473, filed as application No. PCT/IL2015/051269 on Dec. 30, 2015, now Pat. No. 11,891,622.

(60) Provisional application No. 62/195,309, filed on Jul. 22, 2015, provisional application No. 62/116,972, filed on Feb. 17, 2015, provisional application No. 62/097,753, filed on Dec. 30, 2014.

(51) Int. Cl.
    *C12N 5/079*    (2010.01)
    *A61K 35/30*    (2015.01)

(52) U.S. Cl.
    CPC ............ *C12N 5/0621* (2013.01); *A61K 35/30* (2013.01); *C12N 2500/02* (2013.01); *C12N 2500/38* (2013.01); *C12N 2501/115* (2013.01); *C12N 2501/15* (2013.01); *C12N 2501/16* (2013.01); *C12N 2506/02* (2013.01); *C12N 2533/52* (2013.01)

(58) Field of Classification Search
    None
    See application file for complete search history.

(56) References Cited

U.S. PATENT DOCUMENTS

| | | |
|---|---|---|
| 3,791,932 A | 2/1974 | Schuurs et al. |
| 3,839,153 A | 10/1974 | Schuurs et al. |
| 3,850,578 A | 11/1974 | McConnell |
| 3,850,752 A | 11/1974 | Schuurs et al. |
| 3,853,987 A | 12/1974 | Dreyer |
| 3,867,517 A | 2/1975 | Ling |
| 3,879,262 A | 4/1975 | Schuurs et al. |
| 3,901,654 A | 8/1975 | Gross |
| 3,935,074 A | 1/1976 | Rubenstein et al. |
| 3,984,533 A | 10/1976 | Uzgiris |
| 3,996,345 A | 12/1976 | Ullman et al. |
| 4,034,074 A | 7/1977 | Miles |
| 4,098,876 A | 7/1978 | Piasio et al. |
| 4,666,828 A | 5/1987 | Gusella |
| 4,683,202 A | 7/1987 | Mullis |
| 4,801,531 A | 1/1989 | Frossard |
| 4,879,219 A | 11/1989 | Wands et al. |
| 5,011,771 A | 4/1991 | Bellet et al. |
| 5,192,659 A | 3/1993 | Simons |
| 5,272,057 A | 12/1993 | Smulson et al. |
| 5,281,521 A | 1/1994 | Trojanowski et al. |
| 5,405,742 A | 4/1995 | Taylor |
| 5,755,785 A | 5/1998 | Rowsey et al. |
| 5,843,780 A | 12/1998 | Thomson |
| 5,854,015 A | 12/1998 | Garnett et al. |
| 5,941,250 A | 8/1999 | Aramant et al. |
| 5,962,027 A | 10/1999 | Hughes |
| 6,045,791 A | 4/2000 | Liu |
| 6,090,622 A | 7/2000 | Gearhart et al. |
| 6,632,666 B2 | 10/2003 | Baust et al. |
| 6,921,633 B2 | 7/2005 | Baust et al. |
| 8,268,303 B2 | 9/2012 | Kilmanskaya et al. |
| 8,956,866 B2 | 2/2015 | Idelson et al. |
| 9,446,076 B2 | 9/2016 | Gaussin et al. |
| 11,066,642 B2 | 7/2021 | Bohana-kashtan et al. |
| 2009/0226955 A1 | 9/2009 | Elliot et al. |
| 2011/0027333 A1* | 2/2011 | Idelson .................. A61K 35/30 |
| | | 435/366 |
| 2011/0034422 A1 | 2/2011 | Kannan et al. |
| 2012/0171295 A1 | 7/2012 | Abramson |
| 2012/0258451 A1 | 10/2012 | Klimanskaya |

(Continued)

FOREIGN PATENT DOCUMENTS

| CN | 101724602 A | 6/2010 |
|---|---|---|
| CN | 102618497 A | 8/2012 |

(Continued)

OTHER PUBLICATIONS

Garita-Hernandez, M. et al. 2013. Hypoxia increases the yield of photoreceptors differentiating from mouse embryonic stem cells and improves the modeling of retinogenesis in vitro. Stem Cells 31: 966-978; specif. pp. 966, 967, 968, 971, 972, 973, 976.*

Amit, M. et al. 2004. Feeder layer- and serum-free culture of human embryonic stem cells. Biology of Reproduction 70: 837-845; specif. p. 837.*

Buchholz, D.E. et al. 2013. Rapid and efficient directed differentiation of human pluripotent stem cells into retinal pigmented epithelium. Stem Cells Translational Medicine 2: 384-393; specif. pp. 384, 385, 386, 387.*

Strunnikova, N.V. et al. 2010. Transcriptome analysis and molecular signature of human retinal pigment epithelium. Human Molecular Genetics 19(21): 2468-2486; specif. p. 2469.*

(Continued)

*Primary Examiner* — Adam Weidner
*Assistant Examiner* — Sharon M. Papciak
(74) *Attorney, Agent, or Firm* — Mintz Levin Cohn Ferris Glovsky and Popeo, P.C.

(57) ABSTRACT

A population of human polygonal RPE cells is disclosed. At least 95% of the cells thereof co-express premelanosome protein (PMEL17) and cellular retinaldehyde binding protein (CRALBP), wherein the trans-epithelial electrical resistance of the cells is greater than 100 ohms. Methods of generating same are also disclosed.

15 Claims, 44 Drawing Sheets

(56) References Cited

U.S. PATENT DOCUMENTS

| | | | |
|---|---|---|---|
| 2013/0149284 A1 | 6/2013 | Malcuit et al. | |
| 2013/0195806 A1 | 8/2013 | Gay et al. | |
| 2013/0196369 A1 | 8/2013 | Hikita et al. | |
| 2013/0331393 A1 | 12/2013 | Lewis et al. | |
| 2014/0186309 A1* | 7/2014 | Klassen | A61P 27/06 |
| | | | 435/378 |
| 2015/0079046 A1 | 3/2015 | Sinden et al. | |
| 2015/0118749 A1 | 4/2015 | Idelson et al. | |
| 2015/0150796 A1 | 6/2015 | Duggan et al. | |
| 2015/0159134 A1 | 6/2015 | Choudhary et al. | |
| 2015/0175956 A1 | 6/2015 | Elhofy et al. | |
| 2015/0175964 A1* | 6/2015 | Clegg | C12N 5/0621 |
| | | | 435/405 |
| 2015/0368713 A1 | 12/2015 | Bharti et al. | |
| 2017/0079262 A1 | 3/2017 | Rowley et al. | |
| 2018/0008458 A1 | 1/2018 | Banin et al. | |
| 2018/0011092 A1 | 1/2018 | Bohana-Kashtan et al. | |
| 2018/0016553 A1 | 1/2018 | Bohana-Kashtan et al. | |
| 2018/0216064 A1 | 8/2018 | Reubinoff et al. | |
| 2018/0228846 A1 | 8/2018 | Bohana-kashtan | |
| 2018/0230426 A1 | 8/2018 | Bohana-Kashtan et al. | |
| 2018/0312805 A1 | 11/2018 | Reubinoff et al. | |
| 2019/0030168 A1 | 1/2019 | Gay et al. | |
| 2020/0085882 A1 | 3/2020 | Cuzzani et al. | |
| 2021/0000102 A1 | 1/2021 | Netzer et al. | |
| 2021/0332325 A1 | 10/2021 | Bohana-Kashtan et al. | |
| 2021/0388316 A1 | 12/2021 | Bohana-kashtan et al. | |
| 2022/0095608 A1 | 3/2022 | Netzer et al. | |
| 2022/0169981 A1 | 6/2022 | Bohana-Kashtan et al. | |
| 2022/0169982 A1 | 6/2022 | Bohana-Kashtan et al. | |
| 2022/0408719 A1 | 12/2022 | Netzer et al. | |
| 2023/0028133 A1 | 1/2023 | Banin et al. | |
| 2023/0051803 A1 | 2/2023 | Bohana-kashtan et al. | |
| 2023/0119816 A1 | 4/2023 | Netzer et al. | |

FOREIGN PATENT DOCUMENTS

| | | | |
|---|---|---|---|
| CN | 104080464 A | 10/2014 | |
| CN | 105284787 A | 2/2016 | |
| CN | 105358679 A | 2/2016 | |
| CN | 107427534 A | 12/2017 | |
| EP | 2 128 244 A1 | 12/2009 | |
| EP | 2702135 A2 | 3/2014 | |
| EP | 3240892 B9 | 7/2020 | |
| GB | 2327675 A | 2/2009 | |
| GB | 2327675 A8 | 2/2009 | |
| GB | 2327675 B | 2/2009 | |
| JP | 2008017840 A | 1/2008 | |
| JP | 2009180811 A | 8/2009 | |
| JP | 2010524457 A | 7/2010 | |
| JP | 2014-533289 A | 12/2014 | |
| JP | 2016512955 A | 5/2016 | |
| JP | 2018501281 A | 1/2018 | |
| JP | 2020511539 A | 4/2020 | |
| KR | 20100065373 A | 6/2010 | |
| KR | 20170049775 A | 5/2017 | |
| WO | WO-01/55114 A1 | 8/2001 | |
| WO | WO-02/060875 A1 | 8/2002 | |
| WO | WO-03/068233 A1 | 8/2003 | |
| WO | WO-2005/014549 A1 | 2/2005 | |
| WO | 2006070370 A2 | 7/2006 | |
| WO | WO-2008/129554 A1 | 10/2008 | |
| WO | 2011063005 A2 | 5/2011 | |
| WO | 2012149484 A2 | 11/2012 | |
| WO | WO-2013/074681 A1 | 5/2013 | |
| WO | WO-2013/114360 A1 | 8/2013 | |
| WO | WO-2013/114360 A8 | 8/2013 | |
| WO | WO-2013/184809 A1 | 12/2013 | |
| WO | WO-2013184809 A1 * | 12/2013 | C12N 5/0621 |
| WO | 2014087244 A2 | 6/2014 | |
| WO | 2014121077 A2 | 8/2014 | |
| WO | WO-2015/087231 A1 | 6/2015 | |
| WO | WO-2015/175504 A1 | 11/2015 | |
| WO | WO-2006/040763 A2 | 4/2016 | |
| WO | WO-2006/040763 A3 | 4/2016 | |
| WO | 2016108219 A1 | 7/2016 | |
| WO | 2016108240 A1 | 7/2016 | |
| WO | 2017021973 A1 | 2/2017 | |
| WO | 2017072763 A1 | 5/2017 | |
| WO | 2018170494 A1 | 9/2018 | |
| WO | 2019130061 A2 | 7/2019 | |
| WO | 2022261320 A1 | 12/2022 | |

OTHER PUBLICATIONS

Beatty, S. et al. 2000. The role of oxidative stress in the pathogenesis of age-related macular degeneration. Survey of Ophthalmology 45(2): 115-134; specif. pp. 115, 118.*

Vaajasaari, H. et al. 2011. Toward the defined and xeno-free differentiation of functional human pluripotent stem cell-derived retinal pigment epithelial cells. Molecular Vision 17: 558-575; specif. p. 559.*

Anderson et al., "Regional differences in expression of specific markers for human embryonic stem cells," Reproductive BioMedicine Online 15(1):89-98 (2007).

Bae et al. (2012) "Hypoxia Enhances the Generation of Retinal Progenitor Cells from Human Induced Pluripotent and Embryonic Stem Cells", Stem Cells and Development, 21(8):1344-1355.

Brittan et al., Bone marrow stem cell-mediated regeneration in IBD: where do we go from herer, Gastroenterology 132(3):1171-1173 (2007).

Buchholz et al., "Rapid and efficient directed differentiation of human pluripotent stem cells into retinal pigmented epithelium," Stem Cells Transplantation Medicine 2:384-393 (2013).

Buzhor et al., "Cell-based therapy approaches: the hope for incurable diseases," Regenerative Medicine 9/5:649-672 (2014).

Cao, L. et al. 2017. Polarized retinal pigment epithelium generates electrical signals that diminish with age and regulate retinal pathology. Journal of Cellular and Molecular Medicine 22: 5552-5564. specif. p. 5553.

Cho et al., "Generation of retinal pigment epithelial cells from human embryonic stem cell-derived spherical neural masses," Stem Cell Res. 9:101-109 (2012).

Clegg et al., "Derivation of retinal pigmented epithelial cells for the treatment of ocular disease," Stem Cells Handbook pp. 411-418 (2013).

Dallas et al., "Transforming Growth Factor-l3" (Chapter 53), Principles of Bone Biology vol. II, pp. 1145-1166 (2008).

Elliot et al., "Retinal pigment epithelium protection from oxidant-mediated loss of MMP-2 activation requires both MMP-14 and TIMP-2," Investigative Ophthalmology & Visual Science 47(4):1696-1702 (2006) [NIH page numbering 1-17].

Extended European Search Report received in Europe Patent Application No. 19207191.8, dated Mar. 18, 2020, 8 Pages.

Hadasit Bio-Holdings Ltd. (Nov. 3, 2014) "Cell Cure Neurosciences Ltd. Receives FDA Authorization to Initiate Phase I/IIa Trial", (Online) Press Release, Hadasit Bio-Holdings Ltd., 3 pages.

Hadasit Bio-Holdings Ltd. OpRegen. Datasheet [online]. Hadasit Bio-Holdings Ltd. Press Release, Nov. 11, 2012 [retrieved on Dec. 17, 2018]. Retrieved from the Internet: <URL: http(s)://www.hbl.co.il/press_item.asp?ID=1291>.pp. 1 and 2.

Idelson et al., "Directed differentiation of human embryonic stem cells into functional retinal pigment epithelium cells," Cell Stem Cell 5:396-408 (2009).

International Preliminary Report on Patentability received for PCT Patent International Application No. PCT/IL15/51269, dated Jul. 13, 2017, 9 Pages.

International Search Report and Written Opinion received for PCT Patent International Application No. PCT/IL15/51269, dated Mar. 24, 2016, 12 Pages.

Jostock et al. (2001) "Soluble Gp130 is the Natural Inhibitor of Soluble Interleukin-6 Receptor Transsignaling Responses", European Journal of Biochemistry, 268:160-167.

Kamao, et al., "Characterization of human induced pluripotent stem cell-derived retinal pigment epithelium cell sheets aiming for clinical application," Stem Cell Reports 2:205-221 (2014).

(56) References Cited

OTHER PUBLICATIONS

Lund, et al., "Human embryonic stem cell-derived cells rescue visual function in dystrophic RCS rats," Cloning and Stem Cells 8.3:189-199 (2006).
Masuda et al., "SOX9, through Interaction with Microphthalmia-associated Transcription Factor (MITF) and OTX2, Regulates BEST1 Expression in the Retinal Pigment Epithelium," Journal of Biological Chemistry 285 (35):26933-26944 (2010).
Onnela et al. (Dec. 22, 2011) "Electric Impedance of Human Embryonic Stem Cell-Derived Retinal Pigment Epithelium", Medical & Biological Engineering & Computing, 50:107-116.
R&D Systems. Interleukin 6. Datasheet [online]. R&D Systems 1999 Catalog [retrieved on Dec. 16, 2018]. Retrieved from the Internet: <URL: http(s)://www.rndsystenns.conn/resources/articles/interleukin-6>.pp. 1-4. specif. pp. 1, 2.
Shi et al., "Control of chemokine gradients by the retinal pigment epithelium," Investigative Ophthamology & Visual Science 49(10):4620-4630 (2008) [NIH page numbering 1-23].
Simo, R. et al. 2010. The retinal pigment epithelium: something more than a constituent of the blood-retinal barrier—implications for the pathogenesis of diabetic retinopathy. Journal of Biomedicine and Biotechnology 2010: 1-15. specif. p. 2.
Singh et al., "Functional analysis of serially expanded human iPS cell-derived RPE cultures," Investigative Ophthamology & Visual Science 54:6767-6778 (2013).
Skeie et al., "Angiogenin in age-related macular degeneration," Molecular Vision 17:576-582 (2011).
Subrizi et al. (Aug. 11, 2012) "Generation of Hesc-Derived Retinal Pigment Epithelium on Biopolymer Coated Polyirnide Membranes", Biomaterials, 33:8047-8054.
Tannenbaum et al., "Derivation of xeno-free and GMP-grade human embryonic stem cells—platforms for future clincial applications," Plos One 7:6 p. e35325 (2012).
Vaajasaari et al., "Toward the defined and xeno-free differentiation of functional human pluripotent stem cell-derived retinal pigment epithelial cells," Molecular Vision 17:558-575 (2011).
Vadlapatla, R. et al. Sep. 15, 2013. Molecular expression and functional activity of efflux and influx transporters in hypoxia induced retinal pigment epithelial cells. International Journal of Pharmacy 454(1): 444-452. NIH Public Access numbering 1-22. specif. pp. 1, 8.
Vugler et al., "Elucidating the phenomenon of HESC-derived RPE: anatomy of cell genesis, expansion and retinal transplantation," Experimental Neurology 214.2:347-361 (2008).
Wu, D. et al. 2011. Induction and testing of hypoxia in cell culture. Journal of Visualized Experiments 54: 1-4. specif. p. 3.
Yamamoto et al. (2003) "Increased Soluble Interleukin-6 Receptor in Vitreous Fluid of Proliferative Vitreoretinopathy", Current Eye Research, 26(1):9-14.
Zhang et al., "TGF-l3 superfamily: signaling in development and disease," Journal of Cell Science 126:4809-4813 (2013).
Zhu et al., Polarized secretion of PEDF from human embryonic stem-cell derived RPE promotes retinal progenitor cell survival, Invest. Ophthalmol. Vis. Sci. 52(3):1573-1585 (2011).
Zhang et al., Protein Cell, (2014), vol. 5, No. 1, pp. 48-58.
Reubinoff et al., Nat Biotechnol, (200005), vol. 18, No. 5, p. 559, 2000.
Proc. Natl. Acad. Sci. USA, (1995), vol. 92, p. 7844.
Gardner et al., Fertil. Steril., (1998), vol. 69, p. 84.
Doetschman et al., Dev Biol., (1988), vol. 127, pp. 224-227.
Iannaccone et al., Dev Biol., (1994), vol. 163, pp. 288-292.
Giles et al., Mol Reprod Dev., (1993), vol. 36, pp. 130-138.
Graves; Moreadith, Mol Reprod Dev., (1993), vol. 36, pp. 424-433.
Notarianni et al., J Reprod Fertil Suppl, (1991), vol. 43, pp. 255-260.
Wheeler, Reprod Fertil Dev, (1994), vol. 6, pp. 563-568.
Mitalipova et al., Cloning., (2001), vol. 3, pp. 59-67.
Thomson et al., Proc Natl Acad Sci U S A., (1995), vol. 92, pp. 7844-7848.
Thomson et al., Biol Reprod., (1996), vol. 55, pp. 254-259.
Chung et al., Cell Stem Cell, (Feb. 7, 2008), vol. 2, No. 2, pp. 113-117.
Kalkan et al., Phil. Trans. R. Soc. B, vol. 369, p. 540, 2014.
Xu C et al., "Feeder-free growth of undifferentiated human embryonic stem cells", Nat Biotechnol., (2001), vol. 19, doi:doi:10.1038/nbt1001-971, pp. 971-974, XP002672078.
Thomson Ja et al., Science, (1998), vol. 282, pp. 1145-1147.
Yin et al. (Jul. 25, 2003) "The Effects of Different Intraocular Irrigating Solutions on the Apoptosis of Cultured RPE Cells", Graefe's Archive for Clinical and Experimental Opthalmology, 241(10):834-839.
(Nov. 4, 2014) BioTime Annual Meeting Shareholder Update, Cell Cure Neurosciences Ltd., Slides 55-76 (22 pages).
(Feb. 17, 2015) Cell Cure Neurosciences Ltd. Provides Update on its Product Development and Partnering Activities, 3 pages.
(Apr. 2008) Content and Review of Chemistry, Manufacturing, and Control (CMC) Information for Human Somatic Cell Therapy Investigational New Drug Applications (INDs), Guidance for FDA Reviewers and Sponsors, 36 pages.
Evidence for publication date of D12 by the U.S. Securities and Exchange Commission (SEC), 3 pages, downloaded Jul. 2, 2022.
Extended European Search Report received for European Patent Application No. 15875361.6, dated May 5, 2018, 10 pages.
Extended European Search Report received in European Application No. 21170654.4, dated Oct. 27, 2021, 8 pages.
(Nov. 4, 2014) Form 8-K, submitted to the SEC by BioTime on Nov. 4, 2014, 2 pages.
International Preliminary Report on Patentability received for International Application No. PCT/IL2015/051270, dated Jul. 13, 2017, 8 pages.
International Preliminary Report on Patentability received for PCT International Application No. PCT/IL2015/050456, dated Jul. 13, 2017, 11 pages.
International Search Report and Written Opinion received for International Application No. PCT/IL2015/051270, dated Mar. 29, 2016, 11 pages.
International Search Report and Written Opinion Received for PCT Patent International Application No. PCT/IL2015/050456, dated Aug. 12, 2015, 14 pages.
MTeSR™ 1, Defined, feeder-free maintenance medium for human ES and iPS cells, Stem Cell Technologies, 2 pages, Copyright 2020.
Notice of Opposition received in European Patent Application No. 15832698.3, dated Mar. 28, 2022, 34 pages (Strawman Opposition).
Notice of Opposition received in European Patent Application No. 15832698.3, dated Mar. 28, 2022, 68 pages (Dixon Opposition).
Notice of Opposition received in European Patent Application No. 15875361.6, dated Sep. 23, 2021, 37 pages.
Notice of Opposition received in European Patent Application No. 15875361.6, dated Oct. 12, 2021, 47 pages.
Notice of Opposition received in European Patent Application No. 16795439.5, dated Jun. 8, 2022, 16 pages.
Notice of Opposition received in European Patent Application No. 15875361.6, dated Sep. 22, 2021, 45 pages.
Patentee's letter, dated Mar. 27, 2019, 8 pages.
Pineal Body, Harmonizome, 3 pages, downloaded Nov. 3, 2022.
(Apr. 13, 2015) Safety and Efficacy Study of OpRegen for Treatment of Advanced Dry-Form Age-Related Macular Degeneration, History of Changes for Study: NCT02286089, 10 pages.
(Feb. 5, 2019) Safety and Efficacy Study of OpRegen for Treatment of Advanced Dry-Form Age-Related Macular Degeneration, History of Changes for Study: NCT02286089, 12 pages.
(Nov. 5, 2014) Safety and Efficacy Study of OpRegen for Treatment of Advanced Dry-Form Age-Related Macular Degeneration, Accession No. NCT02286089, 5 pages.
Search Opinion issued in respect of EP3240612, dated May 11, 2018, 5 pages.
SEC Directory Listing for BioTime's SEC submission, Nov. 4, 2014, 16 pages.
Ahmado et al. (Sep. 2011) "Induction of Differentiation by Pyruvate and DMEM in the Human Retinal Pigment Epithelium Cell Line ARPE-19", Investigative Ophthalmology & Visual Science, 52(10):7148-7159.

(56) References Cited

OTHER PUBLICATIONS

Algvere et al. (Mar. 1997) "Transplantation of RPE in Age-related Macular Degeneration: Observations in Disciform Lesions and Dry RPE Atrophy", Graefe's Archive for Clinical and Experimental Ophthalmology, 235(3):149-158.
Bharti et al. (Feb. 2011) "The New Paradigm: Retinal Pigment Epithelium Cells Generated from Embryonic or Induced Pluripotent Stem Cells", Pigment Cell & Melanoma Research, 24(1):21-34 (21 pages).
Bigar et al. (Aug. 1992), "Corneal Transplantation", Current Opinion in Ophthalmology, 3(4):473-481.
Brandl et al. (May 7, 2014) "In-Depth Characterisation of Retinal Pigment Epithelium (RPE) Cells Derived from Human Induced Pluripotent Stem (hiPSC)", NeuroMolecular Medicine, 16(3):551-564.
Buchholz et al. (Oct. 2009) "Derivation of Functional Retinal Pigmented Epithelium from Induced Pluripotent Stem Cells", Stem Cells, 27(10):2427-2434.
Burdon et al. (1995) "A Survey of Corneal Graft Practice in the United Kingdom", Eye, 9(Suppl.):6-12.
Cantz Tobias, "Declaration by Prof. Tobias Cantz", 13 pages, Sep. 20, 2021.
Carr et al. (Dec. 2009) "Protective Effects of Human iPS-Derived Retinal Pigment Epithelium Cell Transplantation in the Retinal Dystrophic Rat", PLoS One, 4(12): e8152 (12 pages).
Deeg et al. (Nov. 5, 2007) "CRALBP is a Highly Prevalent Autoantigen for Human Autoimmune Uveitis", Clinical and Developmental Immunology, 2007:39245 (6 pages).
Du et al. (May 2011), "Induced Pluripotent Stem Cell Therapies for Geographic Atrophy of Age-Related Macular Degeneration", Seminars in Ophthalmology, 26(3): 216-224.
Eitle Hoffmann, (Dec. 10, 2018) "Patentee's letter", 4 pages.
Genbank, (Feb. 16, 2005) "*Homo sapiens* Genomic DNA, 21q Region, Clone: 289H18X26, Genomic Survey Sequence", Accession No. AG014699.1, 1 page.
Gropp et al. (2012) "Standardization of the Teratoma Assay for Analysis of Pluripotency of Human ES Cells and Biosafety of Their Differentiated Progeny", PLOS One, 7(9):1-10.
Idelson et al. (2009) "Directed Differentiation of Human Embryonic Stem Cells into Functional Retinal Pigment Epithelium Cells", Supplemental Data, Cell Stem Cell, 5:(Suppl.)1-10.
Kamao et al. (2014) "Characterization of Human Induced Pluripotent Stem Cell-Derived Retinal Pigment Epithelium Cell Sheets Aiming for Clinical Application", Supplemental Information, Stem Cell Reports, 2:(Suppl.)1-25.
Kokkinaki et al. (May 2011) "Human Induced Pluripotent Stem-Derived Retinal Pigment Epithelium (RPE) Cells Exhibit Ion Transport, Membrane Potential, Polarized Vascular Endothelial Growth Factor Secretion, and Gene Expression Pattern Similar to Native RPE", Stem Cells, 29(5):825-835.
Krohne et al. (2012) "Generation of Retinal Pigment Epithelial Cells from Small Molecules and OCT4 Reprogrammed Human Induced Pluripotent Stem Cells", Stem Cells Translational Medicine, 1(2):96-109.
Lane et al. (2014) "Engineering Efficient Retinal Pigment Epithelium Differentiation From Human Pluripotent Stem Cells", Stem Cells Translational Medicine, 3(11):1295-1304.
Maminishkis et al. (Aug. 2006) "Confluent Monolayers of Cultured Human Fetal Retinal Pigment Epithelium Exhibit Morphology and Physiology of Native Tissue", Investigative Ophthalmology & Visual Science, 47(8):3612-3624 (30 pages).
Maruotti et al. (2013) "A Simple and Scalable Process for the Differentiation of Retinal Pigment Epithelium from Human Pluripotent Stem Cells", Stem Cells Translational Medicine, 2(5):341-354.
McGill et al. (2017) "Long-Term Efficacy of GMP Grade Xeno-Free hESC-Derived RPE Cells Following Transplantation", Translational Vision Science and Technology, 6(3):17 (18 pages).
Ohno-Matsui et al. (2005) "The Effects of Amniotic Membrane on Retinal Pigment Epithelial Cell Differentiation", Molecular Vision, 11:1-10.
Oplinger et al. (Apr. 1998), "A Comparison of Corneal Autografts with Homografts", Ophthalmic Surgery, Lasers and Imaging Retina, 29(4):305-308.
Parvini et al. (Oct. 2014) "Human Pluripotent Stem Cell-derived Retinal Pigmented Epithelium in Retinal Treatment: From Bench to Bedside", Molecular Neurobiology, 50(2):597-612.
Patel et al. (2015) "Geographic Atrophy: Clinical Impact and Emerging Treatments", Ophthalmic Surgery, Lasers and Imaging Retina, 46(1):8-13.
Patel et al. (Apr. 2000), "Indications for and Outcomes of Repeat Penetrating Keratoplasty, 1989-1995", Ophthalmology, 107(4):719-724.
Peng et al. (Jul. 2013) "Engineering a Blood-Retinal Barrier with Human Embryonic Stem Cell-Derived Retinal Pigment Epithelium: Transcriptome and Functional Analysis", Stem Cells Translational Medicine, 2(7):534-544.
Pennington et al. (Feb. 2015) "Defined Culture of Human Embryonic Stem Cells and Xeno-Free Derivation of Retinal Pigmented Epithelial Cells on a Novel, Synthetic Substrate", Stem Cells Translational Medicine, 4(2):165-177.
Peyman et al. (Feb. 1991), "A Technique for Retinal Pigment Epithelium Transplantation for Age-related Macular Degeneration Secondary to Extensive Subfoveal Scarring", Ophthalmic Surgery, Lasers and Imaging Retina, 22(2):102-108 (9 pages).
Przybyla et al. (2012) "Probing Embryonic Stem Cell Autocrine and Paracrine Signaling Using Microfluidics", Annual Review of Analytical Chemistry, 5:293-315.
Schwartz et al. (Feb. 25-Mar. 2, 2012) "Embryonic Stem Cell Trials for Macular Degeneration: A Preliminary Report", The Lancet, 379(9817):713-720.
Schwartz et al. (2015) "Human Embryonic Stem Cell-Derived Retinal Pigment Epithelium in Patients with Age-Related Macular Degeneration and Stargardt's Macular Dystrophy: Follow-Up of Two Open-Label Phase 1/2 Studies", Lancet, 385(9967):509-516.
Sieving et al. (Mar. 7, 2006) "Ciliary Neurotrophic Factor (CNTF) for human retinal degeneration: Phase I Trial of CNTF Delivered by Encapsulated Cell Intraocular Implants", Proceedings of the National Academy of Sciences of the United States of America, 103(10):3896-3901.
Sonoda et al. (2010) "Attainment of Polarity Promotes Growth Factor Secretion by Retinal Pigment Epithelial Cells: Relevance to Age-related Macular Degeneration", Aging, 2(1):28-42.
Sperling Laura E. (2013) "Embryonic Stem Cell Therapy—From Bench to Bed", Pluripotent Stem Cells, Chapter 18, 18 pages.
Srinivasan et al. (Apr. 2015), "TEER Measurement Techniques for In Vitro Barrier Model Systems", Journal of Laboratory Automation, 20(2):107-126 (35 pages).
Stout et al. (May 2011) "Surgical Approaches to Gene and Stem Cell Therapy for Retinal Disease", Human Gene Therapy, 22(5):531-535.
Thomson et al. (1998), "Primate Embryonic Stem Cells", Current Topics in Developmental Biology, 38:133-165.
Thomson et al. (Nov. 6, 1998) "Embryonic Stem Cell Lines Derived from Human Blastocysts", Science, 282(5391):1145-1147.
Thomson et al. (Aug. 1995) "Isolation of a Primate Embryonic Stem Cell Line", Proceedings of the National Academy of Sciences of the United States of America, 92(17):7844-7848.
Tsubota Kazuo, (Nov.-Dec. 1999), "Ocular Surface Management in Corneal Transplantation, a Review", Japanese Journal of Ophthalmology, 43(6):502-508.
Watt et al. (May 2013) "PMEL: a pigment cell-specific model for functional amyloid formation", Pigment Cell & Melanoma Research, 26(3):300-315 (27 pages).
Zhu et al. (Jan. 2013), "Three-Dimensional Neuroepithelial Culture from Human Embryonic Stem Cells and Its Use for Quantitative Conversion to Retinal Pigment Epithelium", PLoS One, 8(1): e54552:13pages.
Fronk et al. (2016) "Methods for Culturing Retinal Pigment Epithelial Cells: a Review of Current Protocols and Future Recommendations", Journal of Tissue Engineering, 7:1-23.
Kamao et al. (Jan. 2017) "Evaluation of the Surgical Device and Procedure for Extracellular Matrix-Scaffold-Supported Human iPSC-

(56) References Cited

OTHER PUBLICATIONS

Derived Retinal Pigment Epithelium Cell Sheet Transplantation", Retinal Cell Biology, 58(1):211-220.
Yang et al. (Jul. 28, 2021) "Functions and Diseases of the Retinal Pigment Epithelium", Frontiers in Pharmacology, 12(727870):1-7.
Zhang et al. (2015) "Synergistic Protective Effects of Escin and Low-Dose Glucocorticoids Against Vascular Endothelial Growth Factor-Induced Blood-Retinal Barrier Breakdown in Retinal Pigment Epithelial and Umbilical Vein Endothelial Cells", Molecular Medicine Reports, 11:1372-1377.
(Apr. 5, 2022) Cryostor: Optimized Freeze Media for Cells and Tissues, Biolife Solutions, 1-2.
(2022) Dulbecco's Modified Eagle's Medium (DMEM), Laboratory Notes, 1-5.
Extended European Search Report for Application No. EP 21215492.6 dated Apr. 8, 2022, 12 pages.
Extended European Search Report for Application No. EP18893743.7 dated Aug. 10, 2021, 12 pages.
International Preliminary Report on Patentability received for International Application No. PCT/IB2018/001579 dated Jul. 9, 2020, 18 pages.
International Search Report and Written Opinion received for International Application No. PCT/IB2018/001579 dated Oct. 22, 2019, 21 pages.
(Dec. 20, 2021) Lineage Established Exclusive Worldwide Collaboration with Genentech for the Development and Commercialization of OpRegen® RPE Cell Therapy for the Treatment of Ocular Disorders, Business Wire Press Release, 5 pages.
(2022) Protic vs. Aprotic Solvents, Chemistry Score, 1-4.
Aoi et al. (Aug. 1, 2008) "Generation of Pluripotent Stem Cells from Adult Mouse Liver and Stomach Cells", Science, 321(5889):699-702.
Database Genbank (Oct. 26, 2022) "PMEL premelanosome protein [*Homo sapiens* (human) ]", Gene ID: 6490, 30 pages.
Hadasit Bio-Holdings Ltd. (2012) "OpRegen", Datasheet(Online), Hadasit Bio-Holding Ltd., Press Release, 2 pages.
Hsiung et al. (Jan. 2015) "Polarized Human Embryonic Stem Cell-derived Retinal Pigment Epithelial Cell Monolayers Have Higher Resistance to Oxidative Stress-induced Cell Death Than Nonpolarized Cultures", Stem Cells Translational Medicine, 4(1):10-20.
Lu et al. (Sep. 2009) "Long-term Safety and Function of RPE From Human Embryonic Stem Cells in Preclinical Models of Macular Degeneration", Stem Cells, 27(9):2126-2135.
Park et al. (Jan. 10, 2008), "Reprogramming of Human Somatic Cells to Pluripotency with Defined Factors", Nature, 451(7175):141-146.
Pennington et al. (Mar. 18, 2021) "Xeno-free Cryopreservation of Adherent Retinal Pigmented Epithelium Yields Viable and Functional Cells in Vitro and in Vivo", Scientific Reports, 11:6286 (14 pages).
Pfeffer et al. (Sep. 2014) "Cell Culture of Retinal Pigment Epithelium: Special Issue", Experimental Eye Research, 126:1-4.

Reubinoff et al. (Apr. 2000) "Embryonic Stem Cell Lines From Human Blastocysts: Somatic Differentiation in Vitro", Nature Biotechnology, 18(4):399-404.
Shamblott et al. (Nov. 1998), "Derivation of Pluripotent Stem Cells from Cultured Human Primordial Germ Cells", Proceedings of the National Academy of Sciences of the United States of America, 95(23):13726-13731.
Takahashi et al. (Nov. 30, 2007) "Induction of Pluripotent Stem Cells from Adult Human Fibroblasts by Defined Factors", Cell, 131(5):861-872.
Tsai. et al. (Dec. 2009) "Dimethyl Sulphoxide Dose-response on Rat Retinal Function" Documenta Ophthalmologica, 119(3):199-207.
UNIPROT (Aug. 5, 2022) "RLBP1 retinaldehyde binding protein 1 [*Homo sapiens* (human)]", Gene ID: 6017, 23 pages.
Yamanaka Shinya, (Jun. 7, 2007), "Strategies and New Developments in the Generation of Patient-Specific Pluripotent Stem Cells", Cell Stem Cell, 1(1):39-49.
Becerra et al. (Feb. 2004) "Pigment Epithelium-derived Factor in the Monkey Retinal Pigment Epithelium and Interphotoreceptor Matrix: Apical Secretion and Distribution", Experimental Eye Research, 78(2):223-234.
Blaauwgeers et al. (Aug. 1999) "Polarized Vascular Endothelial Growth Factor Secretion by Human Retinal Pigment Epithelium and Localization of Vascular Endothelial Growth Factor Receptors on the Inner Choriocapillaris. Evidence for a Trophic Paracrine Relation", The American Journal of Pathology, 155(2):421-428.
Hrabovszky et al. (Apr. 1995) "Triple-labeling Method Combining Immunocytochemistry and in Situ Hybridization Histochemistry: Demonstration of Overlap Between Fos-immunoreactive and Galanin mRNA-expressing Subpopulations of Luteinizing Hormone-releasing Hormone Neurons in Female Rats", Journal of Histochemistry and Cytochemistry, 43(4):363-370.
Galvao et al. (Mar. 2014) "Unexpected Low-dose Toxicity of the Universal Solvent DMSO", The FASEB Journal, 28(3):1317-1330.
Hill et al. (Jan. 1975) "Dimethyl Sulfoxide in the Treatment of Retinal Disease", Annals of the New York Academy of Sciences, 243(1):485-490.
Kociok et al. (Aug. 1998) "The mRNA expression of cytokines and their receptors in cultured iris pigment epithelial cells: A comparison with retinal pigment epithelial cells", Experimental Eye Research, 67:237-250.
Stylianou et al. (2006) "Novel cryoprotectant significantly improves the post-thaw recovery and quality of HSC from CB", Cytotherapy. 8(1):57-61. doi: 10.1080/14653240500501021. PMID: 16627345.
NCBI entry for "PMEL", Mar. 10, 2022.
NCBI entry for "RLBP1", Mar. 10, 2022.
Business Wire Press Release, "Lineage Established Exclusive Worldwide Collaboration with Genentech for the Development and Commercialization of OpRegen® RPE Cell Therapy for the Treatment of Ocular Disorders", Dec. 20, 2021 (5 pages).
Subrizi et al. (Aug. 11, 2012) "Generation of hESC-Derived Retinal Pigment Epithelium on Biopolymer Coated Polyirnide Membranes", Biomaterials, 33(32):8047-8054.
FDA Guidance: Content and Review of Chemistry, Manufacturing, and Control (CMC) Information for Human Somatic Cell Therapy Investigational New Drug Applications (INDs), Apr. 2008.

\* cited by examiner

Manufacturing process, steps 1-3; Generation of human cord fibroblast feeder WCB Materials:

QC tests:

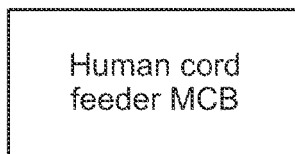
Human cord feeder MCB

Step 1:
Thawing and expansion with DMEM Medium (Hyclone) + 20% Human serum (Lonza)

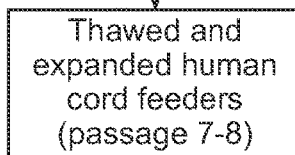
Thawed and expanded human cord feeders (passage 7-8)

Before proceeding to Step 2:
- Cell number
- Viability
- Safety
  - Sterility
  - Mycoplasma
  - LAL
- Identity
  - Morphology
  - Karyotype

Step 2:
Irradiation, 3500 rads
Irradiation equipment

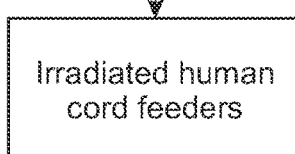
Irradiated human cord feeders

Step 3:
Cryopreservation with cryopreservation medium (90% Human serum (Lonza) + 10 DMSO (WAK-Chemie))

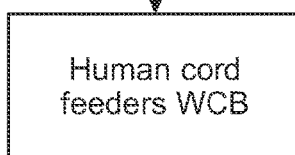
Human cord feeders WCB

Before proceeding to Step 4:
- Cell number
- Viability
- Proliferation potential
- Identity
  - DNA fingerprint(STR)
- Potency
  - Morphology of HAD-C 102 hESCs grown on feeders for 3-5 passages
  - Pluripotent markers expression (TRA-1-60, TRA-1-81, Oct4, Alkaline Phosphatase)

FIG. 12

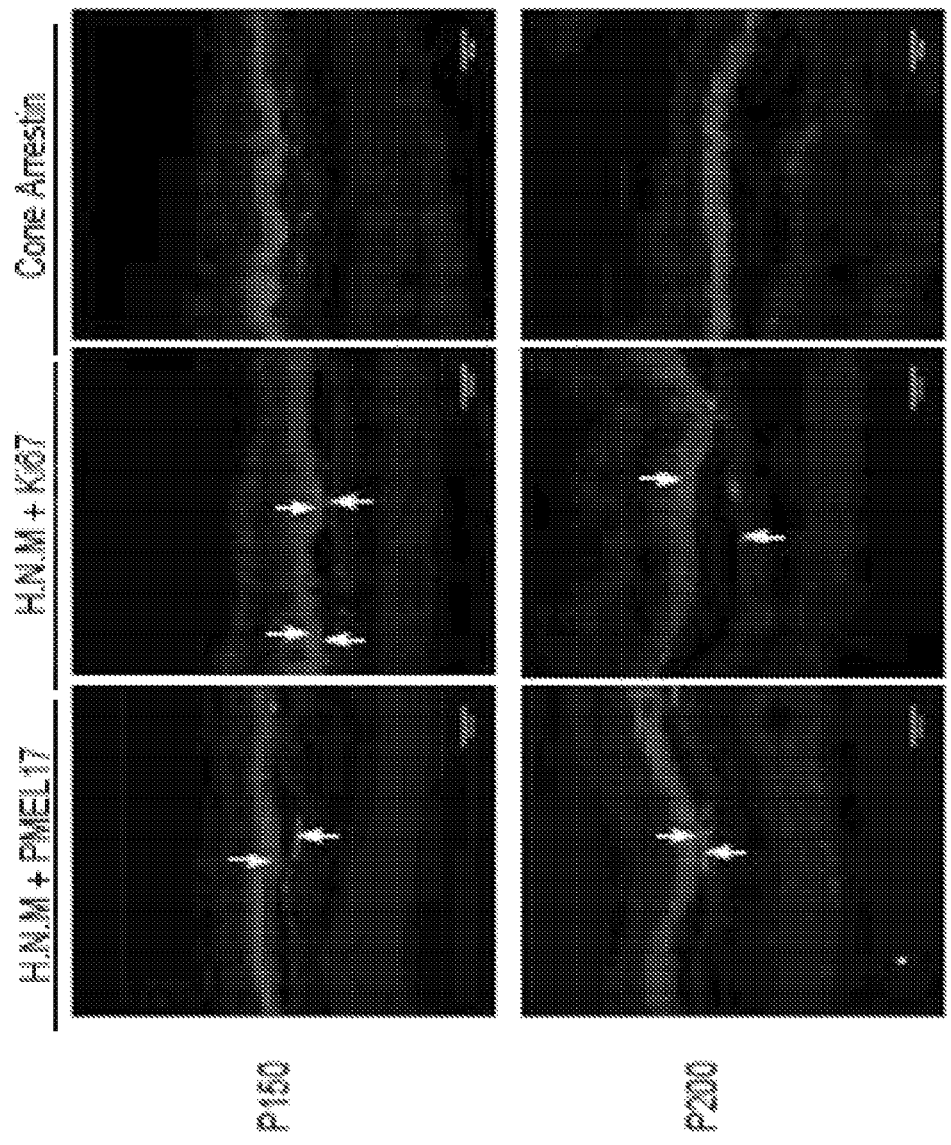
FIG. 24 – continued

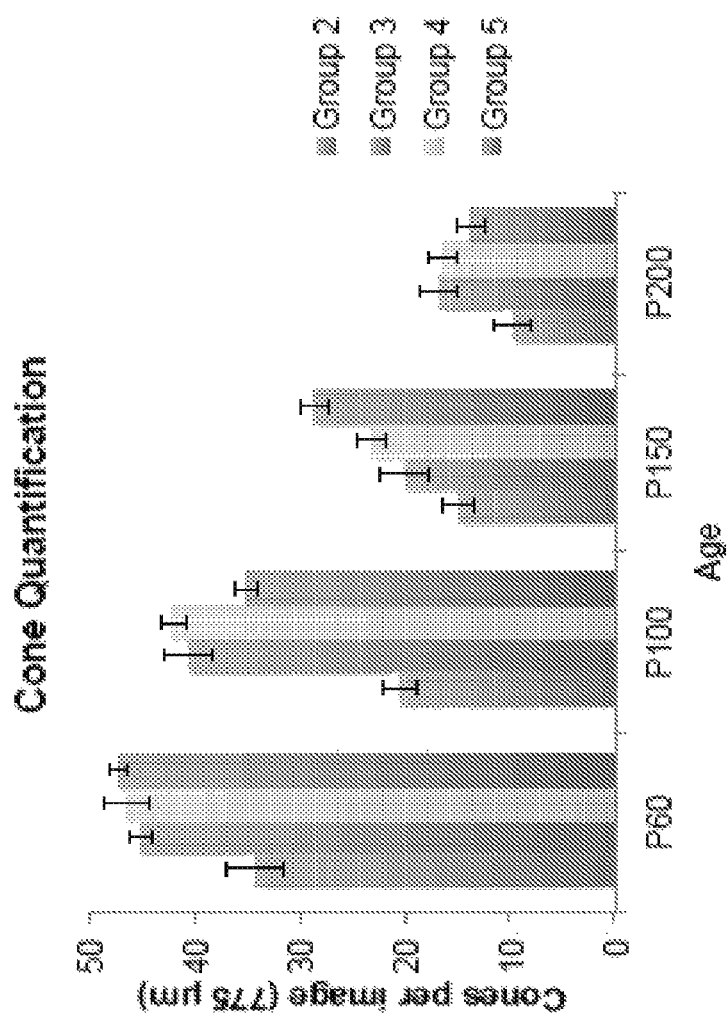

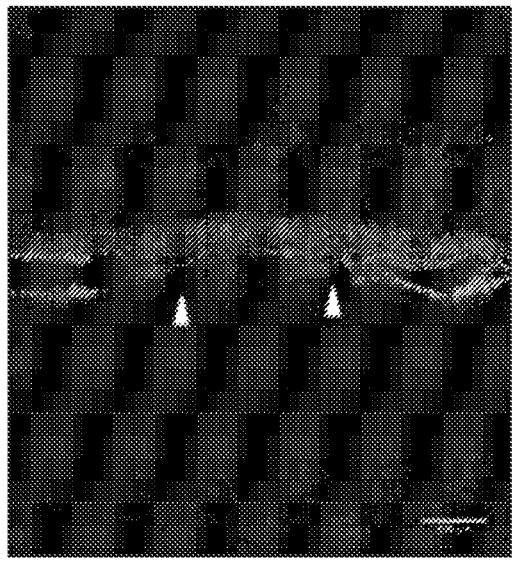
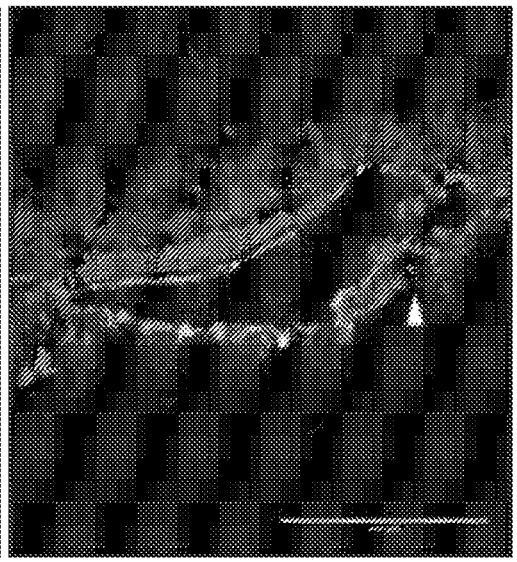
FIG. 26A  FIG. 26B
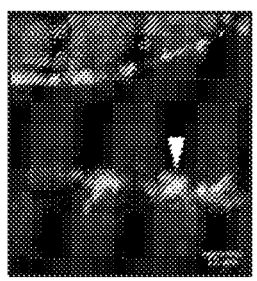 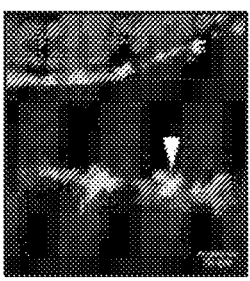 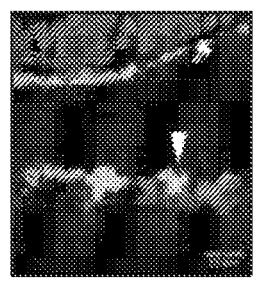 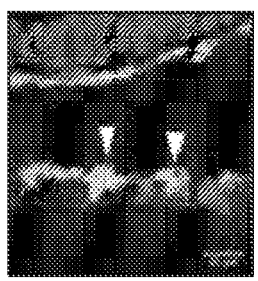
FIG. 26C  FIG. 26D  FIG. 26E  FIG. 26F
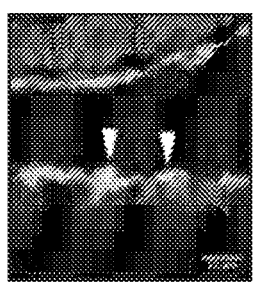 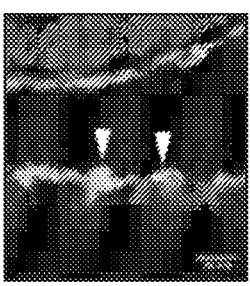 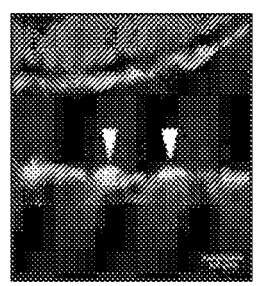 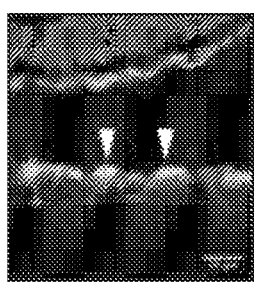
FIG. 26G  FIG. 26H  FIG. 26I  FIG. 26J

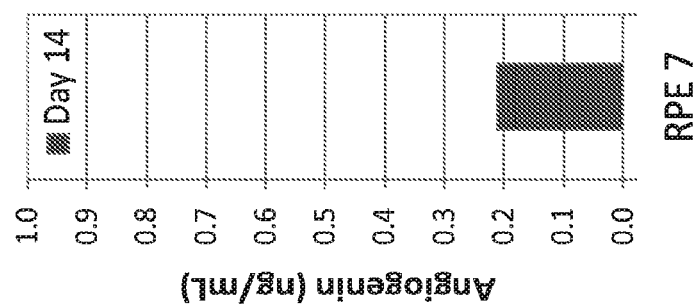

RPE CELL POPULATIONS AND METHODS OF GENERATING SAME

CROSS REFERENCE TO RELATED APPLICATIONS

This application is a continuation of U.S. application Ser. No. 15/539,473, filed Jun. 23, 2017, which is a national stage filing of International Application No. PCT/IL2015/051269, filed Dec. 30, 2015, which claims priority to U.S. Provisional Application No. 62/195,309, filed Jul. 22, 2015, and U.S. Provisional Application No. 62/116,972, filed Feb. 17, 2015, and U.S. Provisional Application No. 62/097,753, filed Dec. 30, 2014, each of which is hereby incorporated by reference in its entirety and for all purposes.

FIELD AND BACKGROUND OF THE INVENTION

The present invention, in some embodiments thereof, relates to retinal pigment epithelium cells and, more particularly, but not exclusively, to assessment of such cells as a therapeutic. The present invention also relates to generation of retinal pigment epithelium cells from embryonic stem cells.

The retinal pigment epithelium (RPE) is a monolayer of pigmented cells, which lies between the neural retina and the choriocapillaris. The RPE cells play crucial roles in the maintenance and function of the retina and its photoreceptors. These include the formation of the blood-retinal barrier, absorption of stray light, supply of nutrients to the neural retina, regeneration of visual pigment, and uptake and recycling of shed outer segments of photoreceptors.

Retinal tissue may degenerate for a number of reasons. Among them are: artery or vein occlusion, diabetic retinopathy and retinopathy of prematurity, which are usually hereditary. Diseases such as retinitis pigmentosa, retinoschisis, lattice degeneration, Best disease, and age related macular degeneration (AMD) are characterized by progressive types of retinal degeneration.

RPE cells may potentially be used for cell replacement therapy of the degenerating RPE in retinal diseases mentioned above. It may be also used as a vehicle for the introduction of genes for the treatment of retinal degeneration diseases. These cells may also serve as an in vitro model of retinal degeneration diseases, as a tool for high throughput screening for a therapeutic effect of small molecules, and for the discovery and testing of new drugs for retinal degeneration diseases. RPE cells could also be used for basic research of RPE development, maturation, characteristics, properties, metabolism, immunogenicity, function and interaction with other cell types.

Human fetal and adult RPE has been used as an alternative donor source for allogeneic transplantation. However, practical problems in obtaining sufficient tissue supply and the ethical concerns regarding the use of tissues from aborted fetuses limit widespread use of these donor sources. Given these limitations in supply of adult and fetal RPE grafts, the potential of alternative donor sources have been studied. Human pluripotent stem cells provide significant advantages as a source of RPE cells for transplantation. Their pluripotent developmental potential may enable their differentiation into authentic functional RPE cells, and given their potential for infinite self renewal, they may serve as an unlimited donor source of RPE cells. Indeed, it has been demonstrated that human embryonic stem cells (hESCs) and human induced pluripotent stem cells (iPS) differentiate into RPE cells in vitro, attenuate retinal degeneration and preserve visual function after subretinal transplantation to the Royal College of Surgeons (RCS) rat model of retinal degeneration that is caused by RPE dysfunction. Therefore, pluripotent stem cells may be an unlimited source for the production of RPE cells.

Current protocols for the derivation of RPE cells from pluripotent stem cells yields mixed populations of pigmented and non-pigmented cells. However, pure populations of pigmented cells are desired for the usage of RPE cells in basic research, drug discovery and cell therapy.

Background art includes WO 2013/114360, WO 2008/129554 and WO 2013/184809.

SUMMARY OF THE INVENTION

According to an aspect of some embodiments of the present invention there is provided a population of human polygonal RPE cells, wherein at least 95% of the cells thereof co-express premelanosome protein (PMEL17) and cellular retinaldehyde binding protein (CRALBP), wherein the trans-epithelial electrical resistance of the population of cells is greater than 100 ohms.

According to an aspect of some embodiments of the present invention there is provided a population of human RPE cells, wherein at least 80% of the cells thereof co-express premelanosome protein (PMEL17) and cellular retinaldehyde binding protein (CRALBP) and wherein cells of the population secrete each of angiogenin, tissue inhibitor of metalloproteinase 2 (TIMP2), soluble glycoprotein 130 (sgp130) and soluble form of the ubiquitous membrane receptor 1 for tumor necrosis factor-α (sTNF-R1).

According to embodiments of the invention, the cells of the population secrete each of angiogenin, tissue inhibitor of metalloproteinase 2 (TIMP2), soluble glycoprotein 130 (sgp130) and soluble form of the ubiquitous membrane receptor 1 for tumor necrosis factor-α (sTNF-R1).

According to embodiments of the invention, the cells secrete the angiogenin, the TIMP2, the sgp130 or the sTNF-R1 in a polarized manner.

According to embodiments of the invention, the cells secrete each of the angiogenin, the TIMP2, the sgp130 and the sTNF-R1 in a polarized manner.

According to embodiments of the invention, the ratio of apical secretion of sgp130:basal secretion of sgp130 is greater than 1.

According to embodiments of the invention, the ratio of apical secretion of sTNF-R1:basal secretion of sTNF-R1 is greater than 1.

According to embodiments of the invention, the ratio of basal secretion of angiogenin:apical secretion of angiogenin is greater than 1.

According to embodiments of the invention, the ratio of apical secretion of TIMP2:basal secretion of TIMP2 is greater than 1.

According to embodiments of the invention, the number of Oct4$^+$TRA-1-60$^+$ cells in the population is below 1:250,000.

According to embodiments of the invention, at least 80% of the cells express Bestrophin 1, as measured by immunostaining.

According to embodiments of the invention, at least 80% of the cells express Microphthalmia-associated transcription factor (MITF), as measured by immunostaining.

According to embodiments of the invention, more than 50% of the cells express paired box gene 6 (PAX-6) as measured by FACS.

According to embodiments of the invention, the cells secrete greater than 750 ng of Pigment epithelium-derived factor (PEDF) per ml per day.

According to embodiments of the invention, the cells secrete PEDF and vascular endothelial growth factor (VEGF) in a polarized manner.

According to embodiments of the invention, the ratio of apical secretion of PEDF:basal secretion of PEDF is greater than 1.

According to embodiments of the invention, the ratio remains greater than 1 following incubation for 8 hours at 2-8° C.

According to embodiments of the invention, the trans-epithelial electrical resistance of the population of cells is greater than 100 ohms.

According to embodiments of the invention, the trans-epithelial electrical resistance of the cells remains greater than 100 ohms following incubation for 8 hours at 2-8° C.

According to embodiments of the invention, the ratio of basal secretion of VEGF:apical secretion of VEGF is greater than 1.

According to embodiments of the invention, the ratio remains greater than 1 following incubation for 8 hours at 2-8° C.

According to embodiments of the invention, the cell population is capable of rescuing visual acuity in the RCS rat following subretinal administration.

According to embodiments of the invention, the cell population is capable of rescuing photoreceptors for at least 180 days post-subretinal administration in the RCS rat.

According to embodiments of the invention, the cell population is generated by ex-vivo differentiation of human embryonic stem cells.

According to embodiments of the invention, the cell population is generated by:

(a) culturing human embryonic stem cells in a medium comprising nicotinamide so as to generate differentiating cells, wherein the medium is devoid of activin A;

(b) culturing the differentiating cells in a medium comprising nicotinamide and activin A to generate cells which are further differentiated towards the RPE lineage; and (c) culturing the cells which are further differentiated towards the RPE lineage in a medium comprising nicotinamide, wherein the medium is devoid of activin A.

According to embodiments of the invention, the embryonic stem cells are propagated in a medium comprising bFGF and TGFβ.

According to embodiments of the invention, the embryonic stem cells are cultured on human cord fibroblasts.

According to embodiments of the invention, the steps (a)-(c) are effected under conditions wherein the atmospheric oxygen level is less than about 10%.

According to embodiments of the invention, the method further comprises culturing the differentiated cells in a medium under conditions wherein the atmospheric oxygen level is greater than about 10% in the presence of nicotinamide following step (c).

According to an aspect of some embodiments of the present invention there is provided a pharmaceutical composition comprising the cell population described herein, as the active agent and a pharmaceutically acceptable carrier.

According to an aspect of some embodiments of the present invention there is provided a use of the cell population described herein, for treating a retinal degeneration.

According to an aspect of some embodiments of the present invention there is provided a method of generating RPE cells comprising:

(a) culturing pluripotent stem cells in a medium comprising a differentiating agent so as to generate differentiating cells, wherein the medium is devoid of a member of the transforming growth factor β (TGF β) superfamily;

(b) culturing the differentiating cells in a medium comprising the member of the transforming growth factor β (TGF β) superfamily and the differentiating agent to generate cells which are further differentiated towards the RPE lineage;

(c) culturing the cells which are further differentiated towards the RPE lineage in a medium comprising a differentiating agent so as to generate RPE cells, wherein the medium is devoid of a member of the transforming growth factor β (TGF β) superfamily, wherein steps (a)-(c) are effected under conditions wherein the atmospheric oxygen level is less than about 10%.

According to embodiments of the invention, step (a) is effected under non-adherent conditions.

According to embodiments of the invention, the non-adherent conditions comprise a non-adherent culture plate.

According to embodiments of the invention, the step (a) comprises:

i) culturing the cultured population of human pluripotent stem cells in a medium comprising nicotinamide, in the absence of activin A; under non-adherent conditions to generate a cluster of cells comprising differentiating cells; and subsequently;

ii) culturing the differentiating cells of (i) in a medium comprising nicotinamide, in the absence of activin A under adherent conditions.

According to embodiments of the invention, the method further comprises dissociating the cluster of cells prior to step (ii) to generate clumps of cells or a single cell suspension of cells.

According to embodiments of the invention, the method further comprises culturing the differentiated cells in a medium under conditions wherein the atmospheric oxygen level is greater than about 10% in the presence of a differentiating agent following step (c).

According to embodiments of the invention, the member of the transforming growth factor (TGF β) superfamily is selected from the group consisting of TGFβ1, TGFβ3 and activin A.

According to embodiments of the invention, the differentiating agent of step (a) and the differentiating agent of step (c) are identical.

According to embodiments of the invention, the differentiating agent of step (a) is nicotinamide (NA) or 3-aminobenzamide.

According to embodiments of the invention, the method further comprises selecting polygonal cells following step (c).

According to embodiments of the invention, the method further comprises propagating the polygonal cells.

According to embodiments of the invention, the propagating is effected on an adherent surface or an extracellular matrix.

According to embodiments of the invention, the pluripotent stem cells comprise embryonic stem cells.

According to embodiments of the invention, the embryonic stem cells are propagated in a medium comprising bFGF and TGFβ.

According to embodiments of the invention, the embryonic stem cells are cultured on human cord fibroblasts.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIG. 12: Manufacturing Process, Steps 1-3: Generation of Human Cord Fibroblast Feeder Working Cell Bank.

FIG. 19A), group 5 contra lateral untreated eyes (OD; FIG. 19B) and group 5 treated eyes (OS; FIG. 19C) at P60. The hyper and hypo-pigmented areas in the high dose treated eyes (OS) are presumed to be indicative of transplanted cells.

FIG. 22A illustrates a photomontage of individual images of cresyl violet stained sections of a representative cell treated eye. Between the arrows illustrates the location of photoreceptor protection and presumed location of the grafted cells. FIG. 22B illustrates the comparison between BSS+(Group 2) injected eyes and representative cell injected eyes (multiple dosage groups represented) at post-natal day 60, 100, 150 and 200. GCL: Ganglion Cell Layer; ONL: Outer Nuclear Layer; RPE: Retinal Pigmented Epithelium.

FIG. 25 is a graph illustrating cone quantification following subretinal transplantation of OpRegen® cells into the RCS rat. Cell treated eyes were significantly higher than control eyes at all ages.

FIGS. 26A-J: Immunofluorescent staining of OpRegen® cells in the subretinal space. FIG. 26A represents an area of retina with a number of RPE cells (red, arrows) central and no debris zone (viewed using anti-rat rhodopsin antibody, green; arrow), but where the cells are not (peripheral), the debris zone reconstitutes. At higher magnification (FIG. 26B), some rhodopsin stained outer segments rest along the grafted cells. In addition, the debris zone reconstitutes as distance from transplanted cells increases. FIGS. 26C-J are individual slices through the section showing rhodopsin positive tissue within the transplanted cells (arrows).

FIG. 27A illustrates the ability of OpRegen® cells to engraft in the NOD-SCID subretinal space 9 months post transplant. Pigmented cells stain positive for Human Nuclei and PMEL17. FIG. 27B is a photograph illustrating the clustered cells at the place of the bleb following injection.

FIG. 27C is a photograph illustrating the subsequent spreading of the cells into a monolayer following injection.

FIGS. 32A-C are graphs illustrating ELISA assessment of Angiogenin secretion by OpRegen® cells. A. Increased secretion of angiogenin along Mock V production. B. Secretion of angiogenin by three different batches of OpRegen® cells (Passage 3) and on a transwell for 3 weeks (Passage 4) during which apical and basal secretion was assessed. C. Secretion of angiogenin by RPE7 cells (Passage 3).

DESCRIPTION OF SPECIFIC EMBODIMENTS OF THE INVENTION

Figure 1:
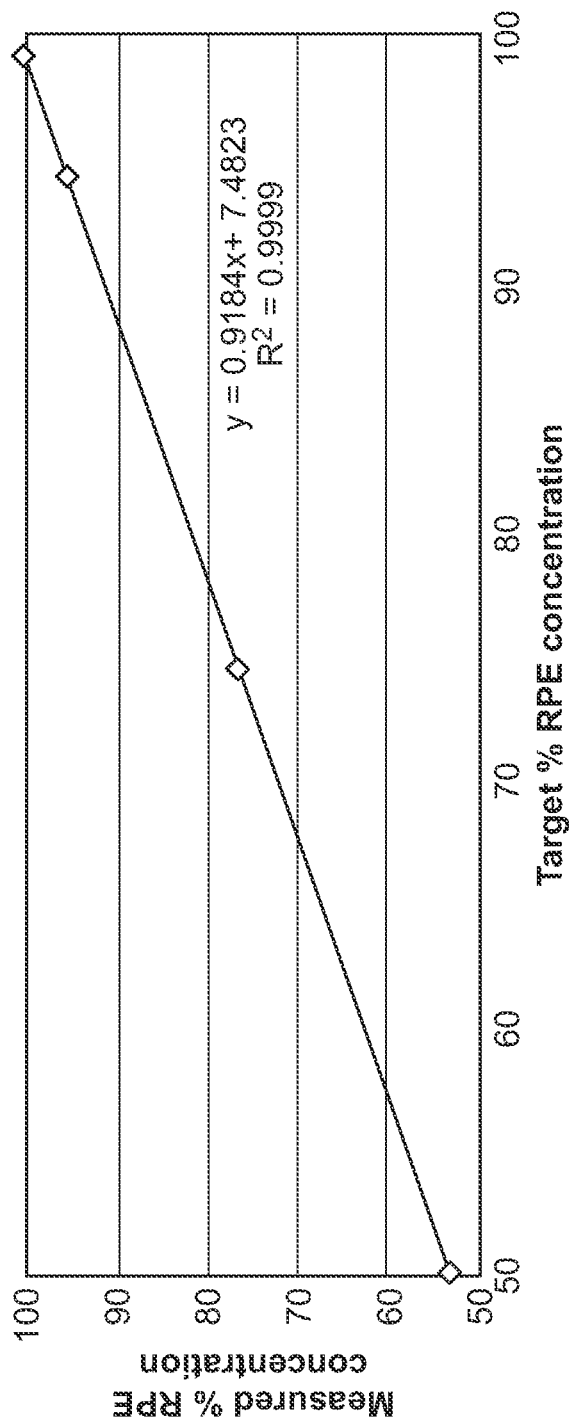
FIG. 1 is a graph illustrating the linearity of the data.

The present invention, in some embodiments thereof, relates to retinal pigment epithelium cells and, more particularly, but not exclusively, to assessment of such cells as a therapeutic. The present invention also relates to generation of retinal pigment epithelium cells from human embryonic stem cells.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

The neural retina initiates vision and is supported by the underlying retinal pigment epithelium (RPE). Dysfunction, degeneration, and loss of RPE cells are prominent features of Best disease, subtypes of retinitis pigmentosa (RP), and age-related macular degeneration (AMD), which is the leading cause of visual disability in the western world. In these conditions, there is progressive visual loss that often leads to blindness.

The retina and adjacent RPE both arise from neural ectoderm. In lower species, RPE regenerates retina but in mammals, RPE-mediated regeneration is inhibited and renewal occurs to a very limited extent via stem cells located at the peripheral retinal margin.

Human embryonic stem cells (hESC) may serve as an unlimited donor source of RPE cells for transplantation. The potential of mouse, primate, and human ESCs to differentiate into RPE-like cells, to attenuate retinal degeneration, and to preserve visual function after subretinal transplantation has been demonstrated.

Various protocols for the differentiation of human embryonic stem cells into RPE cells have been developed (see for example WO 2008/129554).

The present inventors have now discovered a unique and simple way of qualifying cell populations which have been successfully differentiated into RPE cells based on expression of particular polypeptides. Of the myriad of potential polypeptides expressed on these differentiated cells, the present inventors have found that a combination of two particular markers can be used to substantiate successful differentiation.

The present inventors have also discovered that secretion of Pigment epithelium-derived factor (PEDF) may be used as a marker to substantiate early stages of the RPE differentiation process (see Table 4).

Whilst further reducing the present invention to practice, the present inventors identified additional proteins which are secreted by RPE cells which may be used, in some embodiments, as a signature to define the cells.

Thus, according to one aspect of the present invention there is provided a method of qualifying whether a cell population is a suitable therapeutic for treating an eye condition, comprising analyzing co-expression of premelano some protein (PMEL 17) and at least one polypeptide selected from the group consisting of cellular retinaldehyde binding protein (CRALBP), lecithin retinol acyltransferase (LRAT) and sex determining region Y-box 9 (SOX9) in the population of cells, wherein when the number of cells that coexpress the PMEL17 and the at least one polypeptide is above a predetermined level, the cell population is qualified as being a suitable therapeutic for treating a retinal disorder.

According to another aspect, there is provided a method of qualifying whether a cell population is a suitable therapeutic for treating an eye condition, comprising analyzing co-expression of cellular retinaldehyde binding protein (CRALBP) and at least one polypeptide selected from the group consisting of premelanosome protein (PMEL17), lecithin retinol acyltransferase (LRAT) and sex determining region Y-box 9 (SOX9) in the population of cells, wherein when the number of cells that co-express the CRALBP and the at least one polypeptide is above a predetermined level, the cell population is qualified as being a suitable therapeutic for treating an eye condition.

As used herein, the phrase "suitable therapeutic" refers to the suitability of the cell population for treating eye conditions. Cells which are therapeutic may exert their effect through any one of a multiple mechanisms. One exemplary mechanism is trophic supportive effect promoting the survival of degenerating photoreceptors or other cells within the retina. Therapeutic RPE cells may also exert their effect through a regeneration mechanism replenishing mal-functioning and/or degenerating host RPE cells. According to one embodiment, the RPE cells are mature and have the functional capability of phagocytosing outer shedded segments of photoreceptors which include rhodopsin. According to another embodiment, the RPE cells are not fully mature.

Eye conditions for which the cell populations serve as therapeutics include, but are not limited to retinal diseases or disorders generally associated with retinal dysfunction, retinal injury, and/or loss of retinal pigment epithelium. A non-limiting list of conditions which may be treated in accordance with the invention comprises retinitis pigmentosa, lebers congenital amaurosis, hereditary or acquired macular degeneration, age related macular degeneration (AMD), Best disease, retinal detachment, gyrate atrophy, choroideremia, pattern dystrophy as well as other dystrophies of the RPE, Stargardt disease, RPE and retinal damage due to damage caused by any one of photic, laser, inflammatory, infectious, radiation, neo vascular or traumatic injury.

As mentioned, the method of this aspect of the invention is carried out by measuring the amount (e.g. percent cells) expressing premelanosome protein (PMEL17; SwissProt No. P40967) and at least one polypeptide selected from the group consisting of cellular retinaldehyde binding protein (CRALBP; SwissProt No. P12271), lecithin retinol acyltransferase (LRAT; SwissProt No. O95327) and sex determining region Y-box 9 (SOX9; P48436).

Alternatively, the method of this aspect is carried out by measuring CRALBP (CRALBP; SwissProt No. P12271) and at least one polypeptide selected from the group consisting of lecithin retinol acyltransferase (LRAT; SwissProt No. O95327), sex determining region Y-box 9 (SOX9; P48436) and PMEL17 (SwissProt No. P40967).

Thus, for example, CRALBP and PMEL17 may be measured; PMEL17 and LRAT may be measured, or PMEL17 and SOX9 may be measured. Alternatively, CRALBP and LRAT may be measured, or CRALBP and SOX9 may be measured.

It will be appreciated that more than two of the polypeptides mentioned herein can be measured, for example three of the above mentioned polypeptides or even all four of the above mentioned polypeptides.

Methods for analyzing for expression of the above mentioned polypeptides typically involve the use of antibodies which specifically recognize the antigen. Commercially available antibodies that recognize CRALBP include for example those manufactured by Abcam (e.g. ab15051 and ab189329, clone B2). Commercially available antibodies that recognize PMEL17 include for example those manufactured by Abcam (e.g. ab137062 and ab189330, clone EPR4864). Commercially available antibodies that recognize LRAT include for example those manufactured by Millipore (e.g. MABN644). Commercially available antibodies that recognize SOX9 include for example those manufactured by Abcam (e.g. ab185230). The analyzing may be carried out using any method known in the art including flow cytometry, Western Blot, immunocytochemistry, radioimmunoassay, PCR, etc.

For flow cytometry, the antibody may be attached to a fluorescent moiety and analyzed using a fluorescence-activated cell sorter (FACS). Alternatively, the use of secondary antibodies with fluorescent moieties is envisioned.

It will be appreciated that since the polypeptides which are analyzed are intracellular polypeptides, typically the cells are permeabilized so that the antibodies are capable of binding to their targets. Cells may be fixed first to ensure stability of soluble antigens or antigens with a short half-life. This should retain the target protein in the original cellular location. Antibodies may be prepared in permeabilization buffer to ensure the cells remain permeable. It will be appreciated that when gating on cell populations, the light scatter profiles of the cells on the flow cytometer will change considerably after permeabilization and fixation.

Methods of permeabilizing the cell membrane are known in the art and include for example:
1. Formaldehyde followed by detergent: Fixation in formaldehyde (e.g. no more than 4.5% for 10-15 min (this will stabilize proteins), followed by disruption of membrane by detergent such as Triton or NP-40 (0.1 to 1% in PBS), Tween 20 (0.1 to 1% in PBS), Saponin, Digitonin and Leucoperm (e.g. 0.5% v/v in PBS);
2. Formaldehyde (e.g. no more than 4.5%) followed by methanol;
3. Methanol followed by detergent (e.g. 80% methanol and then 0.1% Tween 20);
4. Acetone fixation and permeabilization.

As used herein, the term "flow cytometry" refers to an assay in which the proportion of a material (e.g. RPE cells comprising a particular marker) in a sample is determined by labeling the material (e.g., by binding a labeled antibody to the material), causing a fluid stream containing the material to pass through a beam of light, separating the light emitted from the sample into constituent wavelengths by a series of filters and mirrors, and detecting the light.

A multitude of flow cytometers are commercially available including for e.g. Becton Dickinson FACScan, Navios Flow Cytometer (Beckman Coulter serial #AT15119 RHE9266 and FACScalibur (BD Biosciences, Mountain View, CA). Antibodies that may be used for FACS analysis are taught in Schlossman S, Boumell L, et al., [Leucocyte Typing V. New York: Oxford University Press; 1995] and are widely commercially available.

It will be appreciated that the expression level of the above mentioned polypeptides may be effected on the RNA level as well as the protein level. Exemplary methods for determining the expression of a polypeptide based on the RNA level include but are not limited to PCR, RT-PCR, Northern Blot etc.

In order to qualify that the cells are useful as a therapeutic, the amount of at least two of the polypeptides co-expressed in the cells should be increased above a statistically significant level as compared to non-RPE cells (e.g. non-differentiated embryonic stem cells).

According to a particular embodiment, in order to qualify that the cells are useful as a therapeutic, at least 80% of the cells of the population should express detectable levels of PMEL17 and one of the above mentioned polypeptides (e.g. CRALBP), more preferably at least 85% of the cells of the population should express detectable levels of PMEL17 and one of the above mentioned polypeptides (e.g. CRALBP), more preferably at least 90% of the cells of the population should express detectable levels of PMEL17 and one of the above mentioned polypeptides (e.g. CRALBP), more preferably at least 95% of the cells of the population should express detectable levels of PMEL17 and one of the above mentioned polypeptides (e.g. CRALBP), more preferably 100% of the cells of the population should express detectable levels of PMEL17 and one of the above mentioned polypeptides (e.g. CRALBP as assayed by a method known to those of skill in the art (e.g. FACS).

According to another embodiment, in order to qualify that the cells are useful as a therapeutic, the level of CRALBP and one of the above mentioned polypeptides (e.g. PMEL17) coexpression (e.g. as measured by the mean fluorescent intensity) should be increased by at least two fold, more preferably at least 3 fold, more preferably at least 4 fold and even more preferably by at least 5 fold, at least 10 fold, at least 20 fold, at least 30 fold, at least 40 fold, at least 50 as compared to non-differentiated ESCs.

According to a particular embodiment, in order to qualify that the cells are useful as a therapeutic, at least 80% of the cells of the population should express detectable levels of CRALBP and one of the above mentioned polypeptides (e.g. PMEL17), more preferably at least 85% of the cells of the population should express detectable levels of CRALBP and one of the above mentioned polypeptides (e.g. PMEL17), more preferably at least 90% of the cells of the population should express detectable levels of CRALBP and one of the above mentioned polypeptides (e.g. PMEL17), more preferably at least 95% of the cells of the population should express detectable levels of CRALBP and one of the above mentioned polypeptides (e.g. PMEL17), more preferably 100% of the cells of the population should express detectable levels of CRALBP and one of the above mentioned polypeptides (e.g. PMEL17 as assayed by a method known to those of skill in the art (e.g. FACS).

In addition, the cell may be qualified in vivo in animal models. One such model is the Royal College of Surgeons (RCS) rat model. Following transplantation, the therapeutic effect of the cells may be analyzed using methods which include fundus imaging, optokinetic tracking thresholds (OKT), electroretinogram (ERG), histology, cone counting and rhodopsin ingestion. These methods are further described in Example 5, herein below.

The cells may be qualified or characterized in additional ways including for example karyotype analysis, morphology, cell number and viability, potency (barrier function and polarized secretion of PEDF and VEGF), level of residual hESCs, gram staining and sterility. Exemplary assays which may be performed are described in Example 4.

In addition, the cells may be analyzed for barrier function and their level of growth factor secretion in a polarized manner (e.g. Pigment epithelium-derived factor (PEDF) or VEGF, cytokines, interleukins and/or chemokines).

For analysis of secreted PEDF, supernatant is collected from cultures of the cells, and cells are harvested and counted. The amount of PEDF in the cell's culture supernatants may be quantified by using a PEDF ELISA assay (such as ELISAquant™ PEDF Sandwich ELISA Antigen Detection Kit, BioProductsMD, PED613) according to the manufacturer's protocol.

Figure 28:
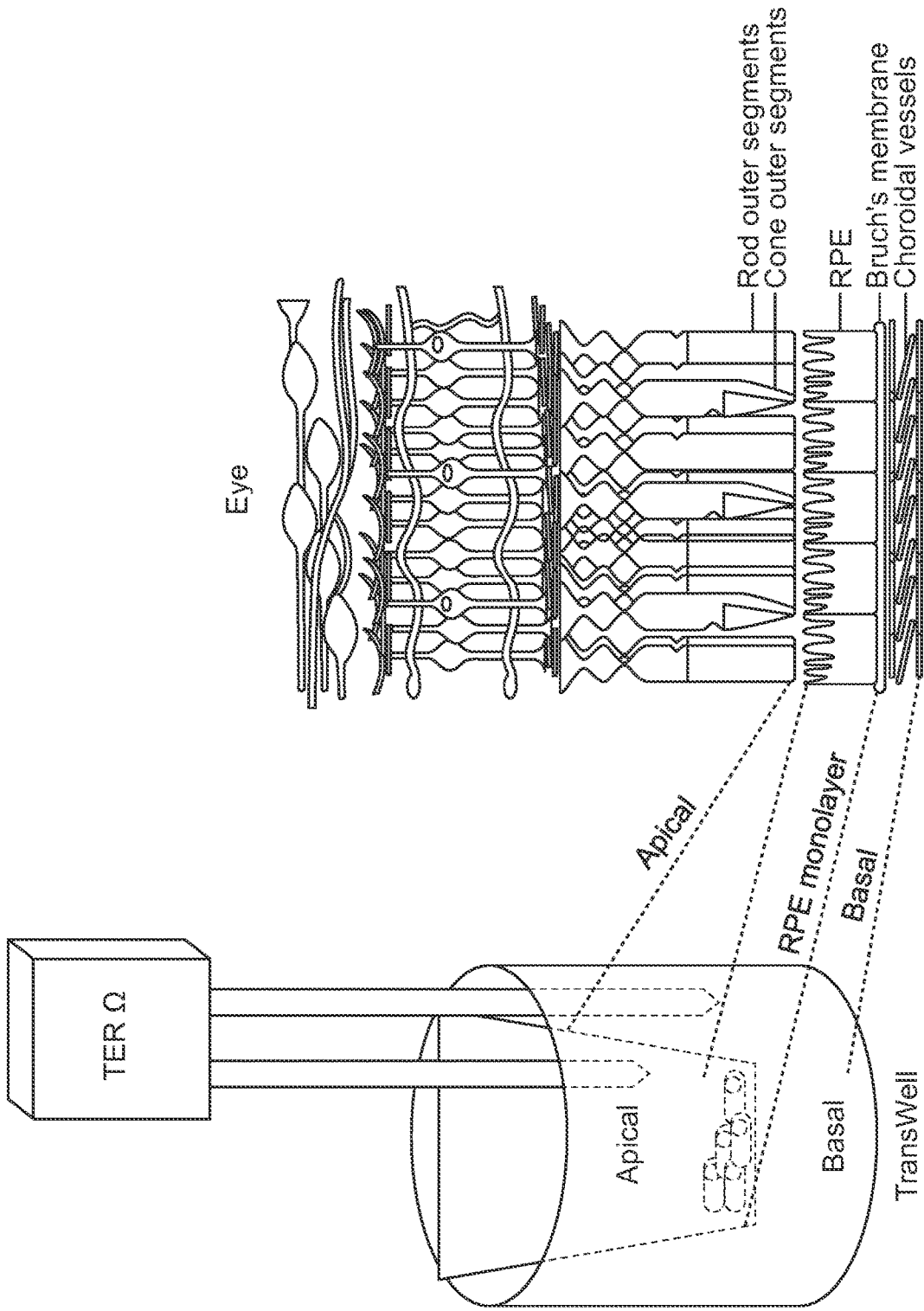
FIG. 28 is a pictorial illustration of a transwell assay that may be used to assay the potency of RPE cells.

In addition, the direction of secretion of PEDF and VEGF may be analyzed in the cells. This may be effected using a transwell assay as illustrated in FIG. 28. Prior to or following qualification, the cells may be preserved according to methods known in the art (e.g. frozen or cryopreserved) or may be directly administered to the subject.

The present invention contemplates analyzing cell populations which comprise retinal pigment epithelial (RPE) cells from any source. Thus, the cell populations may comprise RPE cells obtained from a donor (i.e. native RPE cells of the pigmented layer of the retina) or may comprise RPE cells which were ex-vivo differentiated from a population of stem cells (hSC-derived RPE cells, such as pluripotent stem cells—e.g. human embryonic stem cells). According to another embodiment, the RPE cells are obtained by transdifferentiation—see for example Zhang et al., Protein Cell 2014, 5(1):48-58, the contents of which are incorporated herein by reference.

According to one embodiment, the RPE cells that are analyzed do not express Pax6.

According to another embodiment, the RPE cells that are analyzed express Pax6.

"Retinal pigment epithelium cells", "RPE cells", "RPEs", which may be used interchangeably as the context allows, refers to cells of a cell type functionally similar to that of native RPE cells which form the pigment epithelium cell layer of the retina (e.g. upon transplantation within an eye, they exhibit functional activities similar to those of native RPE cells).

According to one embodiment, the RPE cell expresses at least one, two, three, four or five markers of mature RPE cells. Such markers include, but are not limited to CARLBP, RPE65, PEDF, PMEL17, Bestrophin and tyrosinase. Optionally, RPE cells may also express a marker of an RPE progenitor—e.g. MITF. In another embodiment, the RPE cells express PAX-6. In another embodiment, the RPE cells express at least one marker of a retinal progenitor cell including, but not limited to OTX2, SIX3, SIX6 and LHX2.

According to yet another embodiment, the RPE cells are those that are differentiated from embryonic stem cells according to the method described in the Examples section herein below, the contents of the Examples being as if included in the specification itself.

As used herein, the phrase "markers of mature RPE cells" refers to antigens (e.g. proteins) that are elevated (e.g. at least 2 fold, at least 5 fold, at least 10 fold) in mature RPE cells with respect to non RPE cells or immature RPE cells.

As used herein the phrase "markers of RPE progenitor cells" refers to antigens (e.g. proteins) that are elevated (e.g. at least 2 fold, at least 5 fold, at least 10 fold) in RPE progenitor cells with respect to non RPE cells.

According to another embodiment, the RPE cells have a morphology similar to that of native RPE cells which form the pigment epithelium cell layer of the retina i.e. pigmented and/or have a characteristic polygonal shape.

According to still another embodiment, the RPE cells are capable of treating diseases such as macular degeneration.

According to still another embodiment, the RPE cells fulfill at least 1, 2, 3, 4 or all of the requirements listed herein above.

The term "hSC-derived RPE cells" is used herein to denote RPE cells that are obtained by directed differentiation from hSCs. In accordance with a preferred embodiment, the hSC-derived RPE cells are functional RPE cells as exhibited by parameters defined hereinbelow. The term "directed differentiation" is used interchangeably with the term "RPE induced differentiation" and is to be understood as meaning the process of manipulating hSCs under culture conditions which induce/promote differentiation into RPE cell type.

According to a particular embodiment, the RPE cells are obtained by directed differentiation of hSCs in the presence of one or more members of the TGFβ superfamily, and exhibit at least one of the following characteristics:

during differentiation, the cultured cells respond to TGFβ signaling;

the RPE cells express markers indicative of terminal differentiation, e.g. bestrophin 1, CRALBP and/or RPE65;

following transplantation (i.e. in situ), the RPE cells exhibit trophic effect supporting photoreceptors adjacent to RPE cells;

further, in situ the RPE cells are capable of functioning with phagocytosis of shed photoreceptor outer segments as part of the normal renewal process of these photoreceptors;

further, in situ the RPE cells are capable of generating a retinal barrier and functioning in the visual cycle.

As used herein, the phrase "stem cells" refers to cells which are capable of remaining in an undifferentiated state (e.g., pluripotent or multipotent stem cells) for extended periods of time in culture until induced to differentiate into other cell types having a particular, specialized function (e.g., fully differentiated cells). Preferably, the phrase "stem cells" encompasses embryonic stem cells (ESCs), induced pluripotent stem cells (iPS), adult stem cells, mesenchymal stem cells and hematopoietic stem cells.

According to a particular embodiment, the RPE cells are derived from pluripotent stem cells including human embryonic stem cells or induced pluripotent stem cells.

The phrase "embryonic stem cells" refers to embryonic cells which are capable of differentiating into cells of all three embryonic germ layers (i.e., endoderm, ectoderm and mesoderm), or remaining in an undifferentiated state. The phrase "embryonic stem cells" may comprise cells which are obtained from the embryonic tissue formed after gestation (e.g., blastocyst) before implantation of the embryo (i.e., a pre-implantation blastocyst), extended blastocyst cells (EBCs) which are obtained from a post-implantation/pre-gastrulation stage blastocyst (see WO2006/040763) and embryonic germ (EG) cells which are obtained from the genital tissue of a fetus any time during gestation, preferably before 10 weeks of gestation. The embryonic stem cells of some embodiments of the invention can be obtained using well-known cell-culture methods. For example, human embryonic stem cells can be isolated from human blastocysts. Human blastocysts are typically obtained from human in vivo preimplantation embryos or from in vitro fertilized (IVF) embryos. Alternatively, a single cell human embryo can be expanded to the blastocyst stage. For the isolation of human ES cells, the zona pellucida is removed from the blastocyst and the inner cell mass (ICM) is isolated by surgery, in which the trophectoderm cells are lysed and removed from the intact ICM by gentle pipetting. The ICM is then plated in a tissue culture flask containing the appropriate medium which enables its outgrowth. Following 9 to 15 days, the ICM derived outgrowth is dissociated into clumps either by a mechanical dissociation or by an enzymatic degradation and the cells are then re-plated on a fresh tissue culture medium. Colonies demonstrating undifferentiated morphology are individually selected by micropipette/stem cell tool, mechanically dissected into fragments/clumps, and re-plated. Resulting ES cells are then routinely split every 4-7 days. For further details on methods of preparation human ES cells see Reubinoff et al., Nat Biotechnol 2000, May: 18(5): 559; Thomson et al., [U.S. Pat. No. 5,843,780; Science 282: 1145, 1998; Curr. Top. Dev. Biol. 38: 133, 1998; Proc. Natl. Acad. Sci. USA 92: 7844, 1995]; Bongso et al., [Hum Reprod 4: 706, 1989]; and Gardner et al., [Fertil. Steril. 69: 84, 1998].

It will be appreciated that commercially available stem cells can also be used according to some embodiments of the invention. Human ES cells can be purchased from the NIH human embryonic stem cells registry [Hypertext Transfer Protocol://grants(dot)nih(dot)gov/stem_cells/registry/current(dot)htm] and other European registries. Non-limiting examples of commercially available embryonic stem cell lines are HAD-C102, ESI, BG01, BG02, BG03, BG04, CY12, CY30, CY92, CY10, TE03, TE32, CHB-4, CHB-5, CHB-6, CHB-8, CHB-9, CHB-10, CHB-11, CHB-12, HUES 1, HUES 2, HUES 3, HUES 4, HUES 5, HUES 6, HUES 7, HUES 8, HUES 9, HUES 10, HUES 11, HUES 12, HUES 13, HUES 14, HUES 15, HUES 16, HUES 17, HUES 18, HUES 19, HUES 20, HUES 21, HUES 22, HUES 23, HUES 24, HUES 25, HUES 26, HUES 27, HUES 28, CyT49, RUES3, WA01, UCSF4, NYUES1, NYUES2, NYUES3, NYUES4, NYUES5, NYUES6, NYUES7, UCLA 1, UCLA 2, UCLA 3, WA077 (H7), WA09 (H9), WA13 (H13), WA14 (H14), HUES 62, HUES 63, HUES 64, CT1, CT2, CT3, CT4, MA135, Eneavour-2, WIBR1, WIBR2, WIBR3, WIBR4, WIBR5, WIBR6, HUES 45, Shef 3, Shef 6, BJNhem19, BJNhem20, SA001, SA001.

In addition, ES cells can be obtained from other species as well, including mouse (Mills and Bradley, 2001), golden hamster [Doetschman et al., 1988, Dev Biol. 127: 224-7], rat [Iannaccone et al., 1994, Dev Biol. 163: 288-92] rabbit [Giles et al. 1993, Mol Reprod Dev. 36: 130-8; Graves & Moreadith, 1993, Mol Reprod Dev. 1993, 36: 424-33], several domestic animal species [Notarianni et al., 1991, J Reprod Fertil Suppl. 43: 255-60; Wheeler 1994, Reprod Fertil Dev. 6: 563-8; Mitalipova et al., 2001, Cloning. 3: 59-67] and non-human primate species (Rhesus monkey and marmoset) [Thomson et al., 1995, Proc Natl Acad Sci USA. 92: 7844-8; Thomson et al., 1996, Biol Reprod. 55: 254-9].

Extended blastocyst cells (EBCs) can be obtained from a blastocyst of at least nine days post fertilization at a stage prior to gastrulation. Prior to culturing the blastocyst, the zona pellucida is digested [for example by Tyrode's acidic solution (Sigma Aldrich, St Louis, MO, USA)] so as to expose the inner cell mass. The blastocysts are then cultured as whole embryos for at least nine and no more than fourteen days post fertilization (i.e., prior to the gastrulation event) in vitro using standard embryonic stem cell culturing methods.

Another method for preparing ES cells is described in Chung et al., Cell Stem Cell, Volume 2, Issue 2, 113-117, 7 Feb. 2008. This method comprises removing a single cell from an embryo during an in vitro fertilization process. The embryo is not destroyed in this process.

Yet another method for preparing ES cells is by parthenogenesis. The embryo is also not destroyed in the process.

Currently practiced ES culturing methods are mainly based on the use of feeder cell layers which secrete factors needed for stem cell proliferation, while at the same time, inhibit their differentiation. Exemplary feeder layers include Human embryonic fibroblasts, adult fallopian epithelial cells, primary mouse embryonic fibroblasts (PMEF), mouse embryonic fibroblasts (MEF), murine fetal fibroblasts (MFF), human embryonic fibroblast (HEF), human fibroblasts obtained from the differentiation of human embryonic stem cells, human fetal muscle cells (HFM), human fetal skin cells (HFS), human adult skin cells, human foreskin fibroblasts (HFF), human umbilical cord fibroblasts, human cells obtained from the umbilical cord or placenta, and human marrow stromal cells (hMSCs). Growth factors may be added to the medium to maintain the ESCs in an undifferentiated state. Such growth factors include bFGF and/or TGFβ. In another embodiment, agents may be added to the medium to maintain the hESCs in a naïve undifferentiated state—see for example Kalkan et al., 2014, Phil. Trans. R. Soc. B, 369: 20130540.

Feeder cell free systems have also been used in ES cell culturing, such systems utilize matrices supplemented with serum replacement, cytokines and growth factors (including IL6 and soluble IL6 receptor chimera) as a replacement for the feeder cell layer. Stem cells can be grown on a solid surface such as an extracellular matrix (e.g., Matrigel® or laminin) in the presence of a culture medium—for example the Lonza L7 system, mTeSR, StemPro, XFKSR, E8). Unlike feeder-based cultures which require the simultaneous growth of feeder cells and stem cells and which may result in mixed cell populations, stem cells grown on feeder-free systems are easily separated from the surface. The culture medium used for growing the stem cells contains factors that effectively inhibit differentiation and promote their growth such as MEF-conditioned medium and bFGF. However, commonly used feeder-free culturing systems utilize an animal-based matrix (e.g., Matrigel®) supplemented with mouse or bovine serum, or with MEF conditioned medium [Xu C, et al. (2001). Feeder-free growth of undifferentiated human embryonic stem cells. Nat Biotechnol. 19: 971-4] which present the risk of animal pathogen cross-transfer to the human ES cells, thus compromising future clinical applications.

Numerous methods are known for differentiating ESCs towards the RPE lineage and include both directed differentiation protocols such as those described in WO 2008/129554, 2013/184809 and spontaneous differentiation protocols such as those described in U.S. Pat. No. 8,268,303 and U.S. Patent application 20130196369, the contents of each being incorporated by reference.

According to a particular embodiment, the RPE cells are generated from ESC cells using a directed differentiation protocol—for example according to that disclosed in the Example section.

In one exemplary differentiation protocol, the embryonic stem cells are differentiated towards the RPE cell lineage using a first differentiating agent and then further differentiated towards RPE cells using a member of the transforming growth factor-β (TGFβ) superfamily, (e.g. TGFβ1, TGFβ2, and TGFβ3 subtypes, as well as homologous ligands including activin (e.g., activin A, activin B, and activin AB), nodal, anti-mullerian hormone (AMH), some bone morphogenetic proteins (BMP), e.g. BMP2, BMP3, BMP4, BMP5, BMP6, and BMP7, and growth and differentiation factors (GDF)).

According to a particular embodiment, the TGFβ superfamily member is selected from the group consisting of TGFβ1, activin A and TGFβ3.

According to a specific embodiment, the member of the transforming growth factor-β (TGFβ) superfamily is activin A—e.g. between 20-200 ng/ml, e.g. 100-180 ng/ml.

The first differentiating agent promotes differentiation towards the RPE lineage. For example, the first differentiating agent may promote differentiation of the pluripotent stem cells into neural progenitors. Such cells may express neural precursor markers such as PAX6.

According to a particular embodiment, the first differentiating agent is nicotinamide (NA)—e.g. between 1-100 mM, 5-50 mM, 5-20 mM, e.g. 10 mM.

NA, also known as "niacinamide", is the amide derivative form of Vitamin B3 (niacin) which is thought to preserve and improve beta cell function. NA has the chemical formula $C_6H_6N_2O$. NA is essential for growth and the conversion of foods to energy, and it has been used in arthritis treatment and diabetes treatment and prevention.

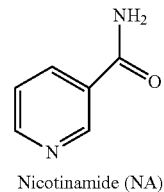

Nicotinamide (NA)

According to a particular embodiment, the nicotinamide is a nicotinamide derivative or a nicotinamide mimic. The term "derivative of nicotinamide (NA)" as used herein denotes a compound which is a chemically modified derivative of the natural NA. In one embodiment, the chemical modification may be a substitution of the pyridine ring of the basic NA structure (via the carbon or nitrogen member of the ring), via the nitrogen or the oxygen atoms of the amide moiety. When substituted, one or more hydrogen atoms may be replaced by a substituent and/or a substituent may be attached to a N atom to form a tetravalent positively charged nitrogen. Thus, the nicotinamide of the present invention includes a substituted or non-substituted nicotinamide. In another embodiment, the chemical modification may be a deletion or replacement of a single group, e.g. to form a thiobenzamide analog of NA, all of which being as appreciated by those versed in organic chemistry. The derivative in the context of the invention also includes the nucleoside derivative of NA (e.g. nicotinamide adenine).

A variety of derivatives of NA are described, some also in connection with an inhibitory activity of the PDE4 enzyme (WO03/068233; WO02/060875; GB2327675A), or as VEGF-receptor tyrosine kinase inhibitors (WO01/55114). For example, the process of preparing 4-aryl-nicotinamide derivatives (WO05/014549). Other exemplary nicotinamide derivatives are disclosed in WO01/55114 and EP2128244.

Nicotinamide mimics include modified forms of nicotinamide, and chemical analogs of nicotinamide which recapitulate the effects of nicotinamide in the differentiation and maturation of RPE cells from pluripotent cells. Exemplary nicotinamide mimics include benzoic acid, 3-aminobenzoic acid, and 6-aminonicotinamide. Another class of compounds that may act as nicotinamide mimics are inhibitors of poly(ADP-ribose) polymerase (PARP). Exemplary PARP inhibitors include 3-aminobenzamide, Iniparib (BSI 201), Olaparib (AZD-2281), Rucaparib (AG014699, PF-01367338), Veliparib (ABT-888), CEP 9722, MK 4827, and BMN-673.

According to a particular embodiment, the differentiation is effected as follows:

a) culture of ESCs in a medium comprising a first differentiating agent (e.g. nicotinamide); and b) culture of cells obtained from step a) in a medium comprising a member of the TGFβ superfamily (e.g. activin A) and the first differentiating agent (e.g. nicotinamide).

Preferably step (a) is effected in the absence of the member of the TGFβ superfamily.

The above described protocol may be continued by culturing the cells obtained in step (b) in a medium comprising the first differentiating agent (e.g. nicotinamide), but devoid of a member of the TGFβ superfamily (e.g. activin A). This step is referred to herein as step (c).

The above described protocol is now described in further detail, with additional embodiments.

The differentiation process is started once sufficient quantities of ESCs are obtained. They are typically removed from the adherent cell culture (e.g. by using collagenase A, dispase, TrypLE select, EDTA) and plated onto a non-adherent substrate (e.g. Hydrocell non-adherent cell culture plate) in the presence of nicotinamide (and the absence of activin A). Exemplary concentrations of nicotinamide are between 1-100 mM, 5-50 mM, 5-20 mM, e.g. 10 mM. Once the cells are plated onto the non-adherent substrate, the cell culture may be referred to as a cell suspension, preferably free floating clusters in a suspension culture, i.e. aggregates of cells derived from human embryonic stem cells (hESCs). The cell clusters do not adhere to any substrate (e.g. culture plate, carrier). Sources of free floating stem cells were previously described in WO 06/070370, which is herein incorporated by reference in its entirety. This stage may be effected for a minimum of 1 day, more preferably two days, three days, 1 week or even 10 days. Preferably, the cells are not cultured for more than 2 weeks in suspension together with the nicotinamide (and in the absence of the TGFβ superfamily member e.g. activin A).

According to a preferred embodiment, when the cells are cultured on the non-adherent substrate, the atmospheric oxygen conditions are manipulated such that the percentage is equal or less than about 20%, 15%, 10%, more preferably less than about 9%, less than about 8%, less than about 7%, less than about 6% and more preferably about 5% (e.g. between 1%-20%, 1%-10% or 0-5%).

Examples of non-adherent cell culture plates include those manufactured by Hydrocell (e.g. Cat No. 174912), Nunc etc.

Typically, the clusters comprise at least 50-500,000, 50-100,000, 50-50,000, 50-10,000, 50-5000, 50-1000 cells. According to one embodiment, the cells in the clusters are not organized into layers and form irregular shapes. In one embodiment, the clusters are devoid of pluripotent embryonic stem cells. In another embodiment, the clusters comprise small amounts of pluripotent embryonic stem cells (e.g. no more than 5%, or no more than 3% (e.g. 0.01-2.7%) cells that co-express OCT4 and TRA 1-60 at the protein level). Typically, the clusters comprise cells that have been partially differentiated under the influence of nicotinamide. Such cells may express neural precursor markers such as PAX6. The cells may also express markers of progenitors of other lineages such as for example alpha-feto protein, MIXL1 and Brachyuri.

The clusters may be dissociated using enzymatic or non-enzymatic methods (e.g., mechanical) known in the art. According to one embodiment, the cells are dissociated such that they are no longer in clusters—e.g. aggregates or clumps of 2-100,000 cells, 2-50,000 cells, 2-10,000 cells, 2-5000 cells, 2-1000 cells, 2-500 cells, 2-100 cells, 2-50 cells. According to a particular embodiment, the cells are in a single cell suspension.

The cells (e.g. dissociated cells) are then plated on an adherent substrate and cultured in the presence of nicotinamide e.g. between 1-100 mM, 5-50 mM, 5-20 mM, e.g. 10 mM (and the absence of activin A). This stage may be effected for a minimum of 1 day, more preferably two days, three days, 1 week or even 14 days. Preferably, the cells are not cultured for more than 1 week in the presence of nicotinamide on the adherent cell culture (and in the absence of activin).

Altogether, the cells are typically exposed to nicotinamide, (at concentrations between 1-100 mM, 5-50 mM, 5-20 mM, e.g. 10 mM), for about 2-3 weeks, and preferably not more than 4 weeks prior to the addition of the second differentiating factor (e.g. Activin A).

Examples of adherent substrates include but are not limited to collagen, fibronectin, laminin, (e.g. laminin 521).

Following the first stage of directed differentiation (i.e. culture in the presence of nicotinamide (e.g. 10 mM) under non-adherent culture conditions under low oxygen atmospheric conditions followed by culturing on an adherent substrate in the presence of nicotinamide under low oxygen atmospheric conditions), the semi-differentiated cells are then subjected to a further stage of differentiation on the adherent substrate—culturing in the presence of nicotinamide (e.g. 10 mM) and activin A (e.g. 20-200 ng/ml, 100-200 ng/ml, e.g. 140 ng/ml, 150 ng/ml, 160 ng/ml or 180 ng/ml). This stage may be effected for 1 day to 10 weeks, 3 days to 10 weeks, 1 week to 10 weeks, one week to eight weeks, one week to four weeks, for example for at least one week, at least two weeks, at least three weeks, at least four weeks, at least five weeks, at least six weeks, at least seven weeks or even eight weeks. Preferably this stage is effected for about two weeks. According to one embodiment, this stage of differentiation is also effected at low atmospheric oxygen conditions—i.e. less than about 20%, 15%, 10%, more preferably less than about 9%, less than about 8%, less than about 7%, less than about 6% and more preferably about 5% (e.g. between 1-20%, 1%-10% or 0-5%).

Following the second stage of directed differentiation (i.e. culture in the presence of nicotinamide and activin A on an adherent substrate), the further differentiated cells may optionally be subjected to a subsequent stage of differentiation on the adherent substrate—culturing in the presence of nicotinamide (e.g. between 1-100 mM, 5-50 mM, 5-20 mM, e.g. 10 mM), in the absence of activin A. This stage may be effected for at least one day, 2 days, 3 days, 1 week, at least two weeks, at least three weeks or even four weeks. Preferably this stage is effected for about one week. This stage of differentiation may be effected at low (i.e. less than about 20%, 15%, 10%, more preferably less than about 9%, less than about 8%, less than about 7%, less than about 6% and more preferably about 5% (e.g. between 1%-20%, 1%-10% or 0-5%) or normal atmospheric oxygen conditions or a combination of both (i.e. initially at low atmospheric oxygen conditions and subsequently when lightly pigmented cells are observed, at normal oxygen conditions).

According to a particular embodiment, when the atmospheric oxygen conditions are returned to normal atmospheric conditions the cells are cultured for at least one more day (e.g. up to two weeks) in the presence of nicotinamide (e.g. 10 mM) and in the absence of activin A.

The basic medium in accordance with the invention is any known cell culture medium known in the art for supporting cells growth in vitro, typically, a medium comprising a defined base solution, which includes salts, sugars, amino acids and any other nutrients required for the maintenance of the cells in the culture in a viable state. Non-limiting examples of commercially available basic media that may be utilized in accordance with the invention comprise Nuristem (without bFGF and TGF3 for ESC differentiation, with bFGF and TGFβ for ESC expansion) Neurobasal™, KO-DMEM, DMEM, DMEM/F12, Lonza L7 system, mTeSR, StemPro, XF KSR, E8, Cellgro™ Stem Cell Growth Medium, or X-Vivo™. The basic medium may be supplemented with a variety of agents as known in the art dealing with cell cultures. The following is a non-limiting reference to various supplements that may be included in the culture system to be used in accordance with the present disclosure:

serum or with a serum replacement containing medium, such as, without being limited thereto, knock out serum replacement (KOSR), Nutridoma-CS, TCH™, N2, N2 derivative, or B27 or a combination;

an extracellular matrix (ECM) component, such as, without being limited thereto, fibronectin, laminin, collagen and gelatin. The ECM may them be used to carry the one or more members of the TGFβ superfamily of growth factors;

an antibacterial agent, such as, without being limited thereto, penicillin and streptomycin;

non-essential amino acids (NEAA), neurotrophins which are known to play a role in promoting the survival of SCs in culture, such as, without being limited thereto, BDNF, NT3, NT4.

According to a preferred embodiment, the medium used for differentiating the ESCs is Nuristem medium (Biological Industries, 05-102-1A or 05-100-1A).

According to a particular embodiment, differentiation of ESCs is effected under xeno free conditions.

According to one embodiment, the proliferation/growth medium is devoid of xeno contaminants i.e. free of animal derived components such as serum, animal derived growth factors and albumin. Thus, according to this embodiment, the culturing is performed in the absence of xeno contaminants.

Other methods for culturing ESCs under xeno free conditions are provided in U.S. Patent Application Publication No. 20130196369, the contents of which are incorporated in their entirety.

During differentiation steps, the embryonic stem cells may be monitored for their differentiation state. Cell differentiation can be determined upon examination of cell or tissue-specific markers which are known to be indicative of differentiation.

Tissue/cell specific markers can be detected using immunological techniques well known in the art [Thomson J A et al., (1998). Science 282: 1145-7]. Examples include, but are not limited to, flow cytometry for membrane-bound or intracellular markers, immunohistochemistry for extracellular and intracellular markers and enzymatic immunoassay, for secreted molecular markers (e.g. PEDF).

Thus, according to another aspect of the present invention there is provided a method of generating retinal epithelial cells comprising:
(a) culturing pluripotent stem cells in a medium comprising a differentiating agent so as to generate differentiating cells, wherein the medium is devoid of a member of the transforming growth factor β (TGF β) superfamily;
(b) culturing the differentiating cells in a medium comprising the member of the transforming growth factor β (TGF β) superfamily and the differentiating agent to generate cells which are further differentiated towards the RPE lineage;
(c) analyzing the secretion of Pigment epithelium-derived factor (PEDF) from the cells which are further differentiated towards the RPE lineage; and
(d) culturing the cells which are further differentiated towards the RPE lineage in a medium comprising a differentiating agent so as to generate RPE cells, wherein the medium is devoid of a member of the transforming growth factor β (TGF β) superfamily, wherein step (d) is effected when the amount of the PEDF is above a predetermined level.

Preferably, step (d) is effected when the level of PEDF is above 100 ng/ml/day, 200 ng/ml/day, 300 ng/ml/day, 400 ng/ml/day, or 500 ng/ml/day.

Another method for determining potency of the cells during or following the differentiation process is by analyzing barrier function and polarized PEDF and VEGF secretion, as illustrated in Example 4, herein below.

Once the cells are promoted into RPE cells, they may be selected and/or expanded.

According to a particular embodiment, the selection is based on a negative selection—i.e. removal of non-RPE cells. This may be done mechanically by removal of non-pigmented cells or removal of non-polygonal cells or by use of surface markers.

According to another embodiment, the selection is based on a positive selection i.e. selection based on morphology (e.g. pigmented cells and/or polygonal cells). This may be done by visual analysis or use of surface markers.

According to still another embodiment, the selection is based first on a negative selection and then on a positive selection.

Expansion of RPE cells may be effected on an extra cellular matrix, e.g. gelatin, collagen or poly-D-lysine and laminin. For expansion, the cells may be cultured in serum-free KOM, serum comprising medium (e.g. DMEM+20%) or Nuristem medium (06-5102-01-1A Biological Industries). Optionally, the cells may be exposed to nicotinamide during the expansion phase—at concentrations between 1-100 mM, 5-50 mM, 5-20 mM, e.g. 10 mM. Under these culture conditions, the pigmented cells reduce pigmentation and acquire a fibroid-like morphology. Following further prolonged culture and proliferation into high-density cultures, the cells re-acquire the characteristic polygonal shape morphology and preferably also pigmentation of RPE cells.

The RPE cells may be expanded in suspension or in a monolayer. The expansion of the RPE cells in monolayer cultures may be modified to large scale expansion in bioreactors by methods well known to those versed in the art.

The population of RPE cells generated according to the methods described herein may be characterized according to a number of different parameters.

Thus, for example, the RPE cells obtained are polygonal in shape and are pigmented.

According to one embodiment, at least 70%, 75%, 80%, 85% 90%, 95%, at least 96%, at least 97%, at least 98%, at least 99% or even 100% of the cells of the RPE cell populations obtained co-express both premelanosome protein (PMEL17) and cellular retinaldehyde binding protein (CRALBP).

Figure 27A:
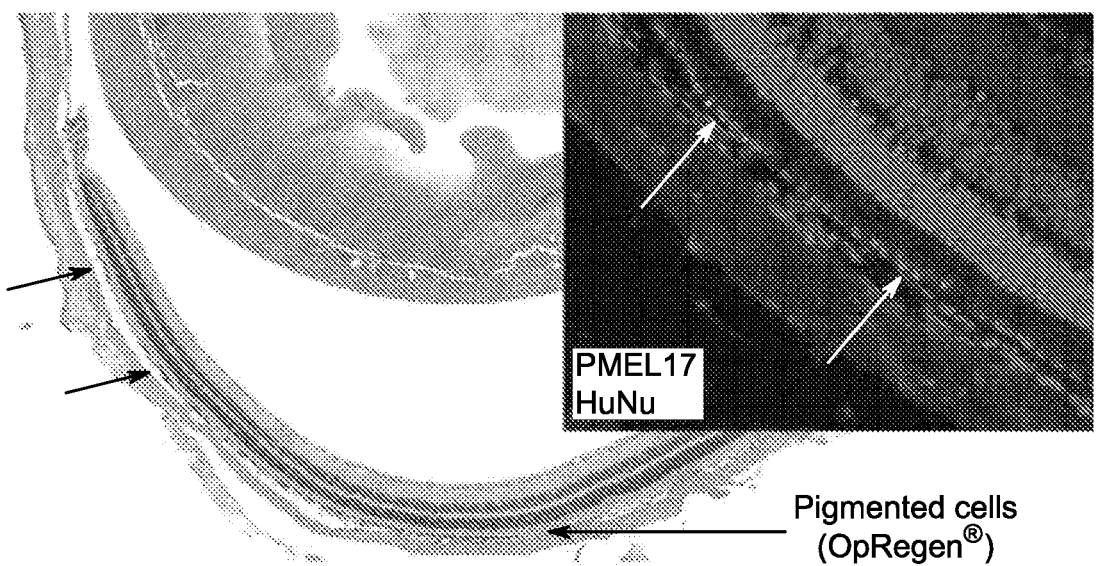
FIGS. 27A-C are photographs illustrating the biodistribution of the cells following subretinal injection into NOD-SCID.
Figure 27B:
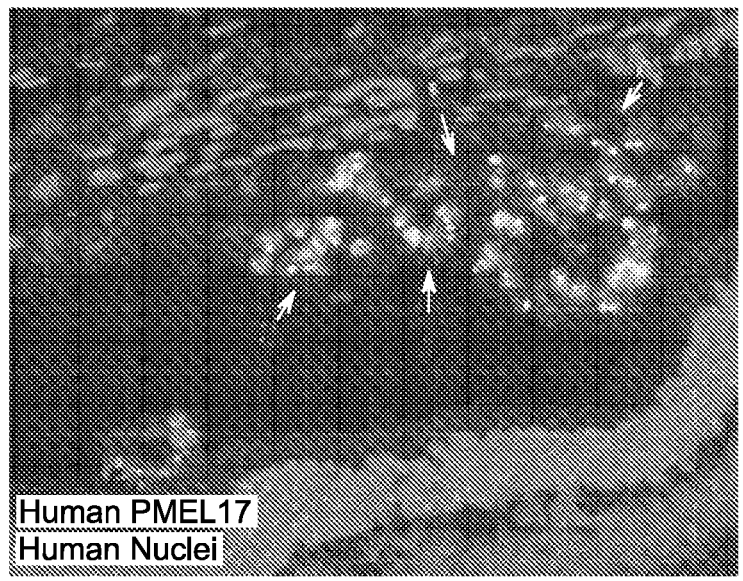
Figure 27C:
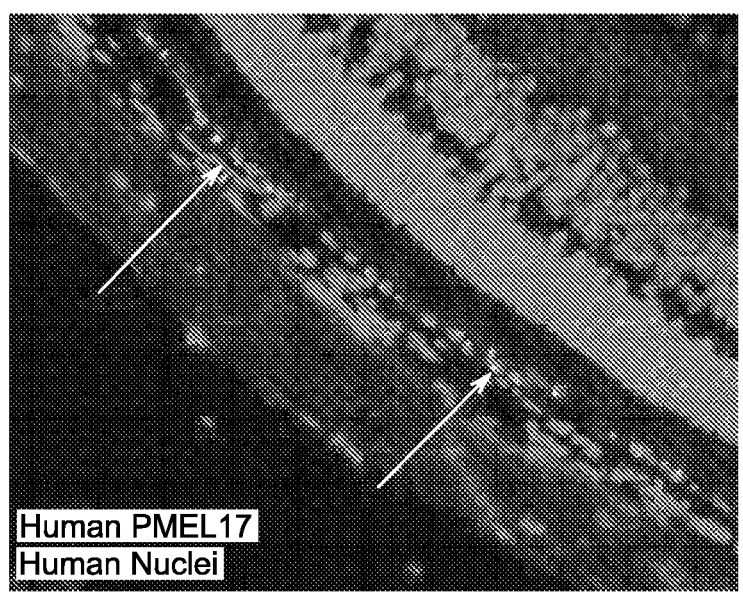

Following administration, the cells described herein are capable of forming a monolayer (as illustrated in FIG. 27C).

According to one embodiment, the trans-epithelial electrical resistance of the cells in a monolayer is greater than 100 ohms.

Preferably, the trans-epithelial electrical resistance of the cells is greater than 150, 200, 250, 300, 300, 400, 500, 600, 700, 800 or even greater than 900 ohms.

According to a particular embodiment, the TEER is between 100-1000 ohms, more preferably between 100-900 ohms for example between 200-900 ohms, 300-800 ohms, 300-700 ohms, 400-800 ohms or 400-700 ohms.

Devices for measuring trans-epithelial electrical resistance (TEER) are known in the art. An exemplary set-up for measuring TEER is illustrated in FIG. 28.

It will be appreciated that the cell populations disclosed herein are devoid of undifferentiated human embryonic stem cells. According to one embodiment, less than 1:250,000 cells are Oct4+TRA-1-60+ cells, as measured for example by FACS. The cells also do not express or downregulate expression of GDF3 or TDGF relative to hESCs as measured by PCR.

Another way of characterizing the cell populations disclosed herein is by marker expression. Thus, for example, at least 80%, 85%, or 90% of the cells express Bestrophin 1, as measured by immunostaining. According to one embodiment, between 90-95% of the cells express bestrophin.

According to another embodiment, at least 80%, 85%, 87%, 89% or 90% of the cells express Microphthalmia-associated transcription factor (MITF), as measured by immunostaining. For example, between 85-95% of the cells express MITF.

According to another embodiment, at least 50%, 55%, 60%, 70%, 75% 80% 85%, 87%, 89% or 90% of the cells express paired box gene 6 (PAX-6) as measured by FACS.

The cells described herein can also be characterized according to the quantity and/or type of factors that they secrete. Thus, according to one embodiment, the cells preferably secrete more than 500, 750, 1000, or even 2000 ng of Pigment epithelium-derived factor (PEDF) per ml per day, (e.g. following 14 days in culture) as measured by ELISA.

It will be appreciated that the RPE cells generated herein secrete PEDF and vascular endothelial growth factor (VEGF) in a polarized manner. According to particular embodiments, the ratio of apical secretion of PEDF:basal secretion of PEDF is greater than 1. According to particular embodiments, the ratio of apical secretion of PEDF:basal secretion of PEDF is greater than 2. According to particular embodiments, the ratio of apical secretion of PEDF:basal secretion of PEDF is greater than 3. In addition, the ratio of basal secretion of VEGF:apical secretion of VEGF is greater than 1. According to particular embodiments, the ratio of basal secretion of VEGF:apical secretion of VEGF is greater than 1.5, 2 or 2.5.

The cells of the present invention secrete additional factors including for example angiogenin, the immunomodulatory factors IL-6, sgp130, MIF, sTNF-R1, sTRAIL-R3, MCP-1 and Osteoprotegerin, the extracellular matrix regulators TIMP-1 and TIMP-2 and the protein Ax1.

According to another aspect, at least 80% of the cells of the cell population co-express premelanosome protein (PMEL17) and cellular retinaldehyde binding protein (CRALBP) and further a portion (at least 10%, 20%, 30%, 40%, 50%, 60%, 70%, 80%, 90%, 95%) of the cells secrete/shed each of angiogenin, tissue inhibitor of metalloproteinase 2 (TIMP2), soluble glycoprotein 130 (sgp130) and soluble form of the ubiquitous membrane receptor 1 for tumor necrosis factor-α (sTNF-R1).

It will be appreciated that in some cases all the cells that co-express premelanosome protein (PMEL17) and cellular retinaldehyde binding protein (CRALBP) also secrete/shed angiogenin, tissue inhibitor of metalloproteinase 2 (TIMP 2), soluble glycoprotein 130 (sgp130) and soluble form of the ubiquitous membrane receptor 1 for tumor necrosis factor-α (sTNF-R1).

In other cases the majority (more than 50%, 60%, 70%, 80, 90% of the cells that co-express premelanosome protein (PMEL17) and cellular retinaldehyde binding protein (CRALBP) also secrete/shed angiogenin, tissue inhibitor of metalloproteinase 2 (TIMP2), soluble glycoprotein 130 (sgp130) and soluble form of the ubiquitous membrane receptor 1 for tumor necrosis factor-α (sTNF-R1).

The RPE cells generated herein preferably secrete angiogenin, TIMP2, sgp130 and sTNF-R1 in a polarized manner.

According to particular embodiments, the ratio of apical secretion of sgp130:basal secretion of sgp130 is greater than 1. According to particular embodiments, the ratio of apical secretion of sgp130:basal secretion of sgp130 is greater than 2. According to particular embodiments, the ratio of apical secretion of sgp130:basal secretion of sgp130 is greater than 3.

Furthermore, the ratio of apical sTNF-R1:basal sTNF-R1 is greater than 1. According to particular embodiments, the ratio of apical sTNF-R1:basal sTNF-R1 is greater than 2. According to particular embodiments, the ratio of apical sTNF-R1:basal sTNF-R1 is greater than 3.

In addition, the ratio of basal secretion of angiogenin:apical secretion of angiogenin is greater than 1. According to particular embodiments, the ratio of basal secretion of angiogenin:apical secretion of angiogenin is greater than 1.5, 2, 2.5 or 3.

Furthermore, the ratio of apical secretion of TIMP2:basal secretion of TIMP2 is greater than 1. According to particular embodiments, the ratio of apical secretion of TIMP2:basal secretion of TIMP2 is greater than 2. According to particular embodiments, the ratio of apical secretion of TIMP2:basal secretion of TIMP2 is greater than 3.

The stability of the cells is another characterizing feature. Thus, for example the amount of PEDF secretion remains stable in the cells following their incubation at 2-8° C. for 6 hours, 8 hours, 10 hours, 12 hours or even 24 hours. Further, the polarized secretion of PEDF and VEGF remains stable following incubation of the cells at 2-8° C. for 6 hours, 8 hours, 10 hours, 12 hours or even 24 hours. Further, the TEER of the cells remains stable in the cells following their incubation at 2-8° C. for 6 hours, 8 hours, 10 hours, 12 hours or even 24 hours.

In another embodiment, the cells are characterized by their therapeutic effect. Thus, for example the present inventors have shown that the cell populations are capable of rescuing visual acuity in the RCS rat following subretinal administration. In addition, the cell populations are capable of rescuing photoreceptors (e.g. cone photoreceptors) for up to 180 days (in some embodiments at least 180 days) post-subretinal administration in the RCS rat.

It would be well appreciated by those versed in the art that the derivation of RPE cells is of great benefit. They may be used as an in vitro model for the development of new drugs to promote RPE cell survival, regeneration and function. RPE cells may serve for high throughput screening for compounds that have a toxic or regenerative effect on RPE cells. They may be used to uncover mechanisms, new genes, soluble or membrane-bound factors that are important for the development, differentiation, maintenance, survival and function of photoreceptor cells.

The RPE cells may also serve as an unlimited source of RPE cells for transplantation, replenishment and support of malfunctioning or degenerated RPE cells in retinal degenerations. Furthermore, genetically modified RPE cells may serve as a vector to carry and express genes in the eye and retina after transplantation.

The RPE cells produced by the method of the present disclosure may be used for large scale and/or long term cultivation of such cells. To this end, the method of the invention is to be performed in bioreactors and or cell culture systems suitable for large scale production of cells, and in which undifferentiated hSCs are to be cultivated in accordance with the invention. General requirements for cultivation of cells in bioreactors and or cell culture systems are well known to those versed in the art.

Harvesting of the cells may be performed by various methods known in the art. Non-limiting examples include mechanical dissection and dissociation with papain or trypsin (e.g. TrypLE select). Other methods known in the art are also applicable.

The RPE cells generated as described herein may be transplanted to various target sites within a subject's eye. In accordance with one embodiment, the transplantation of the RPE cells is to the subretinal space of the eye, which is the normal anatomical location of the RPE (between the photoreceptor outer segments and the choroid). In addition, dependent upon migratory ability and/or positive paracrine effects of the cells, transplantation into additional ocular compartments can be considered including the inner or outer retina, the retinal periphery and within the choroids.

Retinal diseases which may be treated using the RPE cells described herein include, but are not limited to retinitis pigmentosa, retinoschisis, lattice degeneration, Best disease, and age related macular degeneration (AMD).

Further, transplantation may be performed by various techniques known in the art. Methods for performing RPE transplants are described in, for example, U.S. Pat. Nos. 5,962,027, 6,045,791, and 5,941,250 and in Eye Graefes Arch Clin Exp Opthalmol March 1997; 235(3):149-58; Biochem Biophys Res Commun Feb. 24, 2000; 268(3): 842-6; Opthalmic Surg February 1991; 22(2): 102-8. Methods for performing corneal transplants are described in, for example, U.S. Pat. No. 5,755,785, and in Eye 1995; 9 (Pt 6 Su):6-12; Curr Opin Opthalmol August 1992; 3 (4): 473-81; Ophthalmic Surg Lasers April 1998; 29 (4): 305-8; Ophthalmology April 2000; 107 (4): 719-24; and Jpn J Ophthalmol November-December 1999; 43(6): 502-8. If mainly paracrine effects are to be utilized, cells may also be delivered and maintained in the eye encapsulated within a semi-permeable container, which will also decrease exposure of the cells to the host immune system (Neurotech USA CNTF delivery system; PNAS Mar. 7, 2006 vol. 103(10) 3896-3901).

In accordance with one embodiment, transplantation is performed via pars plana vitrectomy surgery followed by delivery of the cells through a small retinal opening into the sub-retinal space or by direct injection. Alternatively, cells may be delivered into the subretinal space via a trans-scleral, trans-choroidal approach. In addition, direct trans-scleral injection into the vitreal space or delivery to the anterior retinal periphery in proximity to the ciliary body can be performed.

The RPE cells may be transplanted in various forms. For example, the RPE cells may be introduced into the target site in the form of cell suspension, or adhered onto a matrix, extracellular matrix or substrate such as a biodegradable polymer or a combination. The RPE cells may also be transplanted together (co-transplantation) with other retinal cells, such as with photoreceptors.

Thus, the invention also pertains to pharmaceutical compositions of RPE cells described herein. The composition is preferably such suitable for transplantation into the eye. Thus, for example, the RPE cells may be formulated in an intraocular irrigating solution such as BSS Plus™.

It is expected that during the life of a patent maturing from this application many relevant technologies will be developed for the generation of RPE cells, and the term RPE cells is intended to include all such new technologies a priori.

As used herein the term "about" refers to ±10%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

As used herein, the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Maryland (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Culture of Animal Cells—A Manual of Basic Technique" by Freshney, Wiley-Liss, N. Y. (1994), Third Edition; "Current Protocols in Immunology" Volumes I-III Coligan J. E., ed. (1994); Stites et al. (eds), "Basic and Clinical Immunology" (8th Edition), Appleton & Lange, Norwalk, CT (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, CA (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

Example 1

Qualification of the CRALBP/PMEL17 Double Staining FACS Method

The aim of this study was to qualify the CRALBP/PMEL17 double staining FACS method by demonstrating the method's accuracy and precision in a minimum of 6 independent spiking assays over at least 3 testing days. The assay qualification was performed using OpRegen® hath 5C as the positive control cells and HAD-C102-hESCs, as the negative control cells. A calibration curve of known quantities of RPE (OpRegen® 5C) spiked into hESCs was used for testing the accuracy and precision at different spiking points. The expected accuracy and precision were up to 25% at all points.

Staining Protocol: Negative Control hESC cells taken from a cryopreserved hESC bank (HAD-C102 p48 4.5.2014) were thawed in Nutristem (containing HSA) according to sponsor protocols. Positive Control RPE cell stock: OpRegen® batch 5C cells (reference line) were thawed into in 20% HS-DMEM according to sponsor protocols. Thawed OpRegen® 5C and HAD-C102 hESC were spun down, re-suspended in 1 ml PBS (−), filtered through a 35 µM cell strainer and counted with Trypan Blue. The cell concentration was adjusted to $0.73 \times 10^6$-$10^6$ cells/ml in PBS (−). 1 µl/ml FVS450 was added to each cell suspension followed by vortexing and incubation for 6 minutes at 37° C. FVS450 was washed with 0.1% BSA, and re-suspended in 0.1% BSA-Fe-block (5 min at RT) to block all Fc-epitopes on the cells. Cells were then washed with PBS (−) and fixed in 80% Methanol (5 min at 4° C.). Fixed cells were washed once with PBS (−), once with 0.1% PBS-T, and permeabilized with 0.1% PBS-T (20 minutes at RT). Permeabilization solution was replaced with 10% Normal goat serum (NGS) Blocking Solution (200,000 cells/50 µl) for at least 30 minutes (max one hour) at RT. During incubation time quality sample tubes (QSs) were prepared and at the end of blocking, cells were divided and immunostained. Cells were incubated with primary antibodies for 30 minutes followed by 3 washes with 0.1% PBS-T and 30 min incubation with secondary antibodies and 3 washes with 0.1% PBS-T.

Negative and positive control cells were stained with the viability stain FVS450, fixed, blocked and permeabilized. A calibration curve of known quantities of positive control RPE (OpRegen® 5C) cells in negative control hESCs, at 4 concentrations (25%, 50%, 75%, and 95% RPE in hESC), was then generated based on the Trypan Blue viability cell count of each population. Negative and positive control cells and the mixed populations were immunostained with primary monoclonal antibodies specific to the RPE markers CRALBP and PMEL17, followed by staining with matched secondary antibodies (anti-mouse-FITC and anti-rabbit-Alexa Fluor 647, respectively). Stained cells were FACS analyzed to measure the percent viable single cell gated CRALBP+PMEL17+ cells.

Results

Accuracy: Accuracy of the assay was determined from test results of 4 levels of spiked RPEs (25%, 50%, 75% and 95%). The accuracy of the RPE stock (OpRegen® 5C) was determined with respect to it being potentially 100% RPE cells. Each level values were analyzed by six independent runs/determinations.

The 50% concentration level was considered to be the lower limit of quantitation with an expected accuracy of up to 25% (50% level ranged from −8.41 to 20.14; 75% and 99.5% levels ranged from −5.32 to 6.88).

These results meet the expected outcomes for relative bias of up to 25%, and indicate that the assay is accurate for determination of CRALBP+PMEL17+ double positive cells in concentrations ranging from 50-99.5%. Since OpRegen® 5C yields 99.5% CRALBP+PMEL17+× double positive RPE cells, a relative bias of less than 25% for a result >99.5% cannot be assured.

TABLE 1

| Run | Assigned Concentration (%) | Measured Concentration (%) | Relative Bias (%) |
|---|---|---|---|
| 1 | 25 | 20.88 | −16.48 |
| 2 |  | 31.61 | 26.44 |
| 3 |  | 32.20 | 28.80 |
| 4 |  | 32.01 | 28.04 |
| 5 |  | 25.71 | 2.84 |
| 6 |  | 26.87 | 7.48 |
| 1 | 50% | 45.93 | −8.14 |
| 2 |  | 60.08 | 20.16 |
| 3 |  | 56.87 | 13.74 |
| 4 |  | 58.51 | 17.02 |
| 5 |  | 50.56 | 1.12 |
| 6 |  | 49.52 | −0.96 |

TABLE 1-continued

| Run | Assigned Concentration (%) | Measured Concentration (%) | Relative Bias (%) |
|---|---|---|---|
| 1 | 75% | 71.01 | −5.32 |
| 2 | | 79.64 | 6.19 |
| 3 | | 78.41 | 4.55 |
| 4 | | 80.16 | 6.88 |
| 5 | | 73.85 | −1.53 |
| 6 | | 72.94 | −2.75 |
| 1 | 95% | 93.94 | −1.12 |
| 2 | | 96.14 | 1.20 |
| 3 | | 95.11 | 0.12 |
| 4 | | 95.59 | 1.01 |
| 5 | | 93.81 | −1.25 |
| 6 | | 93.70 | −1.37 |
| 1 | 100% | 98.79 | −1.21 |
| 2 | | 99.69 | −0.31 |
| 3 | | 99.62 | −0.38 |
| 4 | | 99.59 | −0.41 |
| 5 | | 99.60 | −0.40 |
| 6 | | 99.48 | −0.52 |

Intermediate Precision: The intermediate precision of the assay was determined from results of 6 assays carried out by one operator. In each assay the percent single viable RPEs was determined and from that the % CY was calculated. Table 2 summarizes the test results. As shown, % CY for all concentration levels was below 20% and can be measured with adequate precision. % CY for the concentration levels 25%, 50%, 75%, 95% and 100% RPEs, were 16.14%, 10.61%, 5.10%, 1.17%, and 0.34%, respectively. These results meet the expected values for precision. The measured percent RPEs is within 20% of the expected value at all concentrations. These results indicate that the assay is precise for determination of RPEs in concentrations ranging from 25-99.5%.

TABLE 2

| Assigned Concentration (%) | Run | Measured Concentration (% RPE) |
|---|---|---|
| 25 | 1 | 20.88 |
| | 2 | 31.61 |
| | 3 | 32.20 |
| | 4 | 32.01 |
| | 5 | 25.71 |
| | 6 | 26.87 |
| | Mean % RPE | 28.21 |
| | SD | 4.55 |
| | % CV | 16.14 |
| 50 | 1 | 45.93 |
| | 2 | 60.08 |
| | 3 | 56.87 |
| | 4 | 58.51 |
| | 5 | 50.56 |
| | 6 | 49.52 |
| | Mean % RPE | 53.58 |
| | SD | 5.68 |
| | % CV | 10.61 |
| 75 | 1 | 71.01 |
| | 2 | 79.64 |
| | 3 | 78.41 |
| | 4 | 80.16 |
| | 5 | 73.85 |
| | 6 | 72.94 |
| | Mean % RPE | 76.00 |
| | SD | 3.88 |
| | % CV | 5.10 |
| 95 | 1 | 93.94 |
| | 2 | 96.14 |
| | 3 | 95.11 |
| | 4 | 95.96 |
| | 5 | 93.81 |
| | 6 | 93.70 |
| | Mean % RPE | 94.78 |
| | SD | 1.11 |
| | % CV | 1.17 |
| 100 | 1 | 98.79 |
| | 2 | 99.69 |
| | 3 | 99.62 |
| | 4 | 99.59 |
| | 5 | 99.60 |
| | 6 | 99.48 |
| | Mean % RPE | 99.46 |
| | SD | 0.34 |
| | % CV | 0.34 |

Repeatability: Sample repeatability was tested in 3 runs (#2, #3 and #4) in which duplicate OpRegen® SC samples were stained and acquired side by side. The results confirmed that sample identity obtained within an experiment is repeatable and consistent across samples.

Linearity/range: As shown in FIG. 1, linearity was measured using data that were found to be both accurate and precise. The coefficient of regression between the target (spiked) and measured results across the tested assay range (50%-100%) was found to be 0.99. Thus, the range of the method which demonstrates acceptable accuracy and precision and linearity is the range between 50% and 99.5% RPE cells, which covers the expected range of tested samples.

Positive control cells: The provisional level of CRALBP/PMEL17 double positive cells was set at equal to or greater than 95%.

Negative control cells: The provisional level of CRALBP/PMEL17 double positive cells for hESCs was set at equal to or less than 2%.

Stability: The results show that stained samples are stable at 4° C. also after one and 4 days and accuracy is kept within expected acceptance criteria, therefore the data acquisition can be performed within 96 hours of sample preparation.

Conclusion

The results presented herein indicate that the disclosed method is qualified and suitable for its intended use of in vitro determination of RPE purity in OpRegen® final product and at different stages along the production process of OpRegen®, with Accuracy of Relative Bias of <25% and precision of % CV<20% in the range of 50%-99.5% RPE cells.

Example 2

Assessing the Level of OpRegen® Purity

A FACS based method for assessing the level of human retinal pigment epithelial cells (RPE) purity as well as non-RPE cellular impurities in RPE cells was developed. Cellular retinaldehyde-binding protein (CRALBP), one of the visual cycle components, was bioinformatically identified as a unique marker for mature RPE cells. Preliminary studies using CRALBP specific monoclonal antibody have shown purity of above 98% in RPE cells generated according to methods described herein. These results were further supported by immunostaining for PMEL17, a melanosome marker found in RPE. In addition, different from some RPE specific markers, CRALBP is not expressed in melanocytes, a possible neural crest cellular contamination.

Test Sample and Controls: Human primary melanocytes (ATCC, PCS-200-013) were used as negative control cells for CRALBP and as positive control cells for PMEL17, type I transmembrane glycoprotein enriched in melanosomes (melanin granules). HADC102-hESCs at P29 (OpRegen® parental line), were used as negative control cells for both CRALBP and PMEL17. Clinical grade OpRegen® cells (batch 2A), and research grade OpRegen® (produced in GMP like Mock production; Mock IV D16) were used as the tested samples. The cells were generated as described in Example 3.

Immunostaining and FACS analysis: cells were thawed and stained using the Fixable Viability Stain (FVS450) (BD 562247), fixed with 80% Methanol, immunostained with the primary mouse anti CRALBP (Clone B2, Abcam ab15051), or its isotype control for mouse IgG2a (Abcam ab170191) and rabbit anti human PMEL17 (Clone EPR4864, Abeam ab137062) followed by secondary antibodies goat anti mouse (Dako F0479) and goat anti rabbit (Jackson 111-606-144), respectively.

Acquisition of FACS data was performed using a validated Navios flow cytometer (Beckman Coulter) and analysis was performed using FlowJo 7.6.

Results

Initial FACS data using anti CRALBP monoclonal antibody and showed that the purity level of OpRegen® is above 98%. Melanocytes which are a possible neural crest cellular contaminant were found negative for the unique RPE specific marker CRALBP (1.7%). The parental line HADC102-hESCs were negative to CRALBP (0.2%), as expected.

Figure 10:
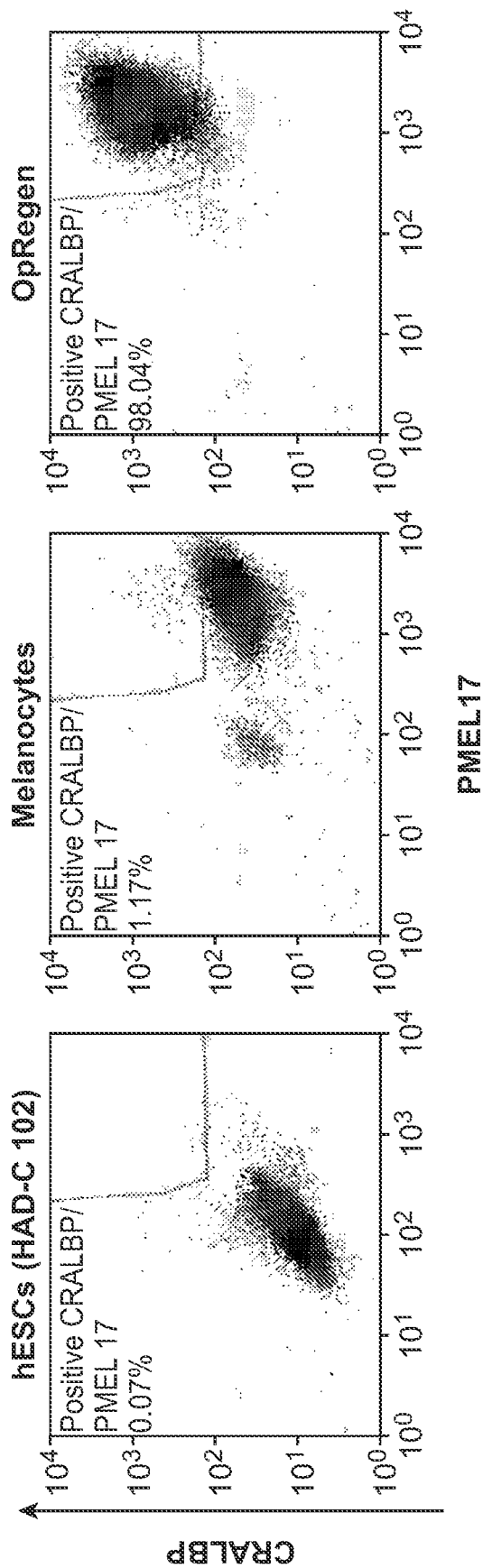
FIG. 10: Co-immunostaining with PMEL17 differentiate RPE cells (CRALBP+PMEL17+) from non RPE pigmented cells (PMEL17+CRALBP−; such as melanocytes).

The purity level of OpRegen® stayed above 98% following double staining with CRALBP and PMEL17 (FIG. 10). Melanocytes stained positive for PMEL17, as expected, but were negative for the double marked population (~1%). HADC102-hESCs were negative stained for CRALBP and PMEL17 (0.07%).

Example 3

Description of Manufacturing Process and Process Controls

OpRegen® is manufactured from the xeno-free GMP grade HAD-C102 hESC line grown on irradiated xeno-free GMP-grade human umbilical cord fibroblast feeders. Clinical-grade human fibroblast feeder cell line (CRD008; MCB) and working cell banks (WCBs) were produced under Good Manufacturing Practice (GMP) and xeno-free conditions, appropriately tested, characterized and banked. These were then used in the derivation of clinical-grade hESC line HAD-C102 from surplus human blastocysts under GMP and xeno-free conditions.

At the initial phase of production hESCs are expanded on irradiated feeders as colonies. They are then transferred to suspension culture to initiate differentiation in a directed manner. Spheroid bodies (SBs) are formed and then plated as an adherent culture under continued directed differentiation conditions towards a neural fate and subsequently towards RPE cells. At the end of the differentiation phase non-pigmented areas are physically excised and pigmented cells are enzymatically collected, seeded and expanded. Purified hESC-derived RPE cells (DS) are harvested at passage 2 and immediately processed to the DP. Duration of the manufacturing process depends on the hESCs growth rate (~2 months from thawing) and in total usually spans over 4-5 months.

Each step of the manufacturing process, including the in-process quality control (QC) tests is briefly described below.

Steps 1-3: Generation of human cord fibroblast feeder Working Cell Bank (WCB). A vial of human cord feeder Master Cell Bank (MCB) (CRD008-MCB) at passage 3-4 was thawed, expanded in Dulbecco's Modified Eagle's Medium (DMEM, SH30081.01, Hyclone) supplemented with 20% human serum (14-498E, Lonza), irradiated (Gamma cell, 220 Exel, MDS Nordion 3,500 rads) and cryopreserved at passages 7-8 to generate the working cell banks (WCBs). Prior to cryopreservation, samples from the feeder cell cultures were tested for sterility, *mycoplasma* and Limulus Amebocyte Lysate (LAL), morphology, karyotype, cell number, and viability. In addition, post thawing, their identity to the MCB, their inability to proliferate and their ability to support un-differentiated HAD-C102-hESC growth were confirmed. If the WCB passed all QC testing, the bank was released for expansion of hESCs.

Production Steps 1-3 are depicted in FIG. 12.

Figure 2:
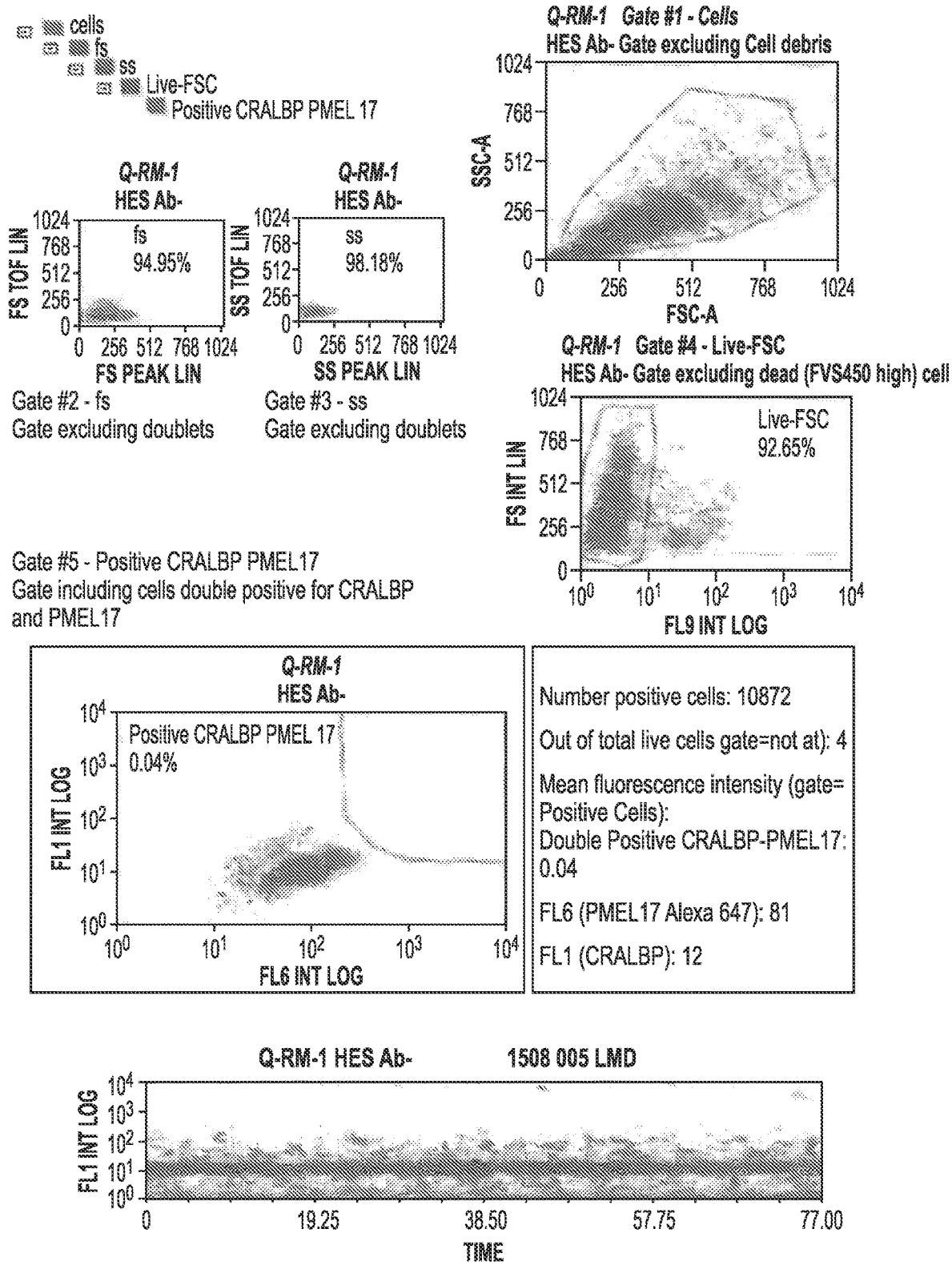
FIG. 2 is FACS analysis of negative control hESC cells stained with anti CRALBP and anti PMEL17.
Figure 3:
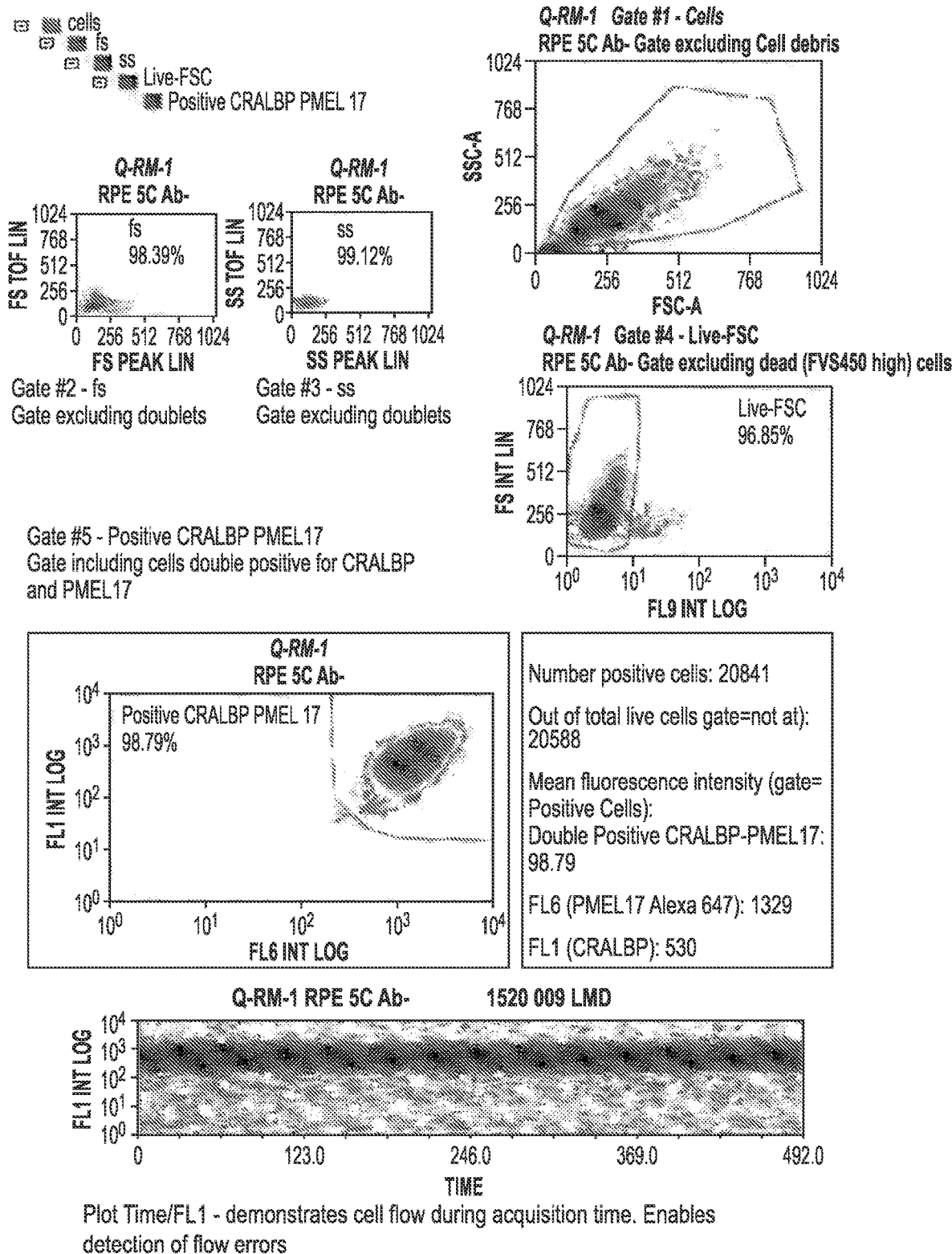
FIG. 3 is FACS analysis of positive control of the reference RPE line OpRegen® 5C cells stained with anti CRALBP and anti PMEL17.
Figure 4:
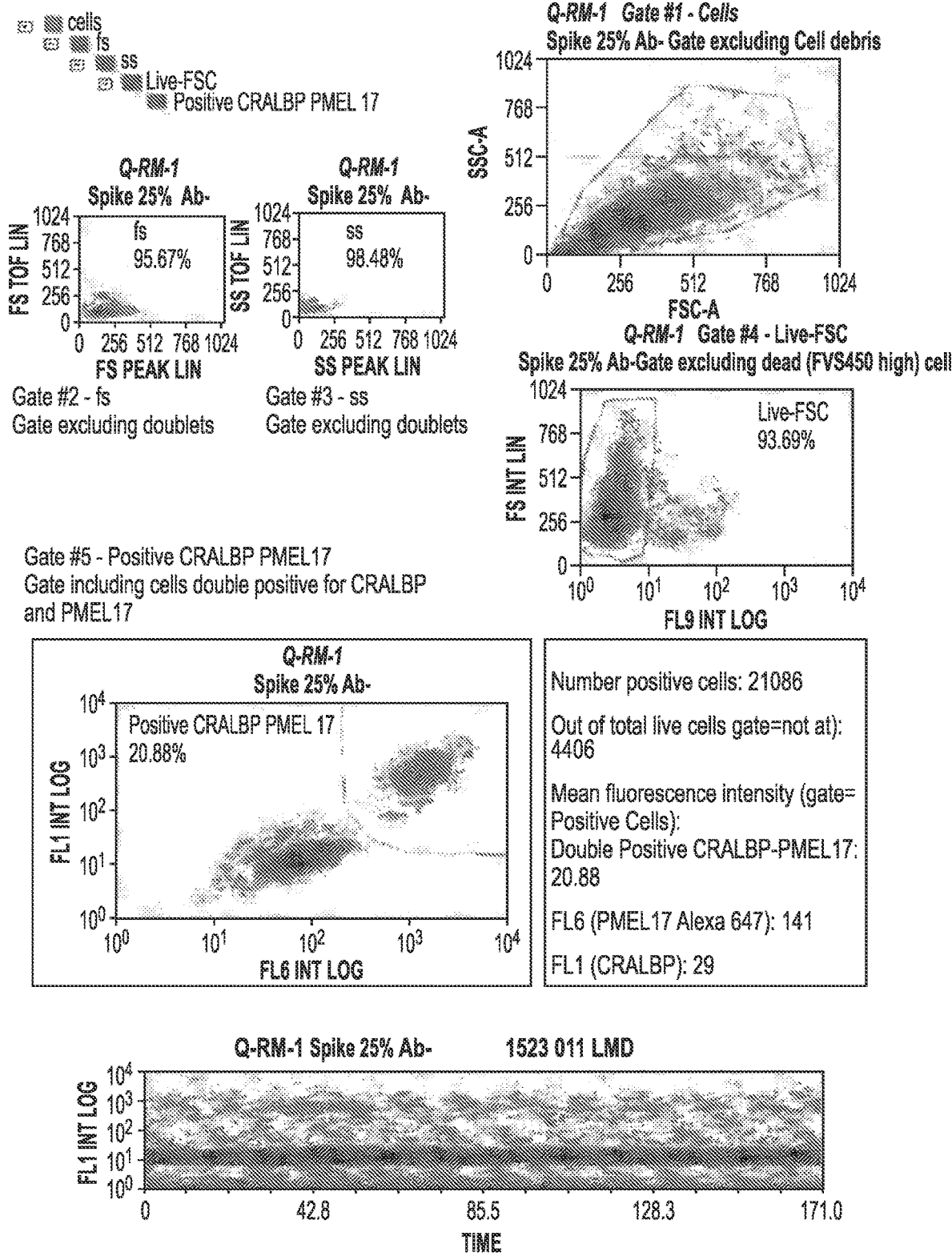
FIG. 4 is FACS analysis of 25% Spiked OpRegen® 5C in hESCs stained with anti CRALBP and anti PMEL17.
Figure 5:
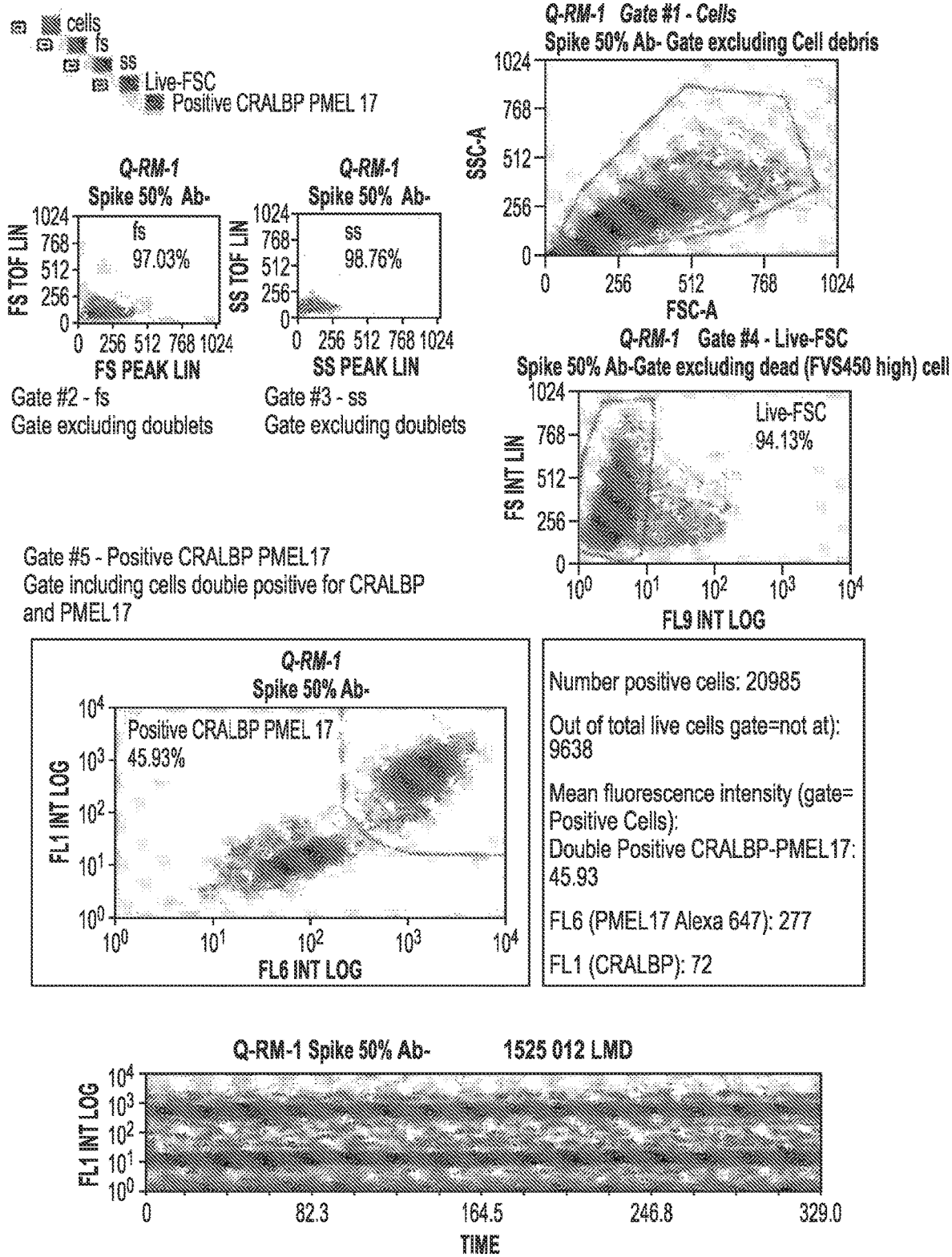
FIG. 5 is FACS analysis of 50% Spiked OpRegen® 5C in hESCs stained with anti CRALBP and anti PMEL17.
Figure 6:
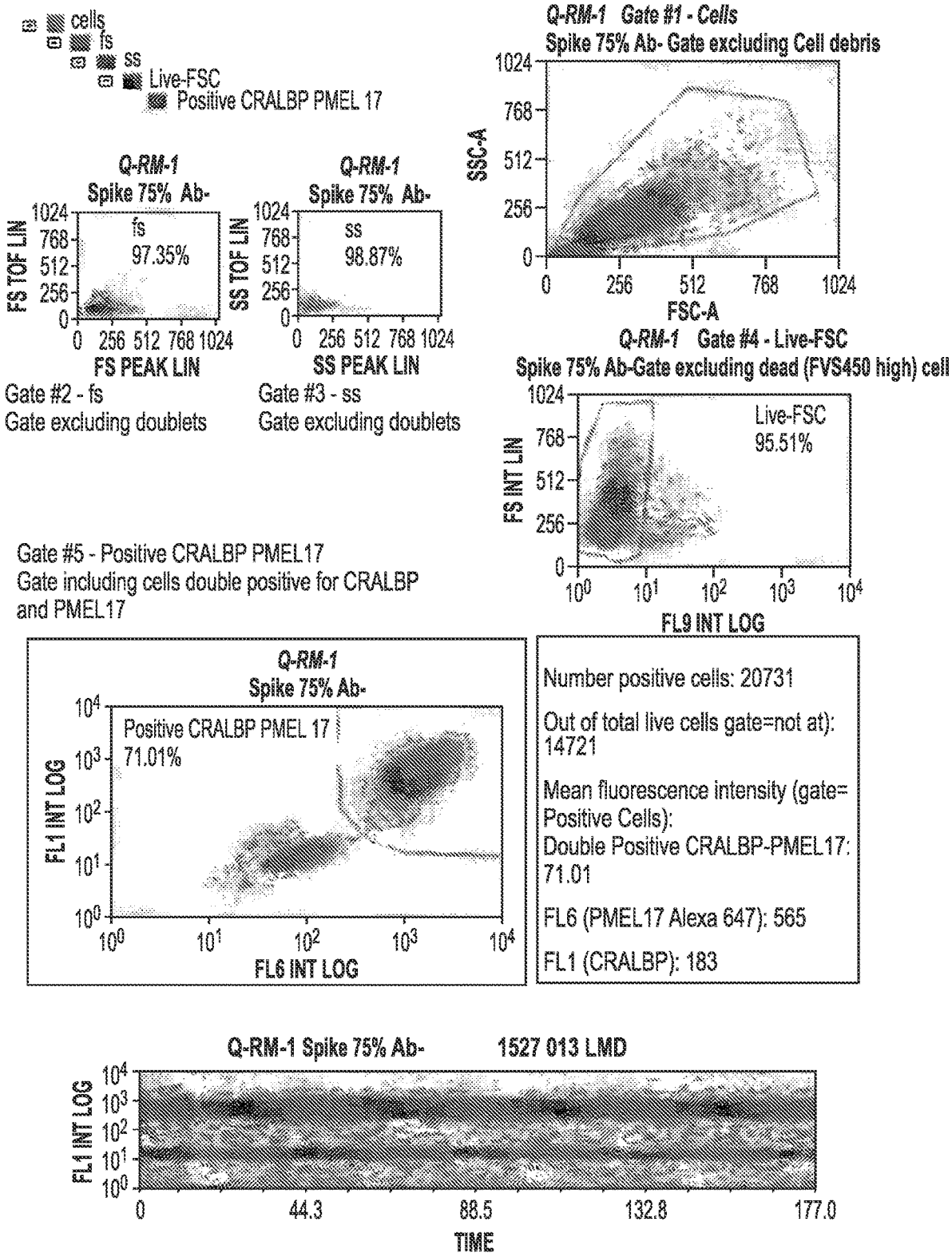
FIG. 6 is FACS analysis of 75% Spiked OpRegen® 5C in hESCs stained with anti CRALBP and anti PMEL17.
Figure 7:
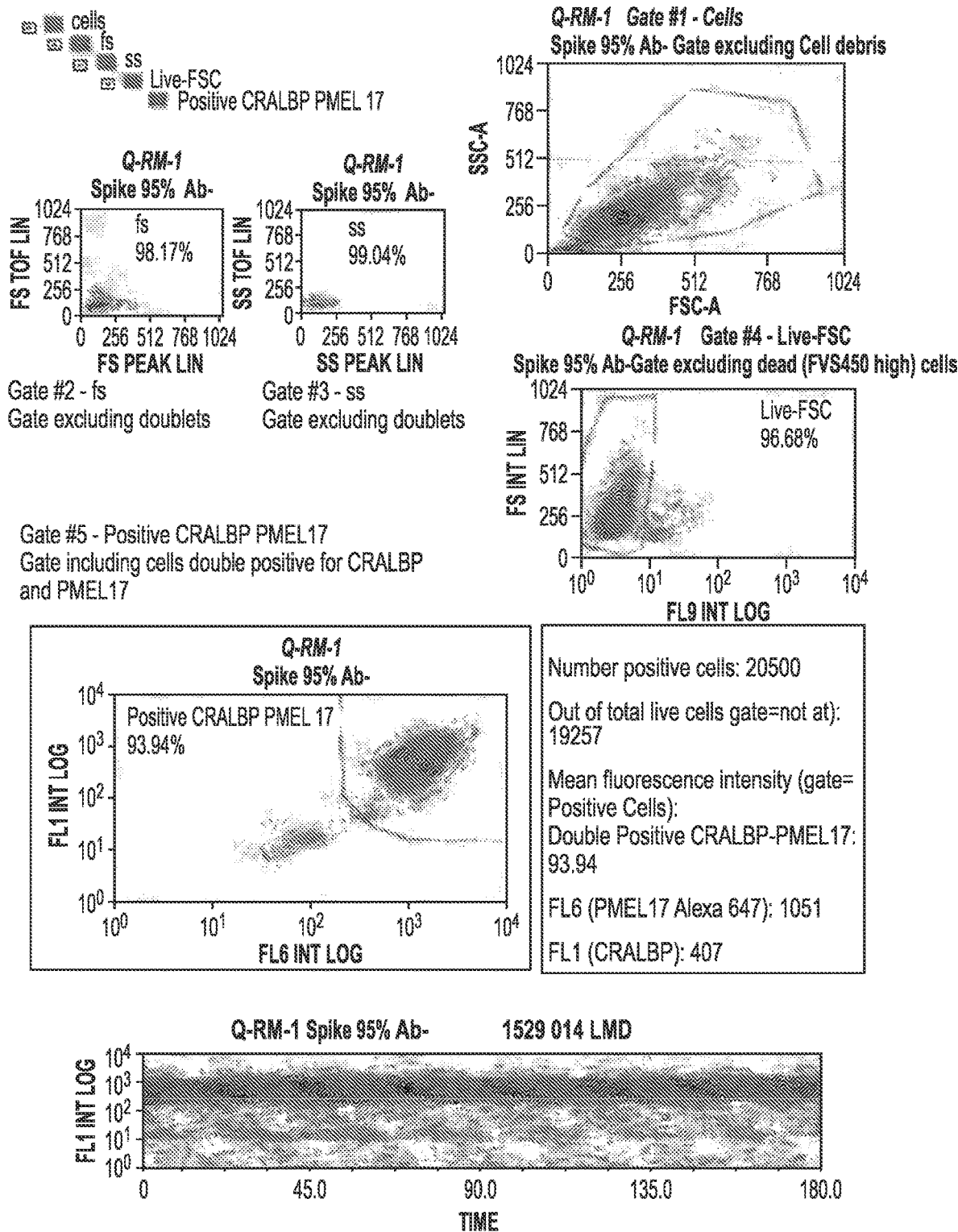
FIG. 7 is FACS analysis of 95% Spiked OpRegen® 5C in hESCs stained with anti CRALBP and anti PMEL17.
Figure 8:
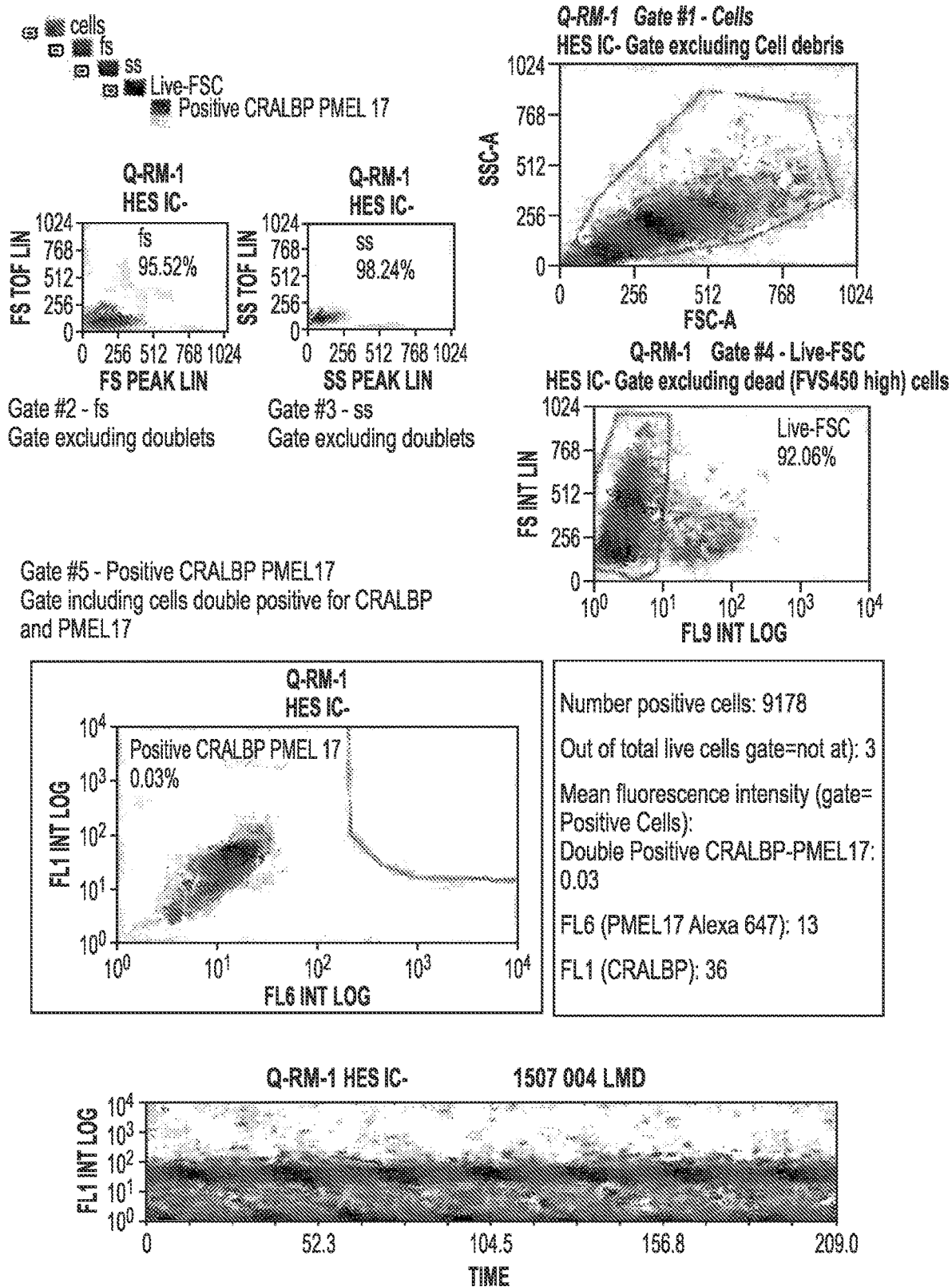
FIG. 8 is FACS analysis of hESCs stained with Isotype Controls.
Figure 9:
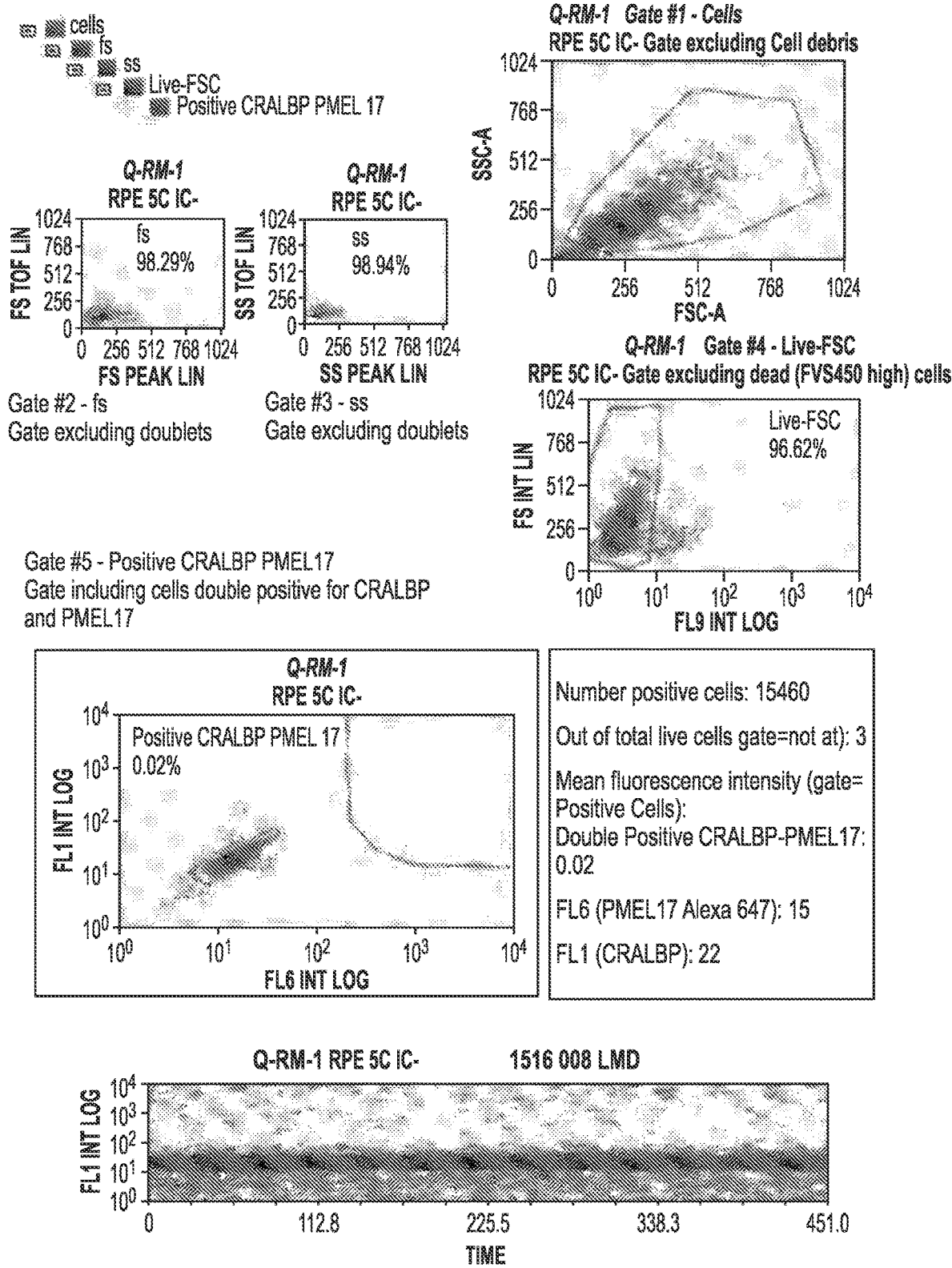
FIG. 9 is FACS analysis of OpRegen® 5C cells stained with the Isotype Controls.
Figure 13:
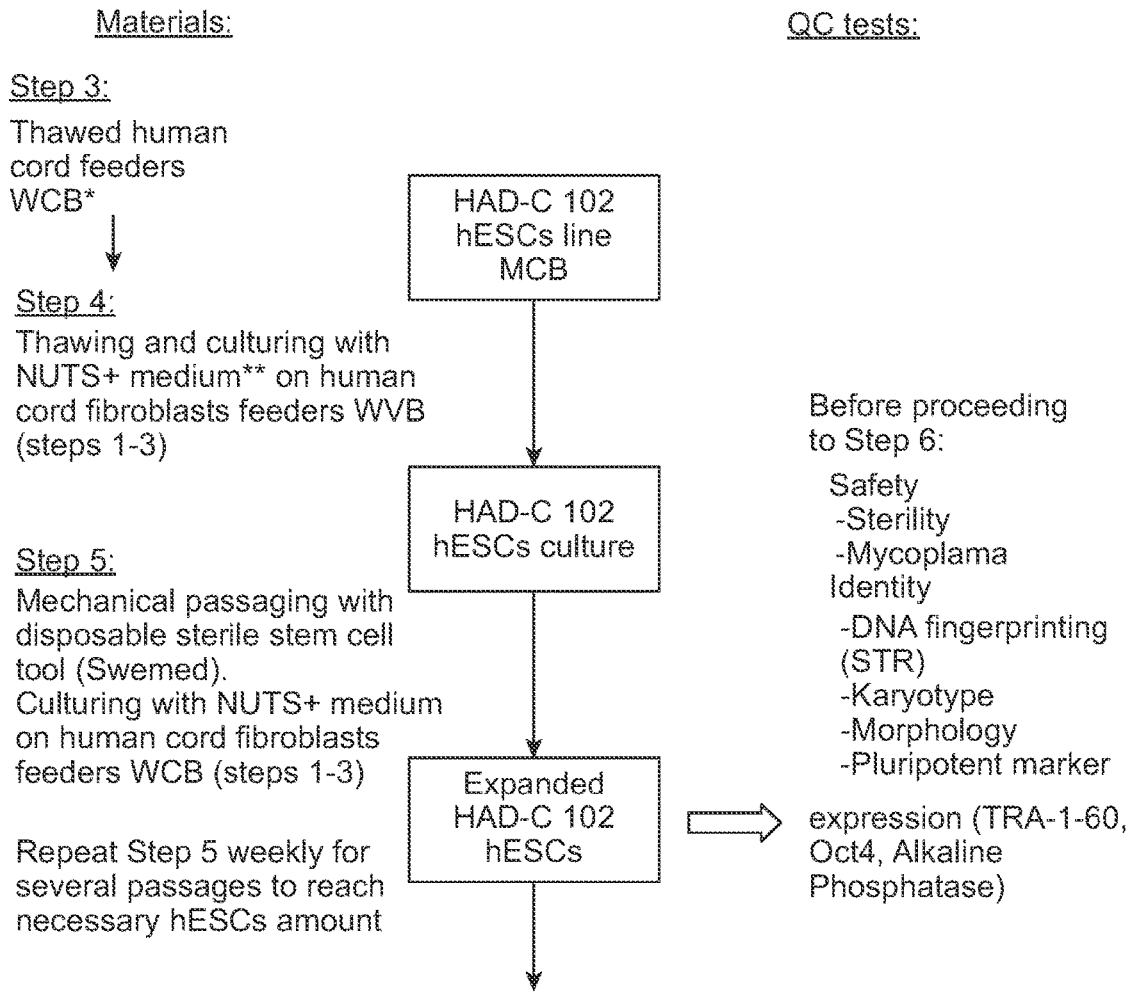
FIG. 13: Manufacturing Process, Steps 4-5: Expansion of hESCs.

Steps 4-5: Expansion of hEGSs. A single vial of the human cord fibroblast WCB (either CRD008-WCB8 or CRD008-WCB9) was thawed and plated in center well plates covered with recombinant human gelatin (RhG100-001, Fibrogen) at a concentration of 70,000-100,000 cells/ml/plate in DMEM (SH30081.01, Hyclone) supplemented with 20% human serum (14-498E, Lonza). The cells were incubated over night at 37° C. 5% $CO_2$ to allow the fibroblasts to attach. 1-4 days later, a sample from HAD-C102-hESC MCB was thawed and plated for 6-7 days at 37° C. 5% $CO_2$ on top of the feeder cells in Nutristem "Plus" Medium (which is GMP-grade and xeno-free) that contains the growth factors bFGF and TGF-β (05-102-1A, Biological Industries, Israel). On day 6-7 hESC culture was mechanically disrupted (using a sterile tip or a disposable sterile stem cell tool; 14602 Swemed) and passaged into additional freshly prepared plates containing feeder cells at a concentration of 70,000-100,000 cells/plate. This was repeated weekly for several passages to reach the necessary amount of hESC to initiate differentiation (FIG. 13, Steps 4-5). Prior to their use, expanded HAD-C102-hESCs were tested for sterility, *mycoplasma*, LAL, karyotype, and identity to the MCB. In addition, their pluripotent morphological appearance as well as unified expression of pluripotency markers (TRA-1-60, Oct4, and alkaline phosphatase) were confirmed (FIG. 2, Step 5). Production Steps 4-5 are depicted in FIG. 13.

Figure 14:
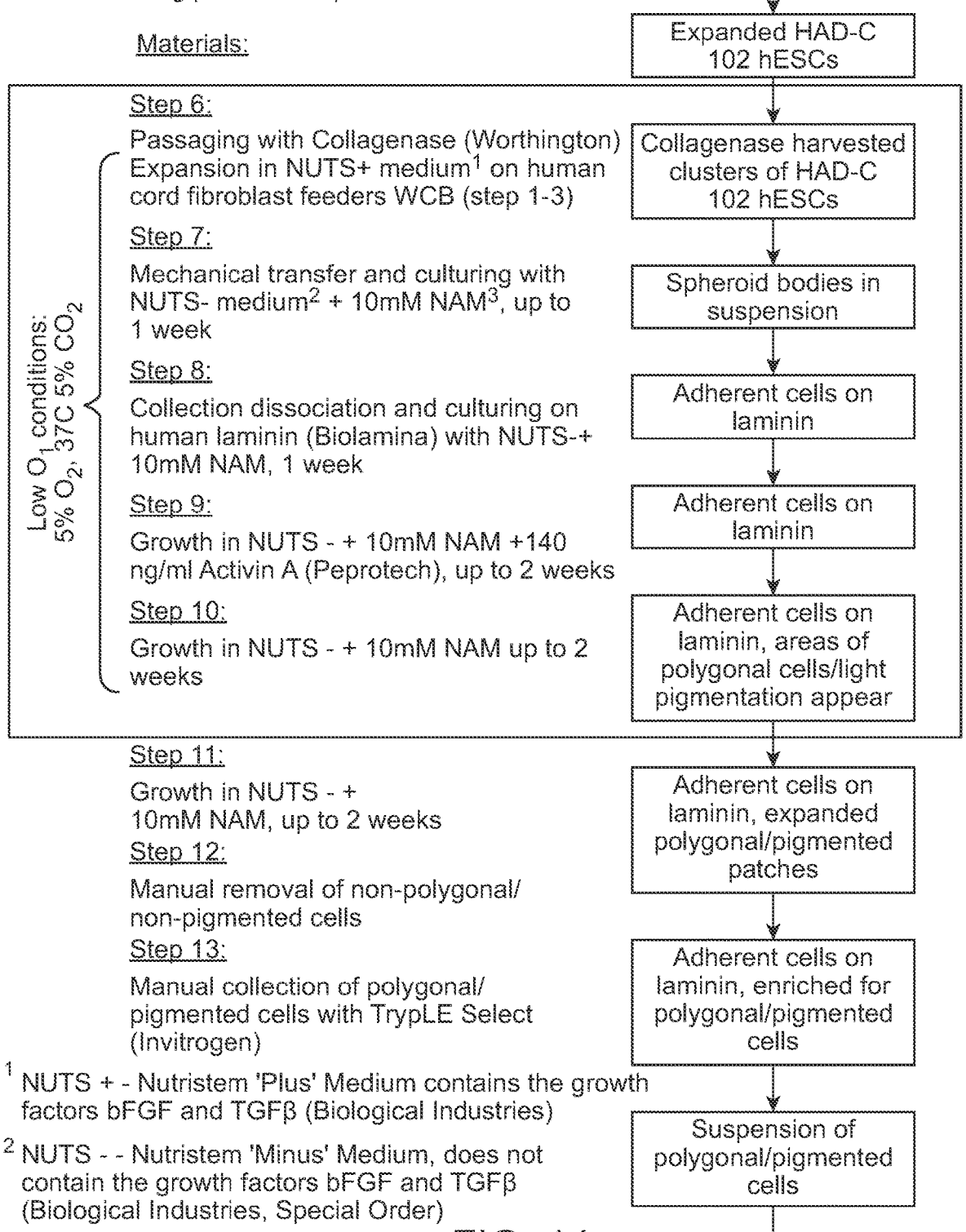
FIG. 14: Manufacturing Process, Steps 6-13: Differentiation into RPE (OpRegen®) cells.

Steps 6-13: Differentiation into RPE cells. Expanded HAD-C102-hESCs were enzymatically treated with collagenase (4152, Worthington) for additional expansion in 6 cm cell culture plates (FIG. 14, Step 6). Expanded HAD-C102-hESCs were then used in the derivation of the OpRegen® DS.

Differentiation of each OpRegen® batch was initiated by mechanical transfer of collagenase A harvested clusters of HAD-C102-hESCs from Step 6 culture to a feeder-free non-adherent 6 cm Hydrocell culture dishes in the presence of Nutristem "Minus" Medium (that does not contain the growth factors bFGF and TGF-β; 06-5102-01-1A Biological Industries, Special Order) supplemented with 10 mM Nicotinamide (N-5535, Sigma) (FIG. 14, Step 7). The plates were then cultured for up to one week under low oxygen atmosphere (5%) conditions (37° C., 5% $CO_2$) to allow the generation of spheroid bodies. Week old spheroid bodies in suspension were then collected, dissociated gently by pipetting, and transferred to human laminin (511, Biolamina)-coated 6-well plates for an additional week of growth under a low oxygen atmosphere (5%) in the presence of Nutristem "Minus" Medium supplemented with 10 mM Nicotinamide (FIG. 14, Step 8). The cells continued to grow under low oxygen (5%) atmosphere for an additional up to 4 weeks; two weeks in the presence Nutristem "Minus" Medium supplemented with 10 mM nicotinamide and 140 ng/ml Activin A (G-120-14E, Peprotech) (FIG. 14, Step 9), followed by up to 2 weeks in the presence of Nutristem "Minus" Medium supplemented with only 10 mM nicotinamide (FIG. 14, Step 10). When areas of light pigmentation became apparent in patches of polygonal cells, plates were transferred back to normal oxygen (20%) atmosphere (37° C., 5% $CO_2$) and were grown for up to 2 weeks in the presence of Nutristem "Minus" Medium with 10 mM Nicotinamide (FIG. 14, Step 11). After up to 2 weeks, expanded polygonal patches with distinctive pigmentation were apparent within areas of non-pigmented cells (FIG. 14, Step 12) and remaining pigmented cells were detached and manually collected following 15 minutes TrypLE Select (12563-011, Invitrogen) treatment at 37° C. (FIG. 14, Step 13). Production Steps 6-13 are depicted in FIG. 14.

Figure 15:
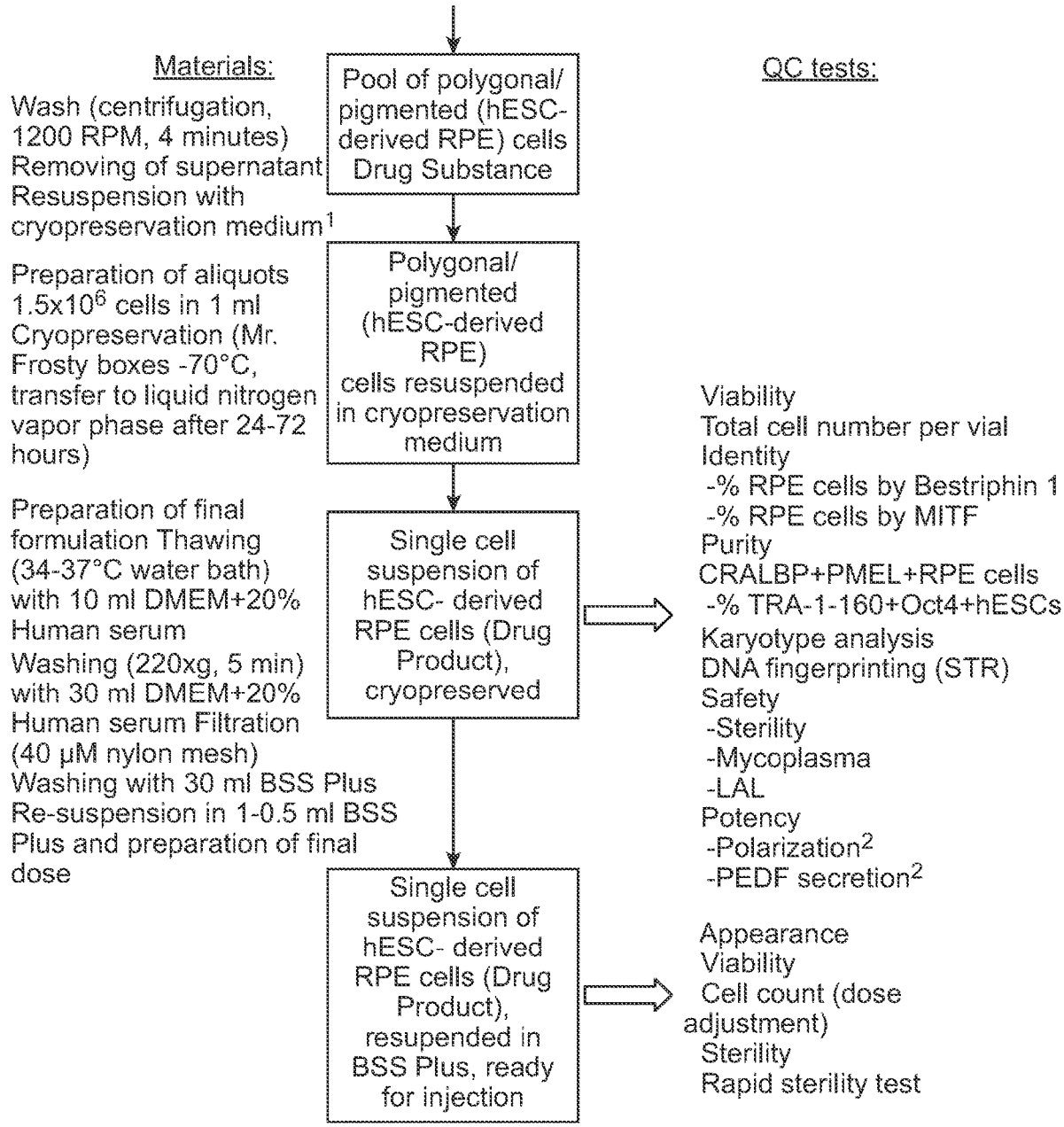
FIG. 15: Manufacturing Process, Steps 14-17: Expansion of pigmented cells.

Steps 14-17: Expansion of OpRegen® cells. Pigmented cells were then transferred to 6-well gelatin-coated plates (0.5-1×10$^6$ cells/plate; P0) for a 2-3 days of growth in the presence of DMEM (SH30081.01, Hyclone) supplemented with 20% human serum (14-498E, Lonza) (FIG. 15, Step 14). DMEM was then replaced with Nutristem "Minus" Medium and cells were grown for 2-3 weeks until the plate was covered with lightly pigmented polygonal cells (FIG. 15, Step 14). These P0 cells were then expanded in gelatin-covered flasks for an additional two passages (P1, P2). Cells at P0 and at P1 were harvested following TrypLE Select treatment at 37° C., washed and cultured for 2-3 days on gelatin-coated flasks in the presence of DMEM supplemented with 20% human serum. DMEM was replaced with Nutristem "Minus" Medium and the cells were grown for 2-3 weeks until the plate was covered with lightly pigmented polygonal cells (FIG. 15, Steps 15-16). Cells at P2 grown in T175 flasks were then harvested following TrypLE Select treatment at 37° C., re-suspended in DMEM supplemented with 20% human serum, pooled and counted.

A sample of growth medium from each batch was taken for sterility, *mycoplasma*, and LAL testing. The cells morphology was observed and documented (FIG. 15, Step 17). Production steps 14-17 are depicted in FIG. 15.

Example 4

Process Control Points

Figure 16:
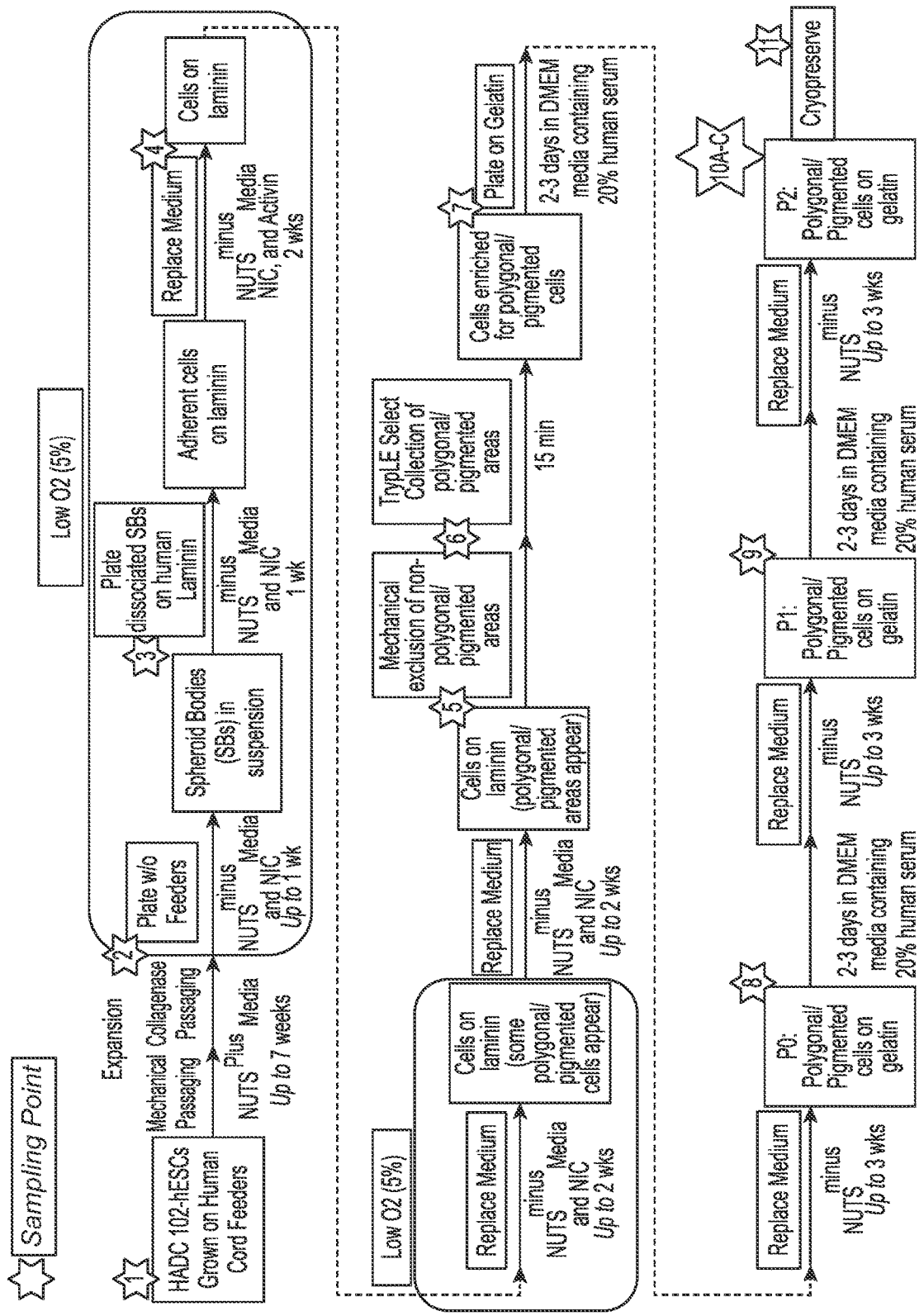
FIG. 16: Detailed OpRegen® manufacturing process and in process control points (yellow stars, IPCs 1-11). (NUTSPlus, Nutristem medium containing bFGF and TGFβ; NUTSMinus, Nutristem medium w/o bFGF and TGFβ; NIC, Nicotinamide; SBs, Spheroid bodies).

IPC points are depicted in FIG. 16. The sampling points chosen to assess hESC impurity and RPE purity along the production process are described below:

IPC point 1: Mechanically expanded HAD-C102 hESCs prior to their differentiation that have normal karyotype. This is the starting material in which the highest level of hESCs is expected. This point was added to evaluate the maximal hESC level prior to differentiation.

IPC point 2: Collagenase expanded HAD-C102 hESCs prior to their differentiation. At this stage, some differentiation is expected, and thereby a reduction in the level of cells expressing Oct4 and TRA-1-60 as well as in the expression level of GDF3 and TDGF. This point was added to evaluate hESC impurity during the phase of non-directed differentiation.

IPC point 3: Spheroid Bodies produced one week post induction of hESC differentiation under feeder free conditions in the presence of Nicotinamide. At this earlier stage of differentiation, hESC impurity during differentiation is expected at the maximal level and thereby this assessment is expected to give an indication for the highest level of safety concern.

IPC point 4: Cells at the end of Activin A treatment. Activin A directs the differentiation towards RPE cells. At this point, a major decrease in hESC impurity and a high increase in expression of RPE markers are expected. This point was added to monitor hESC differentiation to RPE.

IPC points 5-7: Cells at the end of the differentiation process prior and post separation of the non-pigmented areas (IPC point 6) from the pigmented areas (IPC point 7). IPC points 5 and 6 are expected to contain cellular impurities, while sample 7 represents the product at the end of the differentiation process prior to its expansion. Cellular contaminations found in sample 6, may be found is small quantities in sample 7, and in smaller quantities in the product.

IPC point 8: Pigmented cells at P0. Pigmented cells at the end of the differentiation process that were expanded for 2-3 weeks. These cells represent the product two stages prior to the end of the production process.

IPC point 9: Pigmented cells at P1. P0 cells that were expanded for 2-3 weeks. These cells represent the product one stage prior to the end of the production process.

IPC point 10: Pigmented cells at P2 prior to cryopreservation. P1 cells that were expanded for 2-3 weeks are harvested and pooled. These cells represent the drug substance (DS) prior to cryopreservation.

IPC point 11: Cryopreserved pigmented cells at P2. These cells represent the drug product (DP). Throughout production, at all sampling points, cell culture medium was collected for assessment of pigment epithelium derived factor (PEDF) secretion, known to be secreted from RPE cells.

Results

Quantification of TRA-1-60$_+$Oct4$_+$hESCs: The level of hESCs in the various samples collected along the production process was determined using a highly sensitive, robust Oct4/TRA-1-60 double staining FACS method. A week following removal of feeders and growth factors that supports pluripotent cell growth (TGFβ and bFGF), at growth conditions that supports early neural/eye field differentiation, there were only 0.0106-2.7% TRA-1-60$_+$Oct4$_+$ cells (IPC point 3, Spheroid Bodies). Following addition of Activin A that promotes RPE differentiation, the level of TRA-1-60$_+$Oct4$_+$ cells was further deceased to 0.00048-0.0168% (IPC point 4, end of activin), and at the end of differentiation following excision of non-pigmented cells, the level of TRA-1-60$_+$Oct4$_+$ cells was 0.00033-0.03754% (IPC point 7, pigmented cells). At P0, two stages prior to the end of the production process, TRA-1-60+Oct4+ cells in levels of 0.00009-0.00108% (below LOD-close to LLOQ) were detected (IPC point 8). The levels of TRA-1-60+Oct4+ cells at P1 (IPC point 9), P2 prior to cryopreservation (Drug Substance; IPC point 10), and P2 post cryopreservation (DP; IPC point 11) were below assay LLOQ (i.e. 0.00004-0.00047%, 0.00000-0.00016% and 0.00000-0.00020% respectively).

Relative expression of the pluripotency hESC markers GDF3 and TDGF: The relative expression of the pluripotency genes GDF3 and TDGF at the various IPC points along the production process was analyzed. There was a gradual reduction in the expression level of GDF3 and TDGF, which was correlated with the gradual reduction in the numbers of TRA-1-60+Oct4$_+$ cells, along the differentiation process. At the end of P0, two stages prior to the end of the production process, P1, and P2 prior (Drug Substance) and post (Drug Product) cryopreservation, the expression levels of GDF3 and TDGF were similar to the level of expression seen in the negative control OpRegen® 5C cells.

Figure 17:
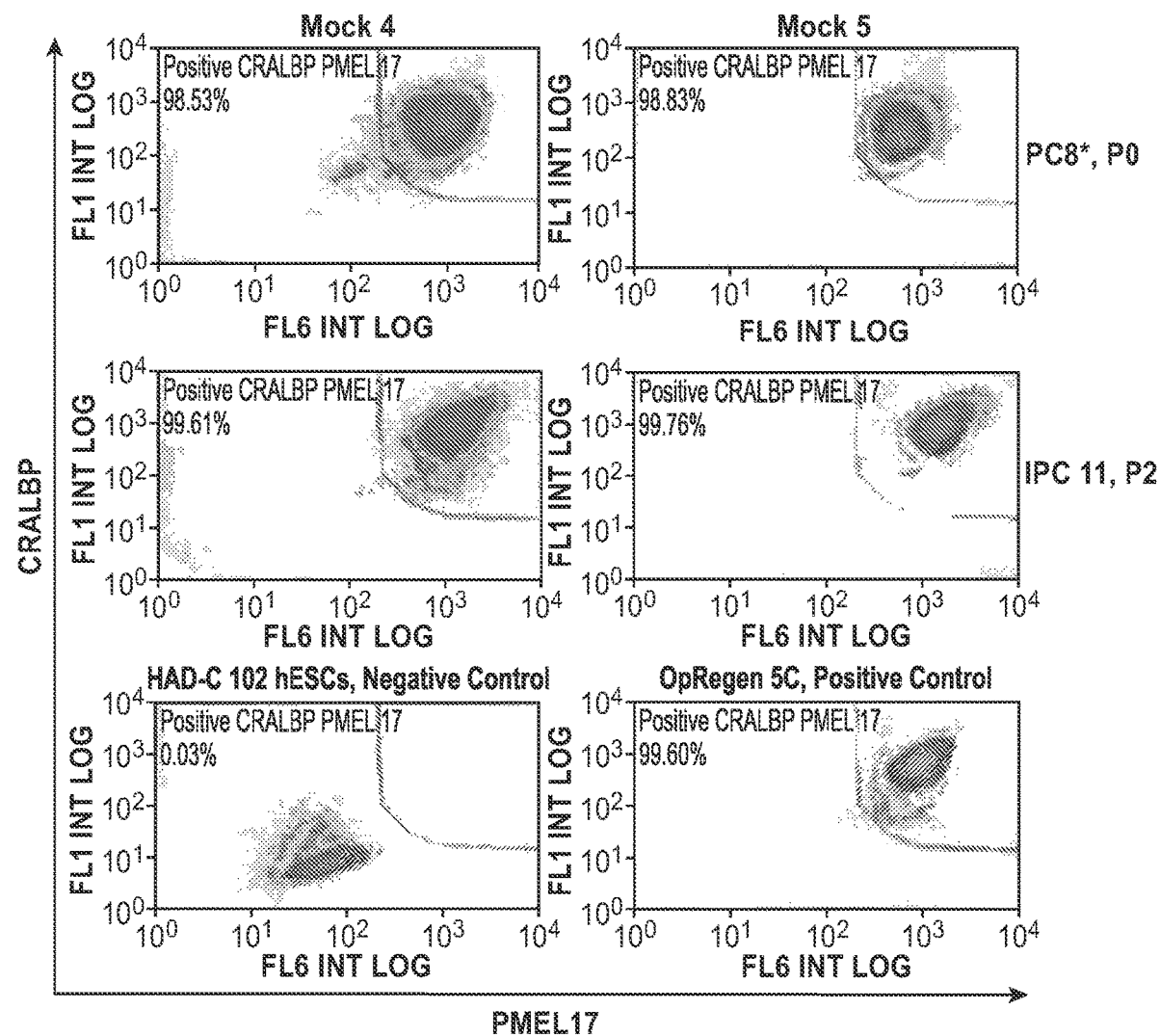
FIG. 17: Level of CRALBP+PMEL17+ RPE cells along OpRegen® Mock production runs 4 and 5. Density plots of IPC points 8 and 11 (*IPC point 8 was tested post cryopreservation) and representative density plots of positive control OpRegen® 5C and negative control HAD-C102 hESCs (range of % CRALBP+PMEL17+ in negative control was 0.02-0.17%). Numbers within each plot indicate percent CRALBP+PMEL17+ cells out of the live single cell gated population. Analysis was done using the FCS express 4 software.

Quantification of CRALBP$_+$PMEL17$_+$ cells: Assessment of CRALBP$_+$PMEL17$_+$ cells for measurement of RPE purity was effected at the end of the differentiation phase, at P0 and P2 (IPC points 8 and 11), respectively), were assessed. As can be seen in Table 3 and in FIG. 17, the level of CRALBP$_+$PMEL17$_+$ RPE purity at P0 (IPC point 8), two stages prior to the end of the production process, was in the range of 98.53-98.83%. Similar level of RPE purity was detected at P2 post cryopreservation (99.61-99.76%; IPC point 11) (Table 3).

TABLE 3

| IPC Point Sampling Time and Stage | | | % CRALBP⁺PMEL17⁺ Cells | | |
|---|---|---|---|---|---|
| IPC | Week | Stage | Mock 4 | Mock 5 | Range |
| 8 | 12 | Pigmented cells at P0* | 98.53 | 98.83 | 98.53-98.83 |
| 11 | 18 | OpRegen ® (P2); DP | 99.61 | 99.76 | 99.61-99.76 |

DP, Drug Product.
*IPC point 8 was tested post cryopreservation. Internal assay controls of RPE cells (OpRegen ® 5C, positive control) spiked into hESCs (HAD-C 102, negative control) demonstrated accuracy error of ≤25%.

Figure 18:
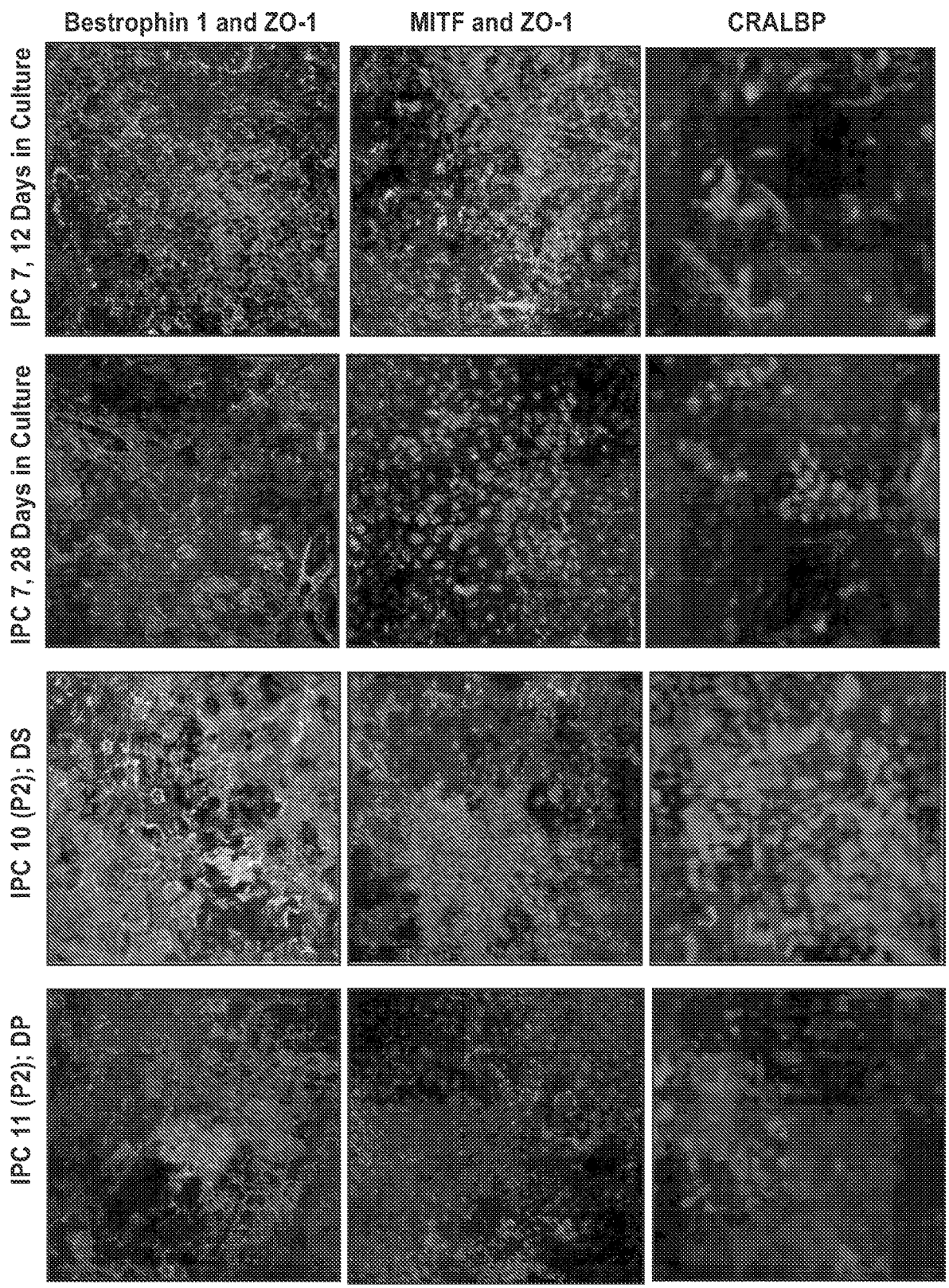
FIG. 18: Immunofluorescence staining of Mock 5 IPC points 7, 10 and 11 with antibodies specific for the RPE markers Bestrophin 1, MITF, ZO-1 and CRALBP.

Confocal imaging of Bestrophin 1, MITF, and CRALBP immunostained cells along Mock production runs 4 and 5: Cells were immunostained for the RPE markers Bestrophin 1, MITF, ZO-1 and CRALBP at the end of the differentiation phase (IPC point 7), at the end of the expansion phase (IPC point 10, DS), and post cryopreservation (IPC point 11, DP). Manually isolated non-pigmented cells (IPC point 6) were plated for immunostaining, but during fixation were detached from the plate and thereby could not be stained. Selected pigmented cells (IPC point 7) plated for 12 days (in mock 5 only, in parallel to cells at P0 from the ongoing production) and for 28 days were positively stained for all tested RPE markers and the percent cells expressing Bestrophin 1 and MITF were 93% and 93.3-96.5%, respectively. Similar levels of Bestrophin 1 and MITF positive cells were detected at P0 (94.9% and 95.9%, respectively; tested only in mock 4), P2 prior cryopreservation, Drug Substance (92.2-92.75% and 93.7-95.5%, respectively), and P2 post cryopreservation, Drug Product (91.1-95.7% and 83.8-94.9%, respectively; decreased MITF immunostaining in mock 5 demonstrate an outlier of the randomly selected area for analysis). CRALBP (as well as ZO-1) expression was detected in all IPC 7, 10 and 11 samples (FIG. 18).

Relative expression of the RPE markers Bestrophin 1, CRALBP and RPE65 along Mock productions 2, 4 and 5: The relative expression of the RPE genes Bestrophin 1, CRALBP and RPE65 at the various IPC points along the production process was measured. There was a gradual increase in the relative expression level of Bestrophin 1, CRALBP and RPE65 along the production process. At the end of Activin A treatment (IPC point 4), that directs the differentiation towards RPE cells, the relative levels of Bestrophin 1, CRALBP and RPE65 were 685, 36, and 325, respectively, fold higher as compared to their relative levels in mechanically passaged hESCs prior to differentiation (IPC point 1; mock 4). The relative expression levels of Bestrophin 1, CRALBP and RPE65 reached a peak from the end of the differentiation stage (IPC points 5) to the P1 stage (IPC point 9). At these stages the respective levels of expression were 5,838-11,841, 211-299, and 5,708-8,687, fold higher as compared to the levels in mechanically passaged hESCs prior to differentiation (IPC point 1).

Figure 11:
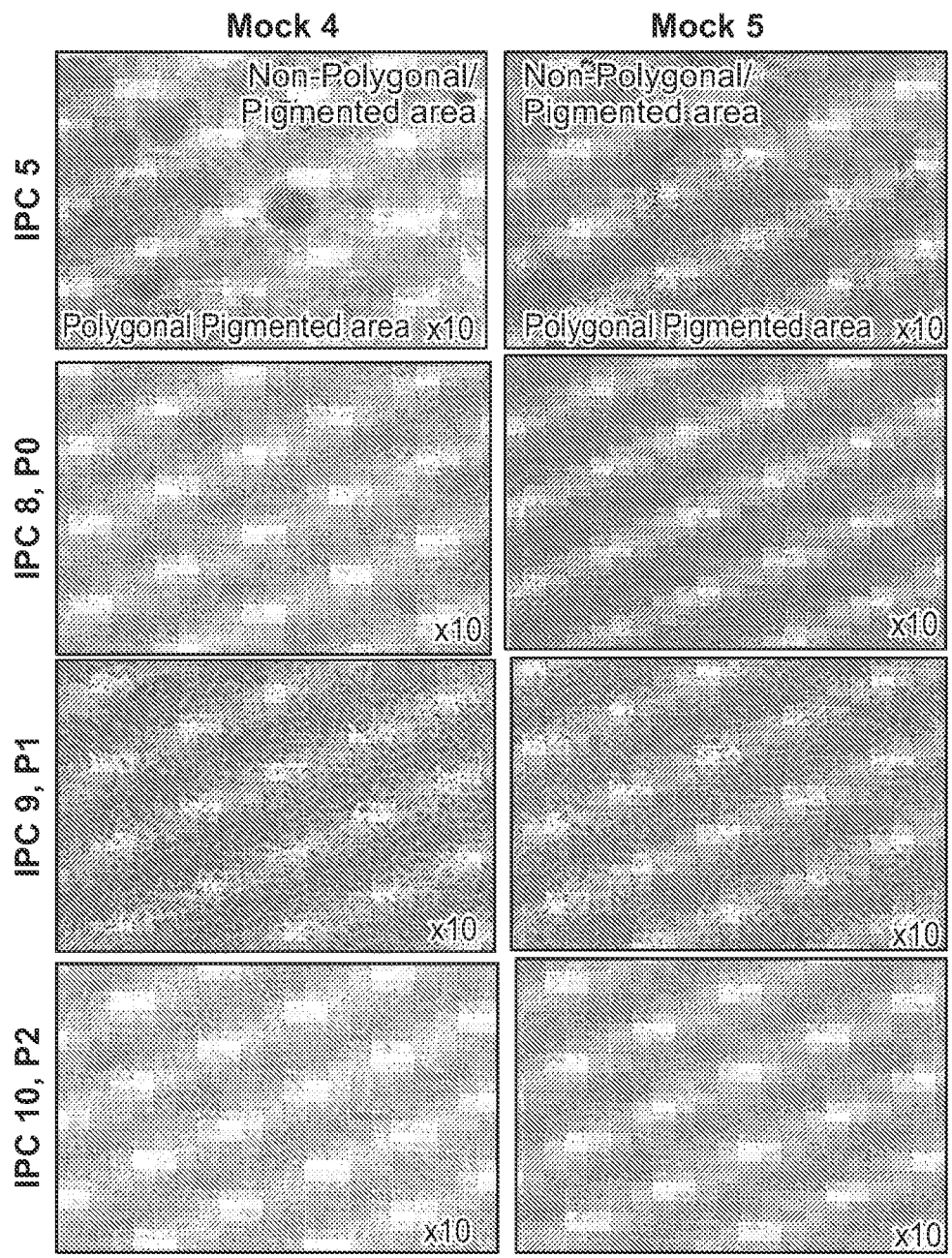
FIG. 11: Morphology results for Mock 4 and 5 at In Process Control (IPC) points 5, and 8-10.

Morphology assessment along Mock productions 4 and 5: Cells were analyzed for morphology at the end of the differentiation phase (IPC point 5) for estimation of the relative area of pigmented cells, and at the expansion phases P0-P2 (IPC points 8-10), to verify confluent polygonal morphology. The relative pigmented cellular area estimated at the end of the differentiation phase prior to excision of the non-pigmented areas (IPC point 5), was 32.5%±13.5% (average±SD, n=7 wells of a 6 well plate) in mock 4 and 60%±13% in mock 5 (average±SD, n=7 wells of a 6 well plate) (see representative images in FIG. 11). Areas of pigmented cells were selected and expanded. Morphology at the end of the expansion phases P0 (IPC point 8), P1 (IPC point 9), and P2 (IPC point 10) demonstrated a densely packed culture with a typical polygonal-shaped epithelial monolayer morphology (FIG. 11).

PEDF secretion and potency measurement along Mock productions 4 and 5: Pigment epithelium-derived factor (PEDF), known to be secreted from RPE cells, was measured in the cell culture medium at various IPC points along mock productions 4 and 5. As can be seen in Table 4, very low levels of PEDF, in the range of 4-79 ng/mL/day, were secreted by hESCs (IPC points 1 and 2) and by spheroid bodies (IPC point 3; end of the first week with Nicotinamide). At the end of Activin A treatment (IPC point 4), that directs the differentiation towards RPE cells, the level of secreted PEDF was in the range of 682-1,038 ng/mL/day, 31-37 fold higher compared to the level secreted by spheroid bodies. Following incubation of cells at normal oxygen conditions with Nicotinamide (IPC point 5), further increase (2.2-4.6 fold) in PEDF secretion to 1,482-4,746 ng/mL/day, was observed. During the expansion phase (P0-P2, IPCs 8-10, respectively), PEDF secreted levels were in the range of 2,187-8,681 ng/mL/day, peaking at P0-P1.

TABLE 4

PEDF secretion along mock productions 4 and 5.

| IPC Sampling Time and Stage | | | PEDF secretion (ng/mL/day) | | |
|---|---|---|---|---|---|
| IPC | Week | Stage | Mock 4 | Mock 5 | Range |
| 1 | 0 | Mechanically passaged hESCs | | | |
|  | 1 | Mechanically passaged hESCs | ND | ND | NA |
|  | 2 | Mechanically passaged hESCs | 4 | ND | NA |
| 2 | 3 | Collagenase passaged hESCs | 21 | 79 | 21-79 |
| 3 | 4 | Spheroid Bodies | 22 | 28 | 22-28 |
| 4 | 7 | Cells at the end of Activin A treatment | 682 | 1,038 | 682-1,038 |
| 5 | 10 | Cells at the end of differentiation | 1,482 | 4,746 | 1,482-4,746 |

TABLE 4-continued

PEDF secretion along mock productions 4 and 5.

| IPC Sampling Time and Stage | | | PEDF secretion (ng/mL/day) | | |
|---|---|---|---|---|---|
| IPC | Week | Stage | Mock 4 | Mock 5 | Range |
| 8 | 12 | Pigmented cells at P0 | 7,523 | 7,951 | 7,523-7,951 |
| 9 | 14 | Pigmented cells at P1 | 8,681 | 7,287 | 7,287-8,681 |
| 10 | 16 | OpRegen ® (P2); DS | 2,187 | 5,147 | 2,187-5,147 |
| 11 | 18 | OpRegen ® (P2); DP | 2,462 | 3,936 | 2,462-3,936 |

ND, Not done;
NA, Not Applicable;
DS, Drug Substance;
DP, Drug Product.

Tight junctions generated between RPE cells enable the generation of the blood-retinal barrier and a polarized PEDF and VEGF secretion. PEDF is secreted to the apical side where it acts as an anti angiogenic and neurotropic growth factor. VEGF is mainly secreted to the basal side, where it acts as a proangiogenic growth factor on the choroidal endothelium. RPE polarization (barrier function and polarized PEDF and VEGF secretion) was measured in a transwell system at the end of P0 (IPC point 8), end of P2 prior to cryopreservation (TPC point 10), and end of P2 post cryopreservation (TPC point 11). As can be seen in Table 5, harrier function/trans-epithelial electrical resistance (TEER) and polarized secretion of PEDF and VEGF were demonstrated at all IPC points.

OpRegen® produced in mock run 2 was not cryopreserved, and thereby could not be tested.

Conclusion

Three mock production runs (mock runs 2, 4, and 5) were carried out under research grade conditions using the same GMP-production methods, xeno-free GMP-grade cells (HAD-C102 hESCs grown on irradiated CRD008 feeders), xeno-free GMP grade reagents and GMP grade lab-ware that were used in the GMP production of the clinical batches. Mock productions 2, 4 and 5 aimed at assessing the level of hESC impurity along the production and Mock productions 4 and 5, also aimed at identifying important in process quality controls.

TABLE 5

| | | | | | | | | Polarization | | | |
|---|---|---|---|---|---|---|---|---|---|---|---|
| IPC Point Sampling Time and Stage | | | PEDF Day 14 (ng/mL/day) | | Transwell-TEER (Ω) at Week 3 | | Transwell-PEDF ratio at Week 3 (Apical/Basal) | | Transwell-VEGP ratio at Week 3 (Basal/Apical) | | |
| IPC | Week | Stage | M4 | M5 | M4 | M5 | M4 | M5 | M4 | M5 | Range |
| 8 | 12 | Pigmented cells at P0 | 1,985 | 3,292 | 768 | 933 | 6.01 | 6.72 | 3.01 | 3.09 | PEDF D14: 1,985-3,292 TEER: 768-933 PEDF ratio: 6.01-6.72 VEGF ratio: 3.01-3.09 |
| 10 | 16 | OpRegen ® (P2); DS | 1,754 | 4,250 | 819 | 941 | 5.72 | 4.72 | 2.54 | 2.73 | PEDF D14: 1,754-4,250 TEER: 819-941 PEDF ratio: 4.72-5.72 VEGF ratio: 2.54-2.73 |
| 11 | 18 | OpRegen ® (P2); DP | 2,462 | 3,936 | 688 | 616 | 6.78 | 3.93 | 2.57 | 2.74 | PEDF D14: 2,462-3,936 TEER: 616-688 PEDF ratio: 3.93-6.78 VEGF ratio: 2.57-2.74 |

ND, Not Done;
DS, Drug Substance;
DP, Drug Product.
PEDF and VEGF were measured by ELISA.
PEDF day 14 was collected from the cells during their culture in a 12-well plate.
Cells were then passaged onto a transwell and cultured for 6 weeks, during which TEER, and secretion of VEGF and PEDF front the basal and apical sides of the transwell were measured Batch Release Testing of RPE cells produced in Mock runs 4 and 5: To verify that OpRegen® produced in mock runs 4 and 5, is comparable to GMP produced OpRegen®, abbreviated OpRegen® batch release testing was carried out that included morphology testing at the end of P2 prior to cryopreservation (IPC point 10, DS), and viability, total cell number/cryovial, identity (expression of Bestrophin 1 and MITF), hESC impurity, and karyotyping at the end of P2 post cryopreservation (TPC point 11, DP). OpRegen® produced in Mock runs 4 and 5 passed hatch release criteria.

Using a qualified TRA-1-60/Oct4 double staining FACS method (LOD 0.0004%, 1/250,000 and LLOQ of 0.001%, 1/100,000) and a qualified flow cytometer, hESC impurity in level below assay LOD was observed at the end of the differentiation phase, in the negatively selected pigmented cells, three stages prior to the end of Mock 5 production process. In mock runs 2 and 4, performed prior to assay qualification using core facility flow cytometer, the level of hESC impurity was below assay LOD two stages prior to the end of the production process. In support with this data, quantitative RT-PCR analysis demonstrated down regulated expression of the pluripotent hESC genes GDF3 and TDGF to levels similar to the negative control (OpRegen® 5C cells) two stages prior to the end of the production process.

Identity testing performed three stages prior to the end of production (isolation of pigmented cells) demonstrated expression of Bestrophin 1 and MITF by 93% and 96.5% of the immunostained cells, respectively, as well as expression of CRALBP and ZO-1 (not quantified). RPE purity testing performed one stage later (i.e. P0, 2 stages prior to the end of the production process), following one expansion cycle of the negatively selected pigmented cells, showed that >98.5% of the cells were $CRALBP_+PMEL17_+$ double positive by FACS. Similar level of RPE purity (i.e. >99.6%) was also detected in the drug product. These results were supported by morphology testing demonstrating typical polygonal shaped epithelial monolayer morphology and by quantitative RT-PCR analysis demonstrating upregulated expression of the RPE genes Bestrophin 1, CRALBP, and RPE65 to levels similar to the positive control (OpRegen® 5C cells).

PEDF, known to be secreted from RPE cells, was measured in the cell culture medium at various stages along the production process of mock runs 4 and 5. At the end of the Activin A treatment (IPC point 4), previously shown by Idelson et al. 2009) to direct the differentiation towards RPE cells, the level of secreted PEDF was highly increased (31 fold in mock 4 and 37 fold in mock 5) relative to the previous production step (induction of spheroid bodies). PEDF secretion levels continued to increase and peaked at P0-P1 (1.7-5.8 fold increase relative to the levels after Activin A). Assessment of the relative area of pigmented cells at the end of the differentiation process (IPC point 5) was identified as another important quality control measure for assessment of RPE differentiation. Using this measure, a 2 fold difference in the yield of pigmented cells in mock 4 and 5 runs (32.5% in mock 4 and 60% in mock 5) was observed, that was correlated with a similar difference seen in PEDF secretion at this stage (1,482 ng/ml/day in mock 4 and 4,746 ng/ml/day in mock 5).

In conclusion, no $TRA-1-60_+Oct4_+$ hESC impurity observed as early as 3 stages prior to the end of the production process. This was correlated with low expression levels of GDF3 and TDGF, high expression levels of Bestrophin 1, CRALBP and RPE65, and high levels of Bestrophin 1 and MITF single positive cells, as well as high $CRALBP_+PMEL17_+$ double positive cells (tested one stage later). Important safety and efficacy IPCs were identified at critical production stages.

Example 5

Efficacy Assessment

Experimental set-up: The present inventors examined whether subretinal transplantation of the RPE cells generated as described in Example 4 could delay the progression of RDD in the Royal College of Surgeons (RCS) rat model.

25,000, 100,000 or 200,000 RPE cells were transplanted into the subretinal space of one eye of RCS rats on post-natal day (P)21-23 (prior to photoreceptor death onset); BSS+ (Alcon) treated and naïve untreated animals served as controls. Groups were separated into 4 survival ages: post-natal day P60, P100, P150 and P200. Fundus photography was used to identify bleb formation and monitor injection quality. Funduscopy was also performed at P60, P100, P150 and P200. Optomotor tracking was used to measure visual acuity of all animals at all time points (P60, P100, P150, P200).

Focal and full field ERGs were assessed in all study groups at P60 and P100. At the assigned sacrifice date for each animal, both eyes were removed, fixed in 4% paraformaldehyde, cryopreserved, embedded in Optimum Cutting Temperature compound (OCT) and cryosectioned. Cresyl violet staining was used to identify and enumerate photoreceptor structural rescue. Immunofluorescent staining (IF) was used to identify transplanted cells, assess their fate, their state of proliferation, and their ability to phagocytose photoreceptor outer segments. In addition immunofluorescent was used in measurement of host cones rescue.

The study design is summarized in Table 6 herein below.

TABLE 6

| GRP # | TREATMENT GROUPS Article | Total # of Cells | TIME OF SACRIFICE POST INJECTION Number of Mice (male and female) at Study Initiation | | | |
|---|---|---|---|---|---|---|
| | | | P60 | P100 | P150 | P200 |
| 1 | Untreated | None | 13 | 11 | 13 | 10 |
| 2 | Vehicle Control | None | 15 | 13 | 16 | 17 |
| 3 | RPE Low Dose | 25,000 | 15 | 15 | 16 | 14 |
| 4 | RPE Medium Dose | 100,000 | 15 | 15 | 18 | 13 |
| 5 | RPE High Dose (MFD) | 200,000 | 15 | 16 | 15 | 13 |

Materials and Methods

Cell counts: Cells were counted before being aliquoted into appropriate dosage concentrations. Pre-injection cell viability for all injection time points averaged 94.0%±0.03. Post injection cell viability averaged 92.4%±0.02.

Surgery: A small incision was made through the conjunctiva and sclera using incrementally smaller gauge needles: 18, 22, 25, and 30. A lateral margin puncture of the cornea was used to reduce intraocular pressure, to reduced egress of the injected cells. The glass pipette was then inserted into the subretinal space and 2 μl of suspension injected. The sclerotomy was then sutured closed. Successful injection of the cells or buffer alone (BSS+) was confirmed first by manual visualization of a subretinal bleb, which was subsequently photographed through the use of a fundus camera (Micron III).

Optokinetic tracking thresholds: Optokinetic tracking thresholds were measured and recorded in a blinded fashion. Repeated measures ANOVA or one-way ANOVA with Fisher's LSD post hoc analysis was used to analyze OKT data.

Electroretinagram (ERG): Two forms of ERGs were measured: an exploratory form of focal ERG where a small spot of light is used to stimulate a localized area of retina, and a standard style of full field ERG where the entire visual field is stimulated.

Histology and Immunohistochemistry: Both eyes from each animal were harvested, fixed, cryoprotected, embedded, and frozen. Frozen blocks were cryosectioned at 12 μm. Approximately 60 slides containing 4 sections per slide were obtained.

Cresyl Violet: Cresyl violet stained sections were examined for: 1) injection site and suture, 2) evidence of photoreceptor rescue, 3) evidence of transplanted cells, 4) untoward pathology. For each slide, maximum outer nuclear layer thickness was also recorded for quantification of rescue.

Immunofluorescence (IF): RPE cell treated eye slides selected for IF were chosen from cresyl violet stained sections that contained cells in the subretinal space consistent with the size and morphology of the transplanted human cells. In addition, protection of the host ONL was used as a secondary criterion. All IF staining was performed as dual stains with DAPI serving as a background nuclear stain. At least one slide from every cell treated animal was used for each run.

Run #1 was performed using rabbit monoclonal Anti-Melanoma gp100 (PMEL17, Clone EPR4864; human specific, Abcam cat #ab137062) co-stained with mouse monoclonal Anti-Nuclei Marker (HuNu, Clone 3E1.3, Millipore, cat #MAB4383) for detecting human RPE and non-RPE cells.

Run #2 was performed using rabbit monoclonal Anti-Ki67 (Ki67; Clone EPR3610, human specific, Abcam, cat #ab92742) and Anti-Nuclei Marker for detecting human proliferating cells.

Run #3 was performed using rabbit polyclonal Anti-rat Cone Arrestin (Millipore cat #ab15282) to evaluate sections for cone counting (see Section 6.8.3). In addition, selected slides were stained using mouse monoclonal Anti Rhodopsin (Clone Rho 1D4, Millipore, MAB5356) in combination with PMEL17 to identify transplanted human cells containing host rhodopsin/outersegments as a measure of their phagocytic activity.

Cone Counting: Confocal z-stack images were acquired from sections of retina obtained from all cell transplanted eyes and from age-matched saline injected controls. Sections from cell injected eyes were chosen in the area of photoreceptor rescue as defined using the previously evaluated cresyl violet stained sections. Cones were counted by 3 observers in a blinded fashion. The three counts were then averaged and counts compared between dosage groups and age.

Rhodopsin ingestion: A potential mechanism of rescue employed by the transplanted cells is to ingest photoreceptor outer segments and shed debris. Removal of the debris zone reduces the toxic stress on the photoreceptors and thus, aids in sustaining photoreceptor survival. Here, the present inventors selected specific animals for evaluation of rhodopsin ingestion by the RPE cells based on the cell survival and photoreceptor protection indices. This evaluation was performed using immunofluorescence.

Results

Figures 19A, 19B, 19C:
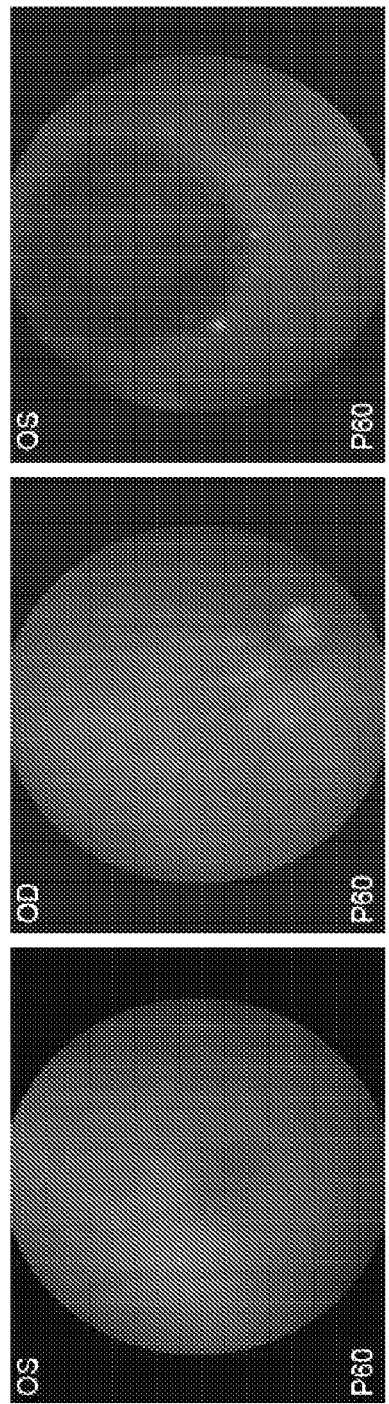
FIGS. 19A-C: Representative color fundus photograph of group 2 (BSS+.

Fundus Imaging: Fundus images collected at necropsy of cell treated eyes revealed hyper and hypo-pigmented areas of the retina that corresponded to the location where subretinal blebs were formed during surgery; the location at which cells were deposited in the subretinal space (FIGS. 19A-C). These patchy areas were not evident in BSS+ injected or non-injected eyes.

Figure 20:
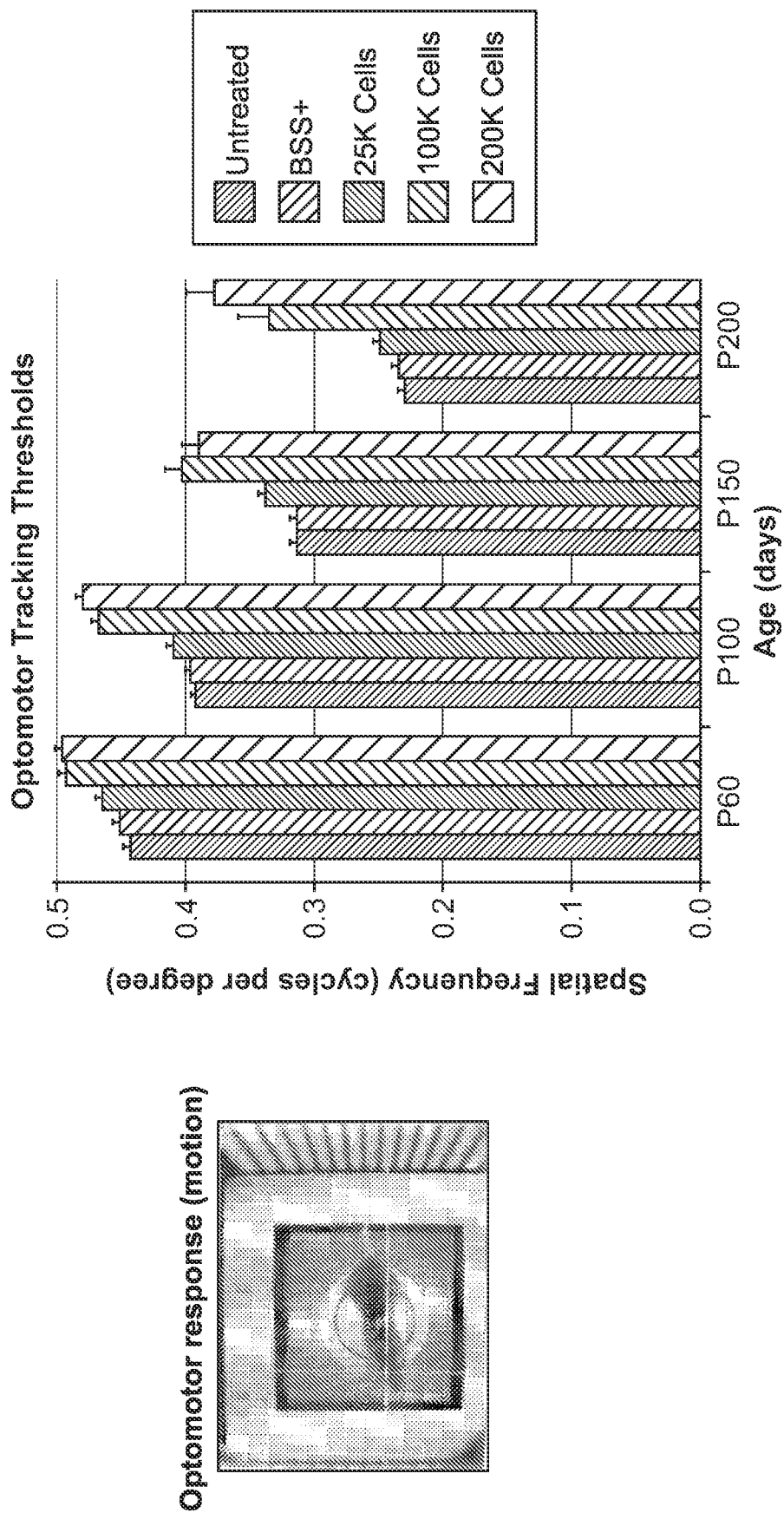
FIG. 20: Optokinetic tracking acuity thresholds measured at P60, P100, P150, and P200. Cell treated groups (group 3—25,000, group 4—100,000 and group 5—200,000) outperformed all controls with the group 4 (100,000) and 5 (200,000) close achieving the best rescue. Contralateral unoperated eyes were equivalent to group 1 (untreated) and group 2 (vehicle control/BSS+) (not shown).

Optokinetic tracking thresholds: OKT thresholds were rescued in all cell treated groups at all ages (FIG. 20). Cell-treated groups outperformed un-operated or saline injected eyes at all ages. There was a significant dose dependent effect between the low dose (25K) and the two larger closes (100K ($p<0.0001$) and 200K ($p<0.0001$)), especially at the later ages, but no clear benefit to the OKT from the high dose (200K) over the intermediate (100K) close was observed ($p=0.5646$). While OKT thresholds were rescued in all cell treated groups, the absolute visual acuity values slowly declined with time. Untreated and saline injected animals' OKT thresholds continue to decline over the course of the study. BSS+ injected eyes were not different from naïve untreated group ($p=0.6068$) and untreated fellow eyes.

Figures 21A, 21B:
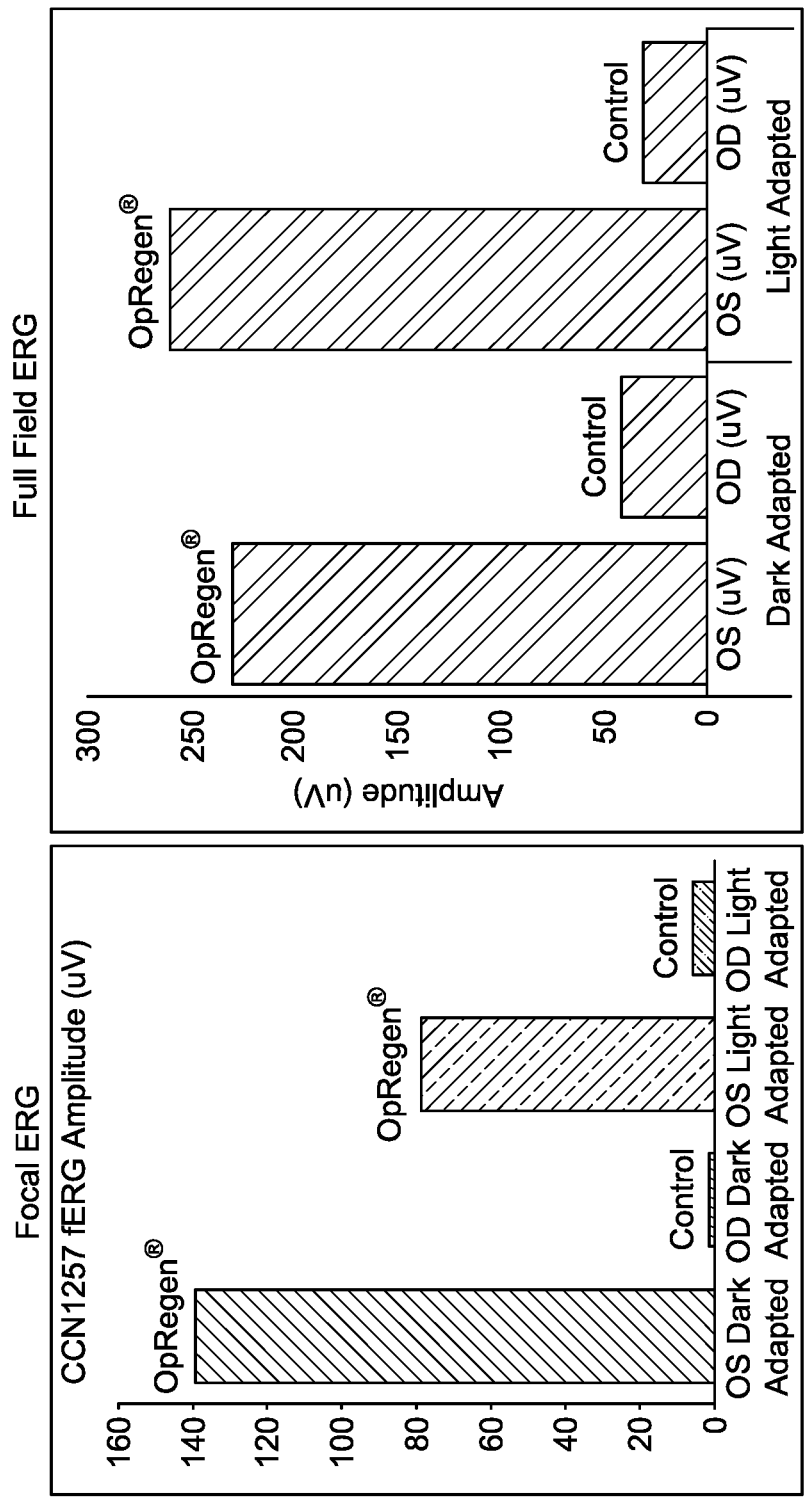
FIGS. 21A-B: Graphs illustrating the Focal (FIG. 21A) and Full field (FIG. 21B) results for a representative rat.

Focal ERG: Focal ERG's were measured in all (n=252) experimental rats at ~P60. Individual animals treated with RPE cells performed well and significantly outperformed controls, as illustrated in FIG. 21A.

Full field ERG: Full field ERG's were measured from 125 RCS rats at P60 and from 63 RCS rats at P100. Individual animals treated with RPE cells performed well and significantly outperformed controls, as illustrated in FIG. 21B.

Figure 22A:
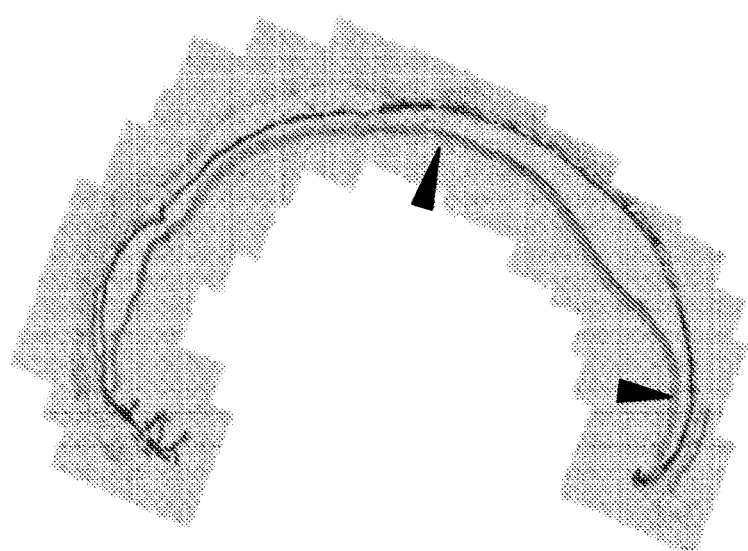
FIGS. 22A-B.
Figure 22B:
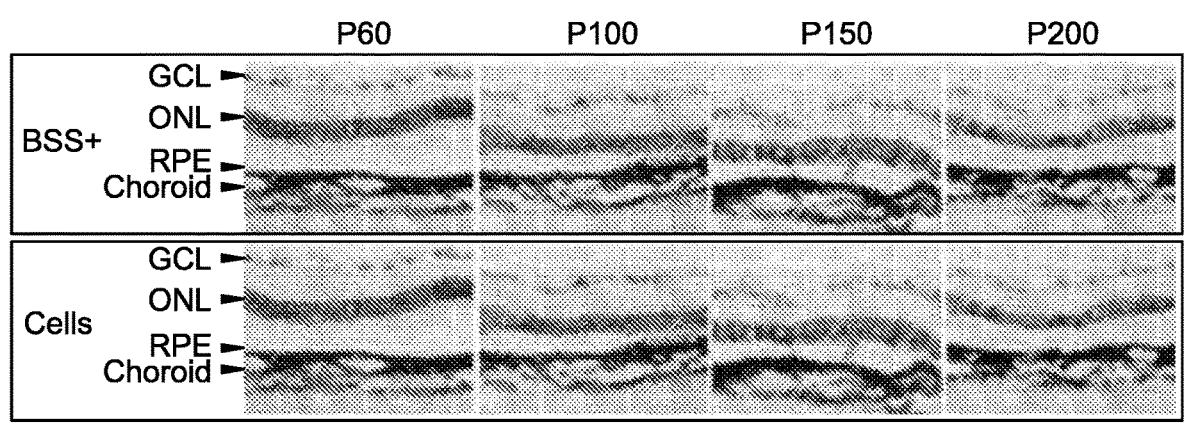

Cresyl Violet staining: An examplary photomontage of a cresyl violet stained section is presented in FIG. 22A. Representative images from BSS+ injected and cell treated (images from multiple groups) eyes are presented in FIG. 22B.

Figure 23:
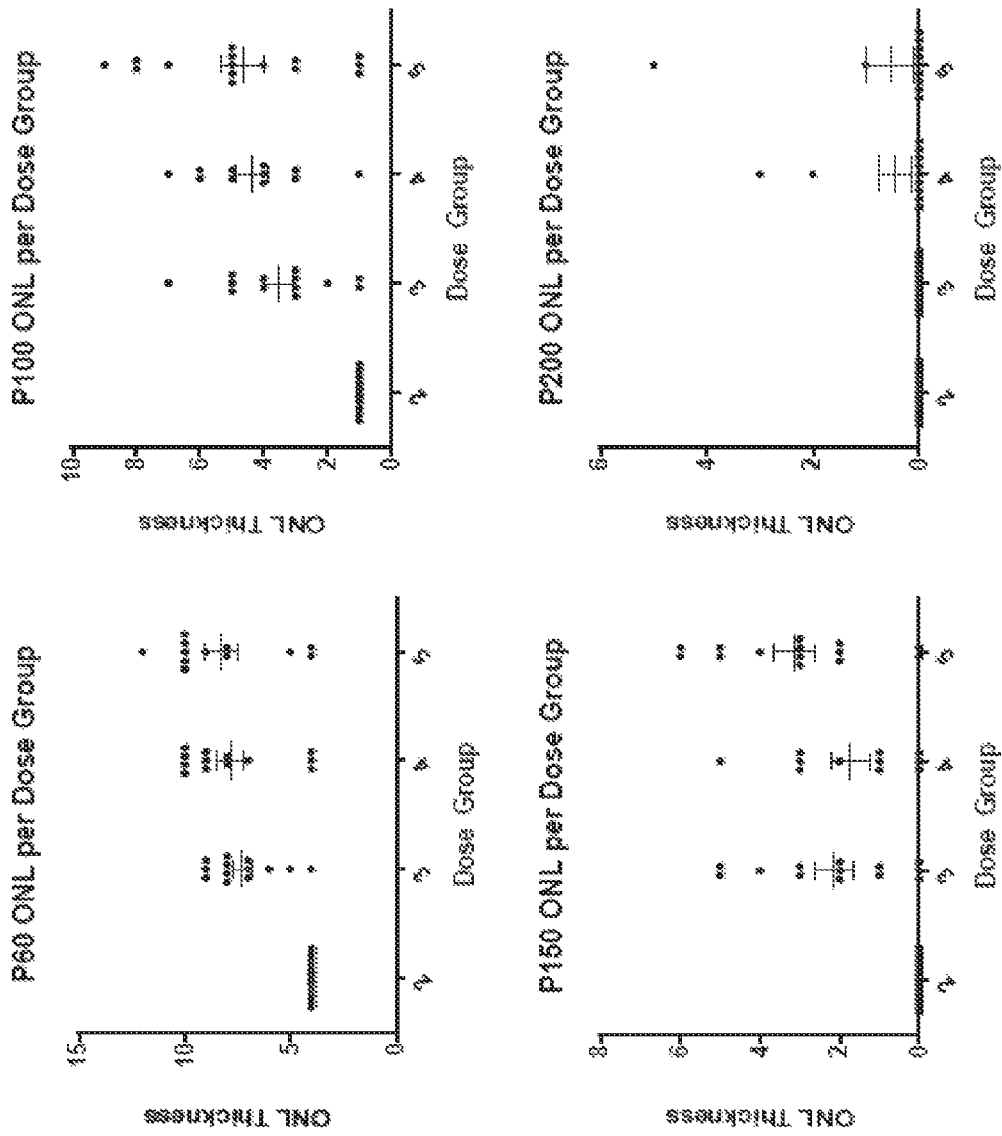
FIG. 23: Outer nuclear layer thickness measured in number of nuclei. Each dot represents the count from each animal from every close group for all ages.

Outer nuclear layer thickness (ONL) was measured as the primary indicator of photoreceptor rescue. Data was recorded as maximum number of photoreceptor nuclei present in each dose group across ages (FIG. 23). Cell treated groups had significantly higher ONL thickness at P60, P100 and P150 (All $p<0.0001$) than BSS+ treated eyes. In terms of percentage of animals with evidence of photoreceptor rescue, 76-92% of animals at P60, 80-90% at P100, 72-86% at P150, and 0-18% at P200 had evidence of photoreceptor.

Immunofluorescence: Transplanted RPE cells were positively identified by immunofluorescence in animals of each survival age (FIG. 24), however, the number of animals with identified cells decreased as age increased. Repeat staining of additional slides in animals that did not originally reveal transplanted cells resulted in additional animals identified with positive cells, but not in all cases.

Figure 24:
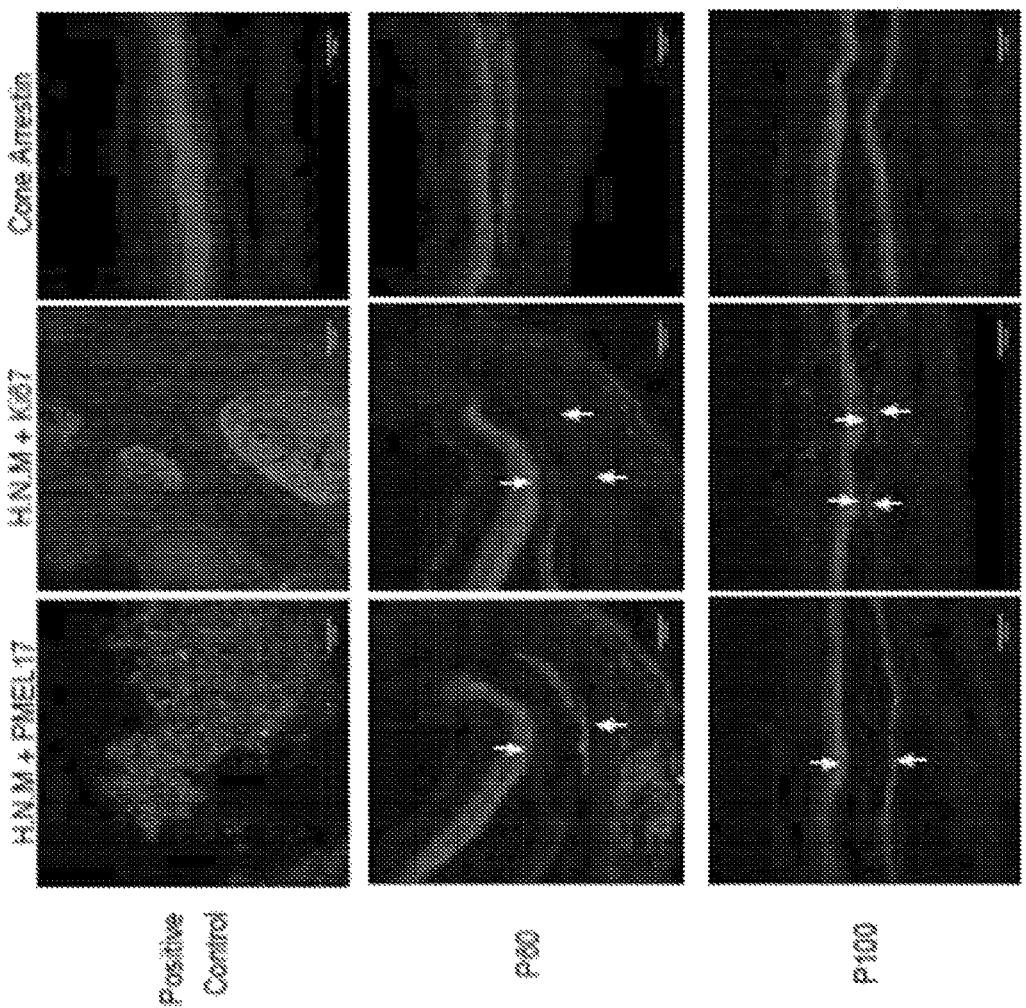
FIG. 24: Immunofluorescent images of positive control tissue and representative experimental cell treated animals at P60, P100, P150, and P200 stained with anti-human nuclei marker (H.N.M, green), anti-pre-melanosomal marker (PMEL17, red), anti-human proliferation marker (Ki67, red), and anti-rat cone arrestin (red). Dapi (blue) is used for background staining to highlight nuclear layers. Human melanoma was used as positive control tissue for PMEL17, human tonsil for Ki67, and juvenile RCS rat retina for cone arrestin. Downward arrows indicate outer nuclear layer; upward arrows indicate positively stained human RPE cells) (OpRegen®, generated as described herein).

Despite not finding transplanted cells in all animals by IF analysis, ONL thickness measurement results indicated 70-90% of cell treated animals had significant photoreceptor rescue, confirmed with OKT rescue, suggesting that most treated eyes contained transplanted cells at some point. The proliferation marker Ki67 was used to identify proliferating human cells. Ki67 positive human cells were not observed (FIG. 24).

Cone Counting: Cone counts in animals that received cell transplants were significantly better than control eyes (FIG. 25; $p=<0.0001$ for each comparison). In general, there was no difference between cone counts across the low, middle and high dosage of cells. A representative image from each age is presented in FIG. 24.

Rhodopsin ingestion: In each case tested (n=6), fluorescently labeled rhodopsin was observed within the transplanted RPE cells (FIGS. 26A-J). This confirms the transplanted cells do ingest outer segment debris post transplantation.

Conclusion

When transplanted into the subretinal space of RCS rats, RPE cells rescued visual acuity in the RCS rat over that of controls at all ages tested. ERG responses were protected when the graft was large enough or in an area of retina accessible for assessment. Rod and cone photoreceptors were rescued in the area of the grafts for up to 180 days post-transplantation. Collectively, this data demonstrates that OpRegen® maintain the functional and structural integrity of the host retina for extended periods. Thus, OpRegen® hold significant potential for the treatment of human RPE cell disorders such as RP and AMD.

Example 6

Stability of RPE Cells

Short-Term Stability

Formulated RPE cells (generated as described in Example 4) in BSS plus were prepared at a final volume of 600-1000

μl per vial. Short term stability was tested at time points 0, 4, 8 and 24 hours. Cells were found stable at all time points.

RPE cell viability and cell concentration were stable at the 8 hour incubation time point for all dose formulations; percent average viability (±SD) for the following concentrations:

These results support OpRegen® cell stability in final formulation at all clinical doses for at least 8 hours when kept at 2-8° C. A safety margin of up to 24 hours exists based on partial data collected (identity, sterility, and medium dose potency).

Results of the short term stability assay are summarized in Table 7 below.

TABLE 7

| TEST | ACCEPTANCE CRITERIA | LOW DOSE 70,000 cells/100 ml | MID DOSE 250,000 cells/100 ml | HIGH DOSE 700,000 cells/100 ml |
| --- | --- | --- | --- | --- |
| Cell Viability | ≥70% | 91 ± 1 (n = 3) | 92 (n = 1) | 91 ± 1.5 (n = 3) |
| Cell Dose | ±40% from initial dose | 91.3 ± 30 (n = 3) | 103 (n = 1) | 104 ± 5.7 (n = 3) |
| MITF Positive Cells | ≥80% | 90 (n = 2) | 93 (n = 1) | 96 (n = 2) |
| Bestrophin 1 Positive Cells | ≥80% | 94 (n = 2) | 92 (n = 1) | 92 (n = 2) |
| CRALBP$^+$PMEL17$^+$ Cells | ≥95% | 99.3 ± 0.15 (n = 3) | 99.5 (n = 1) | 99 ± 0.65 (n = 3) |
| Barrier Function, TER (Ω) | For Information Only | 605 (n = 2) | 724 (n = 1) | 410 (n = 2) |
| Polarized PEDF Secretion (Apical/Basal) | | 3.4 (n = 2) | 3.5 (n = 1) | 4.5 (n = 2) |
| Polarized VEGF Secretion (Basal/Apical) | | 3.3 (n = 2) | 2.2 (n = 1) | 2.3 (n = 2) |
| Sterility USP<71> | Negative | Negative | Negative | Negative |
| Appearance | No foreign particles and/or non-dissociated aggregates | Pass | Pass | Pass |

Low concentration (70×10$^3$ per 100 μl BSS plus) changed from 93%±5 at time point 0 hours to 91%±1 at time point 8 hours, a non-significant decrease.

High concentration (70×10$^3$ per 100 μl BSS plus) changed from 92%±3 at time point 0 hours to 91%±2 at time point 8 hours, a non-significant decrease.

For the medium concentration (250×10$^3$ per 100 μl BSS plus) that was tested there was no significant change throughout the time points.

The overall range for all time points and formulated doses was between 88%-97% from time point 0 hours to 8 hours, when averaging all results for time point 0 hours (93%±3) and time point 8 hours (91%±1) a decrease of 2% was found.

No significant changes in the cell concentration were observed, in either time points or formulated doses. Cell concentration did not change in all 3 studies other than a small decrease seen in one batch in the high dose (2%).

Appearance of the different dose formulations did not change throughout the tested time points; cell suspension was free of foreign particles and non-dissociated aggregates.

Identity and purity of each formulated RPE cell dose at all tested time points were stable up to 24 hours and were within the batch release criteria. At 8 hours (for all formulated RPE cell doses), the level of MITF and Bestrophin positive cells was in the range of 86-97% and 90-94%, respectively, and the level of CRALBP+PMEL17+ double positive cells was in the range of 98.35-99.64%.

Formulated RPE cell doses maintained their potency in all tested time points (4, 8, 24 hours), both secreting high levels of PEDF and forming a polarized RPE monolayer with a polarized secretion of PEDF predominantly to the apical side and VEGF to the basal side. Results for the tested time points 8 hours: TEER was in the range of 376-724 ohms, PEDF apical to basal ratio in the range of 2.77-5.70 and VEGF basal to apical ratio in the range of 2.04-3.88.

Sterility was kept at all incubation time points for all cell dose formulations.

Long-term stability: Three batches of RPE cells were frozen in vapor phase liquid nitrogen. Testing of the long-term stability in cryopreservation started after the freezing date. Results provided are following three years of freezing. The following parameters are being tested: viability, cell number, RPE identity (% Bestrophin 1 and % MITF positive cells), RPE purity (FACS % CRALBP$_+$PMEL17$_+$ RPE cells), potency (polarization and PEDF secretion), karyotype analysis and sterility. At each time point, the required number of vials are thawed and the cells are prepared for the assays as described herein.

Results of the long term stability assay are summarized in Table 8 below.

TABLE 8

| TEST | 0-3 Months | 19-21 Months | 34-36 Months |
| --- | --- | --- | --- |
| Cell Viability | 86 ± 2 (n = 3) | 87 ± 4 (n = 5) | 89 ± 2 (n = 6) |
| Total Cells/Vial | 1.44 ± 0.13 (n = 3) | 1.13 ± 0.2 (n = 5) | 1.13 ± 0.2 (n = 6) |
| Identity: MITF Positive Cells | 84 | 95 | 86 (n = 2) |
| Bestrophin 1 Positive Cells | 91 | 90 | 93 (n = 2) |
| Purity: CRALBP$^+$PMEL17$^+$ Cells | 99.8 | NA | 99.4 |
| Potency: Barrier Function, TER (Ω) | 616 | 368 | 396 ± 200 (n = 3) |
| Polarized PEDF Secretion (Apical/Basal) | 3.93 | 3.86 | 3.05 ± 0.04 (n = 3) |
| Polarized VEGF Secretion (Basal/Apical) | 2.74 | 1.86 | 2.90 ± 0.50 (n = 3) |
| Safety: Karyotyping | Normal | Normal | NA |
| Sterility USP<71> | Negative | NA | NA |

Results

Viability, total cell number/vial and RPE identity were maintained throughout the three year period. In addition, as indicated, data demonstrated potency and purity at levels similar to the ones collected prior to preservation.

A normal karyotype was observed 4 years post cryopreservation. This indicates that long-term storage in vapor phase thus far did not have any deleterious effects on RPE genomic stability.

Sample sterility was demonstrated by testing for the absence of bacterial/fungal growth in all clinical batches at 3 months. Another batch was tested negative 4 years post cryopreservation. Based on these uniformly acceptable stability results, covering a period of three years of stability testing thus far, it is concluded that the RPE cellular product is stable for at least three years when stored at a temperature ≤−180° C. in the vapor phase of liquid nitrogen.

Example 7

Safety and Biodistribution

The objectives of the study were to evaluate survival, biodistribution, and safety of RPE cells (generated as described in Example 4) following subretinal administration in male and female NOD-SCID mice over a 6-month study duration.

NOD-SCID mice (NOD.CB17-Prkdcscid), 5-6 weeks of age at the time of injection, were injected with either BSS Plus (Vehicle Control) or with two doses of RPE cells: $50 \times 10^3$ cells or $100 \times 10^3$ cells (maximal feasible dose), suspended in 1 µL BSS Plus. RPE was administered into the subretina via the transvitreal route (the proposed clinical route of administration) using a 33 G Hamilton needle. A single dose of $50 \times 10^3$ cells or $100 \times 10^3$ cells was injected to one eye, while the fellow eye served as an internal control. Each dosing session contained mice (males and females) from each group. Mice included in the study after pretest, were randomly assigned to the various test groups. Two randomizations were performed. A measured value randomization procedure, by weight, was used for placement into treatment groups prior to vehicle/test article administration. Following administration, animals suitable for use on study were transferred to the target study using a sequential randomization for placement into the final treatment groups. Mice with ocular abnormalities, abnormal clinical observations or weighing less than 16 gram at pretest and mice undergoing non-successful subretinal RPE injection were excluded from the study.

Study Measurements: Assessment of RPE safety in this study was based on animal mortality, clinical observations, body weight, ophthalmologic examinations, clinical pathology (hematology and blood chemistry), gross pathological macroscopic evaluations, organ weights (absolute and relative to body and brain weights), histopathological evaluation of eyes and various organs. Assessment of survival and biodistribution of RPE was performed by histopathological and fluorescence immunostaining evaluations of eyes and various organs and qPCR analysis. The following measurements were performed:
Clinical observation;
Body weight;
Ophthalmologic examinations (including macroscopic and biomicroscopic examinations);
Surgical microscopic examination of subretinal injection quality using the LEICA M80 Stereo microscope (funduscopy);
Complete blood count and blood chemistry;
Necropsy and gross pathology;
Organ weight (absolute and relative to body and brain weights);
Collection, fixation, and paraffin blocking of treated and non-treated contralateral eyes including optic nerve;
Blinded H&E histopathology of eyes and tissues (sternum bone with bone marrow, brain, heart, kidneys, liver, lung, mandibular lymph nodes, spinal cord, spleen, thymus, masses and gross lesions);
Blinded semi quantitation of pigmented cells in H&E stained slides;
Blinded immunostaining of selected slides adjacent to a representative H&E slide demonstrating pigmented cell graft in the eye for a human marker (human nuclei) plus an RPE marker (human PMEL17) and assessment of human RPE and non-RPE cells, human marker (human nuclei) plus a proliferation marker (human Ki67) and assessment of human and non-human proliferating cells, and RPE marker (RPE65) plus proliferation marker (human Ki67) and assessment of RPE and non-RPE human proliferating cells;
Blinded immunostaining of selected slides adjacent to a representative H&E slide demonstrating teratoma, tumor, abnormal cells and lesions for a human marker (human nuclei) to exclude human origin;
Collection and extraction of genomic DNA from blood, bone marrow (collected from femurs), brain, left and right eyes with optic nerves, heart, left and right kidneys, liver, lung, mandibular lymph nodes, ovaries, skeletal biceps femoris muscle, spinal cord, spleen, testes, and thymus and qPCR analysis of human beta globin;
H&E histopathology on tissues (other than the above) found positive for human beta globin in animals from the same group and time point.

Results

There were no RPE-related toxicologic findings in the in-life examinations which included detailed clinical observation, body weight, ophthalmologic examination and clinical pathology comprised of hematology and serum clinical chemistry. The observation of "Eye discolored, dark" in the left eye with an albino background was found in mice treated with pigmented RPE cells at both dose levels in the detailed clinical observation and ophthalmologic examination. Ophthalmologic examination of the surviving animals indicated that this observation consisted of mid-vitreal, darkly pigmented foci. The pigmented foci were distributed randomly along a line extending from the temporal posterior lens capsule to the nasal retinal surface. These foci were interpreted to be RPE cells escaping from the injection cannula upon its removal from the eye following injection, as supported by the vitreal reflux seen during injection or RPE cells leaking into the vitreous humor subsequent to subretinal implantation.

All of the ocular lesions observed on this study were considered to arise secondary to anesthesia, the surgical injection procedure, or incidentally as age-related changes. The finding of multiple pigmented foci within the vitreous humor suggests that RPE cells may be viable within the vitreous body. The presence of pigmented cells in the vitreous body in some of the RPE-treated animals was confirmed at the microscopic level.

In terms of biodistribution as evaluated by qPCR using a set of human beta-globin gene probe/primers, at the 2-week, 2-month, and 6-month intervals, the left eyes treated with $100 \times 10^3$ OpRegen® cells were positive for RPE DNA in 8/12, 11/12, and 16/16 animals with group mean levels at 38, 47 and 249 copies/µg total eye DNA, respectively, indicating a trend of increase over time. There was no significant difference between males and females. In these animals, RPE DNA was not detected in the untreated right eyes and all the non-eye tissues, which included blood, femoral bone marrow, brain, heart, kidneys, liver, lung, mandibular lymph nodes, ovaries, skeletal biceps femoris muscle, spinal cord, spleen, testes, and thymus, except for the spinal cord (27 copies/μg DNA) from one 2-week male animal and the skeletal muscle (16 copies/μg DNA) and spinal cord (below level of qualification) from one 2-week female animal (probably due to inadvertent contamination by exogenous human DNA during DNA extraction from these tissues).

RPE-related macroscopic changes were limited to black discoloration or black foci in the left eye of a few animals at the 2 and 6-month intervals, consistent with in-life clinical observation and/or ophthalmologic examination. These changes correlated to pigmented cells and were not considered adverse as determined by microscopic examination of surviving animals in the high-dose group and of the animals euthanized in extremis and found dead in both dose groups. Pigmented cells were present in the treated left eye in nearly all of the surviving mice examined at each time point in the high dose group (at the subretinal space in 11/12, 12/12 and 16/16 in the 2-week, 2-month, and 6-month intervals), as well as the animals euthanized in extremis or found dead in both low and high dose groups. The most common locations of the pigmented cells were the subretinal space and the vitreous body as confirmed by immunostaining of human cell- and RPE-specific biomarkers. In the subretinal space, pigmented cells tended to be restricted to the injection site at the earlier time points, whereas at the later time points they were present at locations distant from the injection sites, suggesting local cell spreading. There was a slight increase in average total number of pigmented cells per eye at the 6-month time point compared to 2-week or 2-month time points in males. This increased number of pigmented cells of human origin was supported by the qPCR analysis.

Long-term engraftment of the RPE cells is illustrated in FIG. 27A. Pigmented cells stain positive for Human Nuclei and PMEL17 in NOD-SCID subretinal space 9 months post transplant.

FIG. 27B is a photograph illustrating the clustered at the place bleb following injection. FIG. 27C is a photograph illustrating the subsequent spreading of the cells into a monolayer following injection.

RPE was not associated with any organ weight changes. There were no macroscopic and microscopic changes in the untreated right eyes and the non-eye organs examined in this study which included brain, heart, kidneys, liver, lung, mandibular lymph nodes, spinal cord, spleen, and thymus. Anti-human nuclei biomarker antibody stain (Human Nuclei) was observed in 64%, 36%, and 73% of the tested left eyes at 2-week, 2-month, and 6-month time points, respectively, in the animals examined in the high dose group.

The highest detection level for Human Nuclei was noted in pigmented cell populations within the subretinal space followed by the vitreous body. Anti-human RPE-specific biomarker PMEL17 staining was observed in most of the animals tested whereas another RPE-specific biomarker, RPE65, had various levels of detection at the different time points. These RPE-specific biomarkers were mostly detected in the subretinal space and less in the vitreous body. Human cell proliferation biomarker Ki67 was detected in only a few cells in a small number of animals, mainly in pigmented cells within the vitreous body and less within the subretinal space. The incidence of Ki67 positivity decreased over time with only one animal at 6 month. The Ki67-positive cells were not associated with any abnormal morphology.

Several microscopic changes were noted at the injection site across all the time points and all the study groups and considered related to the surgical injection procedure. Some of these changes were slightly more prominent in animals examined in the high dose group at 6 months. For example, retinal detachment was noted in one animal and the incidence or severity of retinal degeneration/atrophy or fibroplasia was slightly increased compared to the vehicle control group.

There were no RPE-dependent effects on animal mortality rate and survival.

Conclusion

No local or systemic toxicologic, lethal, or tumorigenic effects were observed in the NOD/SCID animal model during the 6-month study period following single injection of RPE at dose levels of up to 100,000 cells/μl/eye. Biodistribution of RPE cells was restricted to the treated left eye with local subretinal cell spreading from the subretinal injection site as a function of time. RPE cells were present predominantly in the subretinal space followed by the vitreous body in most of the animals examined in the high dose group at 2-week, 2-month, and 6-month intervals, with variable positivity in immunostaining by antibodies against the human nuclei and/or human RPE-specific biomarkers. The persistence of RPE cells in the eye was estimated to be at least 6 months with very limited cell proliferation. The limited proliferation took place mostly in the vitreous body and had no adverse effects. There was evidence that the number of RPE cells increased in the treated eye over time, although this was accompanied by decreased proliferation incidence in the subretinal population examined. Expression of both RPE specific markers RPE65 and PMEL17 was predominantly in RPE cells within the subretinal space as opposed to those within the vitreous body, where most of Ki67-positive cell incidences were found. The latter suggests that the increase in RPE cells over time is limited to the vitreous space and that the expression of specific RPE65 and PMEL17 RPE markers may be regulated by the microenvironment. In conclusion, based on the data presented above, there are no serious safety concerns related to the injection of the presently described RPE cells as compared to vehicle control group.

Example 8

Expression of Pax-6 in the RPE Cells

Objective: Development of a FACS based method for assessing the level of PAX-6 in human retinal pigment epithelial (RPE) cells.

Materials and Methods

Frozen RPE cells (generated as described in Example 4, were thawed spun down, re-suspended in 1 ml PBS minus, filtered through a 35 μM cell strainer and counted with the NC-200 cell counter. The cell concentration was adjusted to ~1×10$^6$ cells/ml in PBS minus. 1 μl/ml FVS450 was added to each ml cell suspension followed by vortexing and incubation for 6 minutes at 37° C. FVS450 was quenched with 0.1% BSA(-Ig)-PBS minus, and re-suspended in 0.1% BSA(-Ig)-Fc-block (5 min at RT) to block all Fc-epitopes on the cells. Cells were then fixed and stained with anti-Pax-6 antibody (AF647 Cat #562249).

Results

Figure 29:
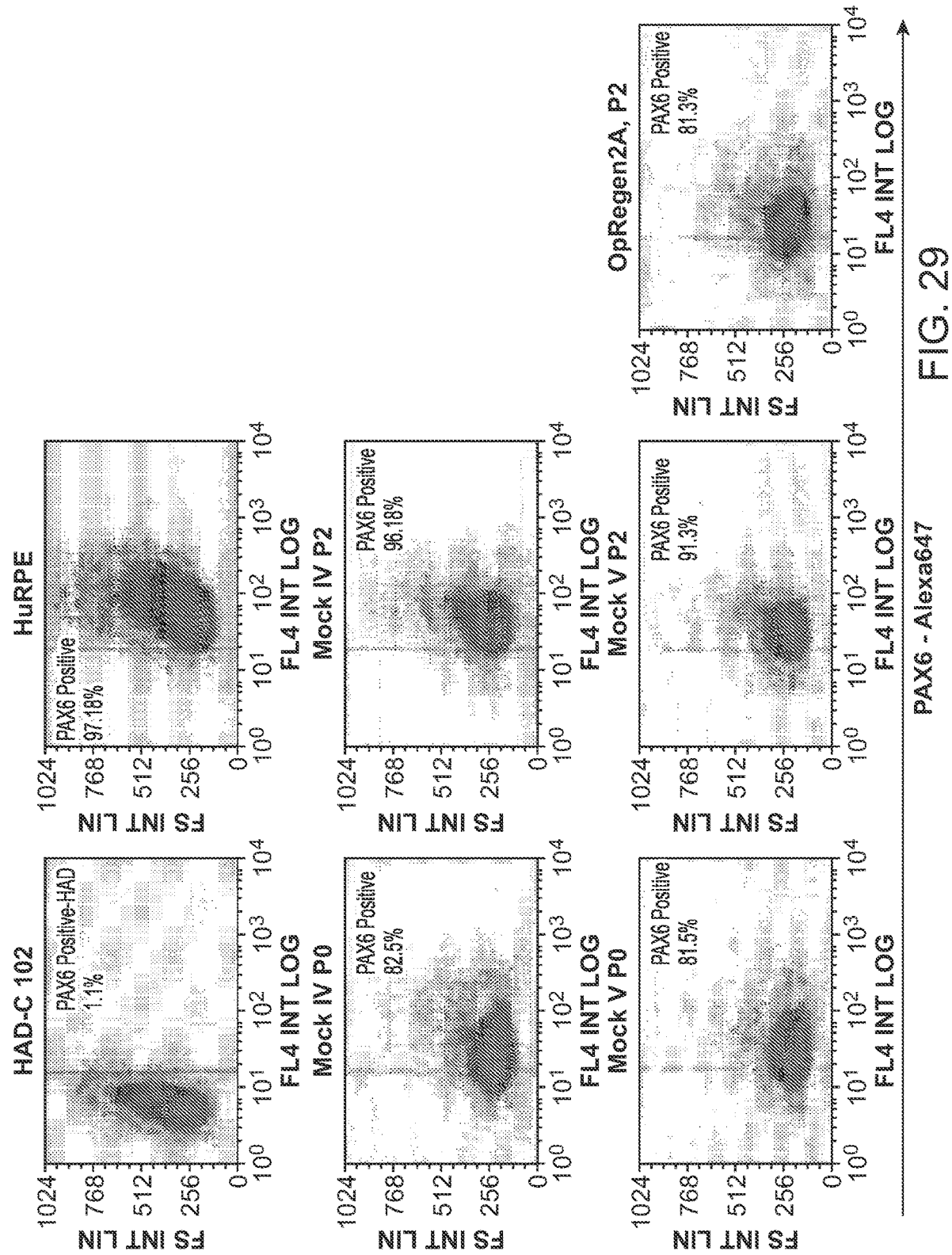
FIG. 29 is the results of the FACS analysis illustrating PAX6 expression in RPE cells generated as described herein (P2-DP, drug product: Mock IV, Mock V, OpRegen® batch 2A; HuRPE: normal human RPE from ScienCell) and along production (P0).
Figure 30:
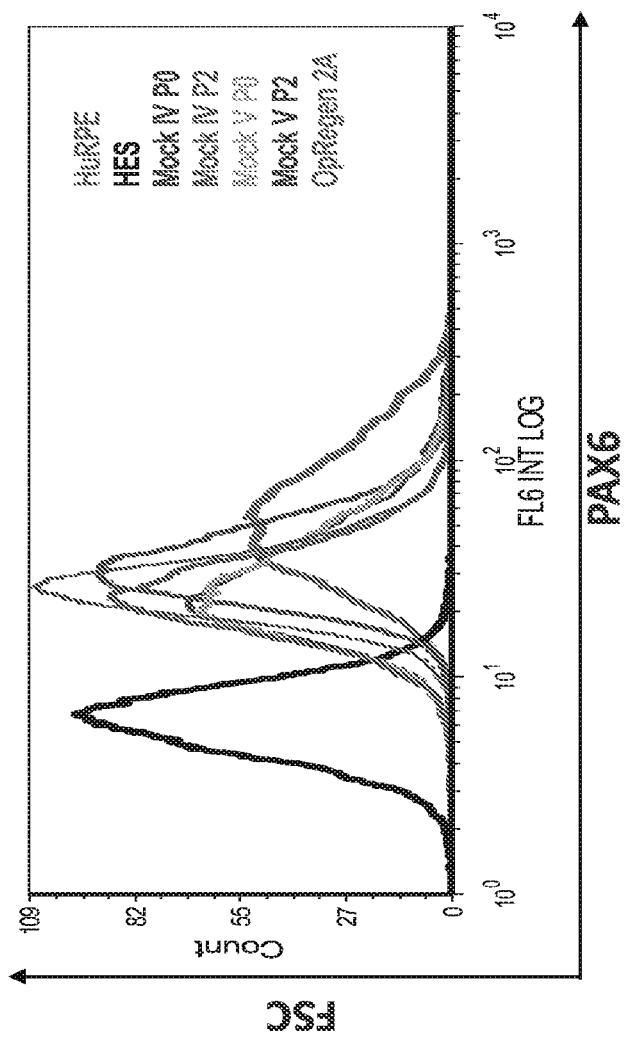
FIG. 30 is a graph illustrating PAX6 expression in OpRegen® cells, as assayed by FACS (HES, human embryonic stem cells used as negative control).
Figure 31:
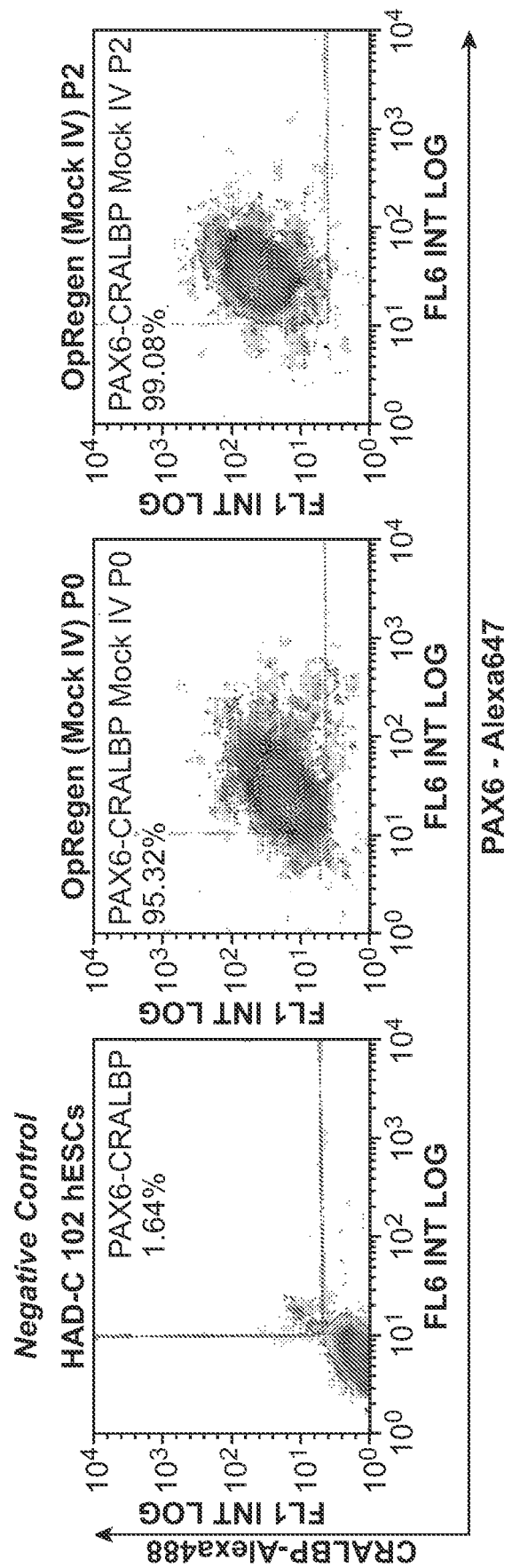
FIG. 31 is the results of the FACS analysis illustrating double staining of PAX6 and CRALBP.

As can be seen in FIG. 29, cells at P0 and P2 are positive for PAX6 (81.5%-82.5% at P0 and 91.3%-96.1% at P2). P2 is the passage at the end of the production process and P0 is two expansion stages earlier. The data was shown to be consistent across hatches, as shown in FIGS. 29 and 30. In addition, the present inventors showed by FACS analysis that the RPE cells double stained for PAX-6 and CRALBP (FIG. 31).

Example 9

Identification of Proteins Secreted by the RPE Cells

Objective: To identify a signature of proteins (known and new) secreted by the OpRegen® (RPE cells) that can be used as a batch release potency assay as well as a process control assay.

Supernatants were collected from RPE cells (generated as described in Example 3) that were cultured under different culture conditions indicated below. Supernatants were then screened using the G6 and G7 RayBiotech arrays according to manufacturer's instructions after an overnight incubation of the supernatants with the related array.
1. RPE drug product cells post thawing cultured for 4 and 14 days on 12-well plate (0.5×10⁶ cells/well at Passage 3) (referred to herein as OpRegen®).
2. RPE drug product cells post thawing cultured for 14 days on 12-well plate and then cultured for 3 weeks on a Transwell (as per AM-RPE-15) and demonstrated TEER>500Ω. Supernatants were taken from the apical and basal chambers.
3. Cells generated according to the protocol described in Example 3, prior (QC3) and post (QC4) Activin A treatment.
4. Nutristem medium (Nut−) without addition of TGFβ and FGF.

Supernatants were also collected from the following cell cultures and tested by ELISA:
1. OpRegen® drug product cells post thawing that were each cultured for 14 days on 12-well plate and then cultured for 3 weeks on a Transwell (as per AM-RPE-15) and demonstrated TEER of 3550 and 5050, respectively. Supernatants were taken from day 14 (passage 3) and from the apical and basal chambers.
2. RPE7 cells post thawing that were cultured for 14 days on 12-well plate (0.5×10⁶ cells/well at Passage 3).
3. Mock VI cells at the end of Passage 1 of the production process that were grown on laminin521 following Enzymatic or Mechanical isolation (as described in Example 3). These cells were tested for potency as per AM-RPE-15 and supernatants were collected from cells at Day 14 on 12 well plate (passage 2) and cells after 3 weeks on transwell from the apical and basal chambers.
4. Fetal HuRPE cells at Passage 3 Days 4 and 14 (0.5×10⁶ cells/well).

ELISA test validation was performed according to manufacturer's instructions related to each ELISA kit. In each protocol, incubation with the supernatants was overnight.

Study design: Supernatants were collected from the cells that were cultured under different culture conditions and kept at −80° C. Following protein array analysis, validation of the hits was measured by ELISA.

Results

The G7 array results are provided in Table 9 herein below.

TABLE 9

| G7 | Nut (−) | Day 4 | Day 14 | TW Apical | TW Basal | QC3 | QC4 |
|---|---|---|---|---|---|---|---|
| POS | 18,132 | 18,132 | 18,132 | 18,132 | 18,132 | 18,132 | 18,132 |
| NEG | 69 | 65 | 15 | 41 | 79 | 23 | 45 |
| Acrp30 | 18 | 4,739 | 46 | 22 | 114 | 102 | 4 |
| AgRP | 56 | 61 | 62 | 72 | 75 | 57 | 94 |
| Angiopoictin-2 | 15 | 35 | 13 | 22 | 32 | 373 | 306 |
| Amphiregulin | 28 | 24 | 32 | 36 | 30 | 27 | 32 |
| Axl | 15 | 30 | 100 | 365 | 29 | 41 | 103 |
| bFGF | 15 | 22 | 23 | 95 | 20 | 211 | 28 |
| b-NGF | 11 | 29 | 31 | 24 | 31 | 61 | 30 |
| BTC | 41 | 58 | 46 | 47 | 54 | 127 | 59 |
| CCL-28 | 37 | 42 | 40 | 36 | 34 | 88 | 60 |
| CTACK | 57 | 58 | 80 | 71 | 79 | 68 | 73 |
| Dtk | 16 | 17 | 17 | 21 | 21 | 23 | 24 |
| EGF-R | 11 | 61 | 174 | 227 | 156 | 138 | 77 |
| ENA-78 | 23 | 34 | 27 | 31 | 34 | 36 | 36 |
| Fas/TNFRSF6 | 19 | 22 | 25 | 24 | 33 | 21 | 23 |
| FGF-4 | 16 | 19 | 19 | 20 | 25 | 14 | 22 |
| FGF-9 | 19 | 17 | 27 | 21 | 27 | 21 | 26 |
| GCSF | 200 | 246 | 235 | 233 | 246 | 245 | 262 |
| GITR-Ligand | 47 | 54 | 52 | 50 | 53 | 46 | 56 |
| GITR | 24 | 26 | 26 | 29 | 29 | 28 | 24 |
| GRO | 121 | 367 | 224 | 952 | 400 | 549 | 472 |
| GRO-alpha | 65 | 61 | 79 | 64 | 77 | 65 | 85 |
| HCC-4 | 50 | 72 | 40 | 38 | 43 | 40 | 85 |
| HGF | 19 | 20 | 20 | 31 | 18 | 239 | 35 |
| ICAM-1 | 13 | 20 | 24 | 27 | 17 | 106 | 56 |
| ICAM-3 | 9 | 14 | 14 | 8 | 12 | 2 | 9 |
| IGFBP-3 | 18 | 22 | 25 | 84 | 24 | 25 | 601 |
| IGFBP-6 | 13 | 172 | 39 | 167 | 59 | 107 | 66 |
| IGF-I SR | 27 | 26 | 27 | 27 | 29 | 23 | 33 |
| IL-1 R4/ST2 | 43 | 36 | 44 | 41 | 45 | 34 | 111 |
| IL-1 RI | 61 | 56 | 50 | 54 | 59 | 48 | 65 |
| IL-11 | 54 | 58 | 51 | 60 | 89 | 55 | 64 |
| IL-12 p40 | 10 | 16 | 13 | 12 | 17 | 18 | 12 |
| IL-12 p70 | 15 | 18 | 27 | 19 | 18 | 18 | 20 |
| IL-17 | 47 | 57 | 67 | 51 | 52 | 50 | 55 |
| IL-2 Rapha | 57 | 67 | 115 | 62 | 66 | 64 | 69 |
| IL-6 R | 12 | 25 | 42 | 15 | 15 | 81 | 18 |

TABLE 9-continued

| G7 | Nut (−) | Day 4 | Day 14 | TW Apical | TW Basal | QC3 | QC4 |
|---|---|---|---|---|---|---|---|
| IL-8 | 107 | 119 | 113 | 237 | 135 | 993 | 226 |
| I-TAC | 14 | 20 | 23 | 18 | 25 | 26 | 24 |
| Lymphotactin | 20 | 26 | 27 | 23 | 24 | 19 | 23 |
| MIF | 27 | 261 | 2,712 | 3,463 | 515 | 4,300 | 3,736 |
| MIP-1alpha | 26 | 24 | 25 | 29 | 27 | 23 | 25 |
| MIP-1beta | 18 | 22 | 20 | 17 | 23 | 28 | 1,056 |
| MIP-3beta | 19 | 21 | 17 | 19 | 23 | 15 | 17 |
| MSP-alpha | 21 | 34 | 26 | 25 | 25 | 37 | 33 |
| NT-4 | 10 | 14 | 11 | 12 | 13 | 9 | 15 |
| Osteoprotegerin | 16 | 48 | 4,622 | 191 | 33 | 830 | 593 |
| Oncostatin M | 40 | 46 | 44 | 52 | 61 | 53 | 39 |
| PIGF | 46 | 111 | 110 | 89 | 75 | 284 | 336 |
| sgp130 | 16 | 93 | 199 | 393 | 40 | 222 | 564 |
| sTNF RII | 13 | 15 | 12 | 13 | 18 | 40 | 10 |
| sTNF-RI | 123 | 449 | 675 | 1,703 | 163 | 293 | 203 |
| TECK | 50 | 61 | 60 | 52 | 54 | 75 | 59 |
| TIMP-1 | 130 | 1,223 | 1,909 | 1,674 | 1,948 | 2,006 | 1,798 |
| TIMP-2 | 15 | 571 | 621 | 1,937 | 753 | 483 | 776 |
| Thrombopoietin | 48 | 48 | 47 | 47 | 48 | 54 | 39 |
| TRAIL R3 | 39 | 100 | 100 | 310 | 56 | 572 | 314 |
| TRAIL R4 | 23 | 22 | 21 | 18 | 21 | 46 | 20 |
| uPAR | 68 | 161 | 67 | 148 | 65 | 276 | 87 |
| VEGF | 14 | 508 | 689 | 559 | 554 | 546 | 592 |
| VEGF-D | 20 | 21 | 23 | 20 | 22 | 25 | 19 |

The G6 array results are provided in Table 10 herein below.

TABLE 10

| G6 | Nut (−) | Day 4 | Day 14 | TW Apical | TW Basal | QC3 | QC4 |
|---|---|---|---|---|---|---|---|
| POS | 12,843 | 12,843 | 12,843 | 12,843 | 12,843 | 12,843 | 12,843 |
| NEG | 18 | 5 | 20 | 8 | 10 | 2 | 12 |
| Angiogenin | 4 | 3,006 | 3,152 | 423 | 1,749 | 2,838 | 3,574 |
| BDNF | 12 | 8 | 12 | 9 | 9 | 8 | 9 |
| BLC | 14 | 17 | 18 | 11 | 17 | 10 | 12 |
| BMP-4 | 9 | 38 | 9 | 9 | 6 | 6 | 6 |
| BMP-6 | 6 | 3 | 4 | 2 | 4 | 3 | 1 |
| CK beta 8-1 | 9 | 7 | 8 | 9 | 10 | 6 | 8 |
| CNTF | 79 | 72 | 68 | 68 | 68 | 75 | 78 |
| EGF | 5 | 8 | 6 | 8 | 7 | 10 | 1 |
| Eotaxin | 9 | 13 | 11 | 11 | 12 | 11 | 12 |
| Eotaxin-2 | 9 | 11 | 8 | 4 | 7 | 7 | 8 |
| Eotaxin-3 | 58 | 53 | 62 | 42 | 59 | 47 | 59 |
| FGF-6 | 7 | 4 | 7 | 1 | 9 | 0 | 7 |
| FGF-7 | 9 | 9 | 16 | 14 | 13 | 9 | 14 |
| Flt-3 Ligand | 49 | 51 | 50 | 46 | 54 | 49 | 46 |
| Fractalkine | 6 | 3 | 6 | 4 | 4 | 5 | 5 |
| GCP-2 | 8 | 8 | 9 | 8 | 13 | 16 | 7 |
| GDNF | 10 | 11 | 12 | 12 | 9 | 10 | 11 |
| GM-CSF | 63 | 52 | 58 | 50 | 52 | 51 | 60 |
| I-309 | 5 | 7 | 9 | 6 | 6 | 5 | 7 |
| IFN-gamma | 96 | 77 | 72 | 71 | 89 | 80 | 79 |
| IGFBP-1 | 7 | 19 | 21 | 25 | 9 | 7 | 10 |
| IGFBP-2 | 10 | 274 | 432 | 490 | 257 | 602 | 442 |
| IGFBP-4 | 9 | 11 | 10 | 8 | 7 | 6 | 4 |
| IGF-I | 9 | 13 | 13 | 14 | 13 | 14 | 16 |
| IL-10 | 59 | 59 | 54 | 43 | 57 | 60 | 66 |
| IL-13 | 81 | 77 | 66 | 62 | 70 | 69 | 75 |
| IL-15 | 56 | 55 | 62 | 46 | 58 | 57 | 55 |
| IL-16 | 3 | 3 | 1 | 6 | 3 | 3 | 4 |
| IL-1alpha | 77 | 76 | 63 | 72 | 78 | 77 | 71 |
| IL-1beta | 8 | 12 | 16 | 12 | 8 | 8 | 14 |
| IL-1ra | 65 | 58 | 68 | 58 | 60 | 55 | 59 |
| IL-2 | 54 | 53 | 62 | 51 | 54 | 51 | 190 |
| IL-3 | 56 | 49 | 52 | 50 | 52 | 51 | 177 |
| IL-4 | 7 | 6 | 7 | 7 | 6 | 6 | 10 |
| IL-5 | 81 | 79 | 82 | 67 | 87 | 76 | 80 |
| IL-6 | 309 | 429 | 280 | 1,053 | 386 | 2,704 | 377 |
| IL-7 | 64 | 56 | 62 | 59 | 63 | 57 | 63 |
| Leptin | 15 | 19 | 14 | 17 | 15 | 23 | 17 |
| LIGHT | 8 | 12 | 10 | 5 | 11 | 7 | 8 |

TABLE 10-continued

| G6 | Nut (−) | Day 4 | Day 14 | TW Apical | TW Basal | QC3 | QC4 |
|---|---|---|---|---|---|---|---|
| MCP-1 | 67 | 3,046 | 1,460 | 4,269 | 3,963 | 5,061 | 2,876 |
| MCP-2 | 16 | 19 | 22 | 22 | 22 | 21 | 21 |
| MCP-3 | 8 | 10 | 10 | 9 | 8 | 62 | 8 |
| MCP-4 | 9 | 11 | 10 | 7 | 8 | 11 | 7 |
| M-CSF | 19 | 18 | 13 | 14 | 17 | 21 | 19 |
| MDC | 9 | 8 | 8 | 7 | 7 | 8 | 7 |
| MIG | 34 | 28 | 31 | 29 | 31 | 29 | 52 |
| MIP-1-delta | 8 | 8 | 8 | 6 | 6 | 6 | 0 |
| MIP-3-alpha | 8 | 8 | 8 | 7 | 7 | 33 | 72 |
| NAP-2 | 7 | 11 | 12 | 8 | 7 | 6 | 10 |
| NT-3 | 12 | 11 | 10 | 12 | 12 | 11 | 9 |
| PARC | 60 | 60 | 56 | 53 | 60 | 57 | 57 |
| PDGF-BB | 13 | 17 | 20 | 15 | 20 | 23 | 21 |
| RANTES | 6 | 63 | 15 | 8 | 13 | 35 | 11 |
| SCF | 5 | 14 | 4 | 3 | 11 | 17 | 6 |
| SDF-1 | 20 | 25 | 26 | 20 | 22 | 22 | 22 |
| TARC | 11 | 14 | 12 | 12 | 12 | 12 | 10 |
| TGF-beta 1 | 82 | 79 | 83 | 81 | 75 | 85 | 77 |
| TGF-beta 3 | 6 | 11 | 5 | 6 | 4 | 8 | 4 |
| TNF-alpha | 86 | 89 | 84 | 78 | 81 | 86 | 81 |
| TNF-beta | 82 | 78 | 84 | 80 | 86 | 83 | 77 |

RPE secreted proteins can be divided into 3 functional groups: 1) Angiogenic proteins such as VEGF and Angiogenin, 2) Extracellular matrix regulators such as TIMP-1 and TIMP-2, and 3) Immunomodulatory proteins such as TL-6, MIF, sgp130, sTNF-R1, sTRAIL-R3, MCP-1, and Osteoprotegerin. The receptor tyrosine kinase Ax1 was also found to be secreted by the RPE cells. 6 proteins that demonstrated high levels of secretion and/or demonstrated a polarized secretion (apical/basal) pattern were selected for validation by ELISA (angiogenin, MIF, sgp130, sTNF-R1 and sTRAIL-R3). The array data also demonstrated secretion of VEGF as seen in the polarization assay.

Figure 32B:
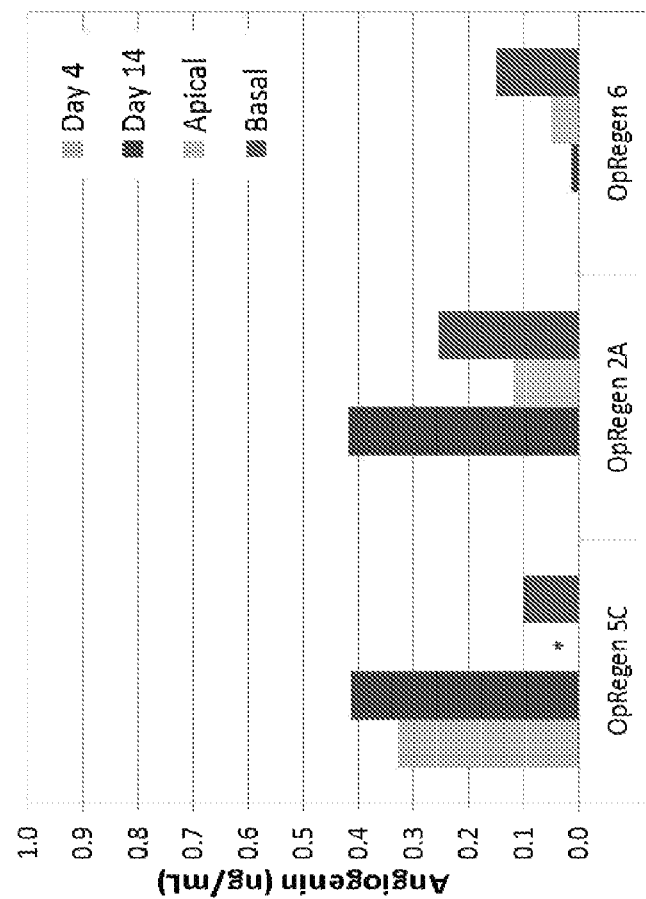
Figure 32A:
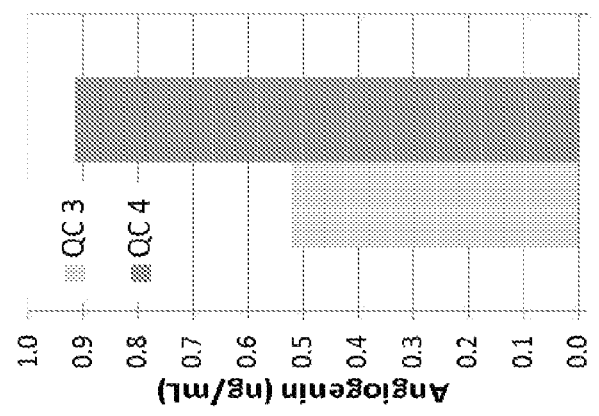

Angiogenin: Protein array data demonstrated increased secretion of angiogenin along the production process (Tables 9 and 10). These results were confirmed by ELISA demonstrating that the level of angiogenin secreted by differentiating cells that were treated with nicotinamide prior to the addition of Activin A was 0.52 ng/mL, whereas after the 2 weeks treatment with nicotinamide and Activin A, agiogenin secretion level increased to 0.91 ng/mL (FIG. 32A). RPE cells which were cultured for 2 weeks in a 12 well plate (0.5×10⁶ cells/well; Passage 3) post thawing secreted angiogenin (FIG. 32B). Polarized RPE cells (week 3 on transwell; TEER>350Ω, PEDF apical/basal and VEGF basal/apical ratios >1) secreted angiogenin in a polarized manner to the basal side with low to no secretion to the apical side (basal angiogenin levels were in the range of 0.1-0.25 ng/mL and apical angiogenin levels in the range of 0.05-0.12 ng/mL; FIG. 32B). RPE7 cells generated according to Idelson et al., 2009 were unable to generate barrier function in the transwell system (TEER below 100Ω) although could secrete VEGF and PEDF. The ability of RPE7 cells to secrete angiogenin was tested when plated in a 12 well plate for 14 days. RPE7 secreted angiogenin on day 14 of culture in a level that is within the range of the RPE cells generated as described herein (FIG. 32C).

Figure 33A:
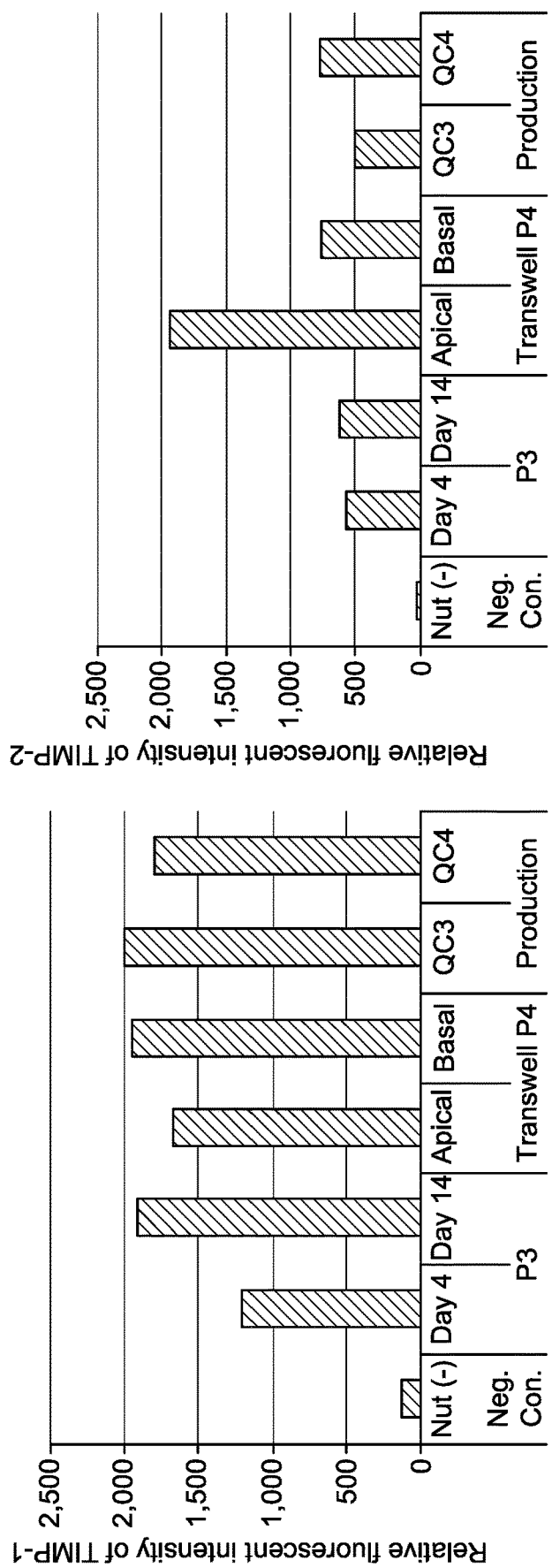
FIGS. 33A-E illustrate TIMP-1 and TIMP-2 Secretion by OpRegen® cells. A. Relative TIMP-1 and TIMP-2 protein levels detected by protein array. B. ELISA TIMP-2 levels in Mock V production QC points 3 and 4. C-D. ELISA TIMP-2 secretion levels by different batches of OpRegen® cells (Passage 3) and on a transwell for 3 weeks during which apical and basal secretion was assessed (Passage 4). E. TIMP-2 levels secreted from RPE7 and HuRPE control cells (Passage 3, Days 4 & 14).
Figure 33C:
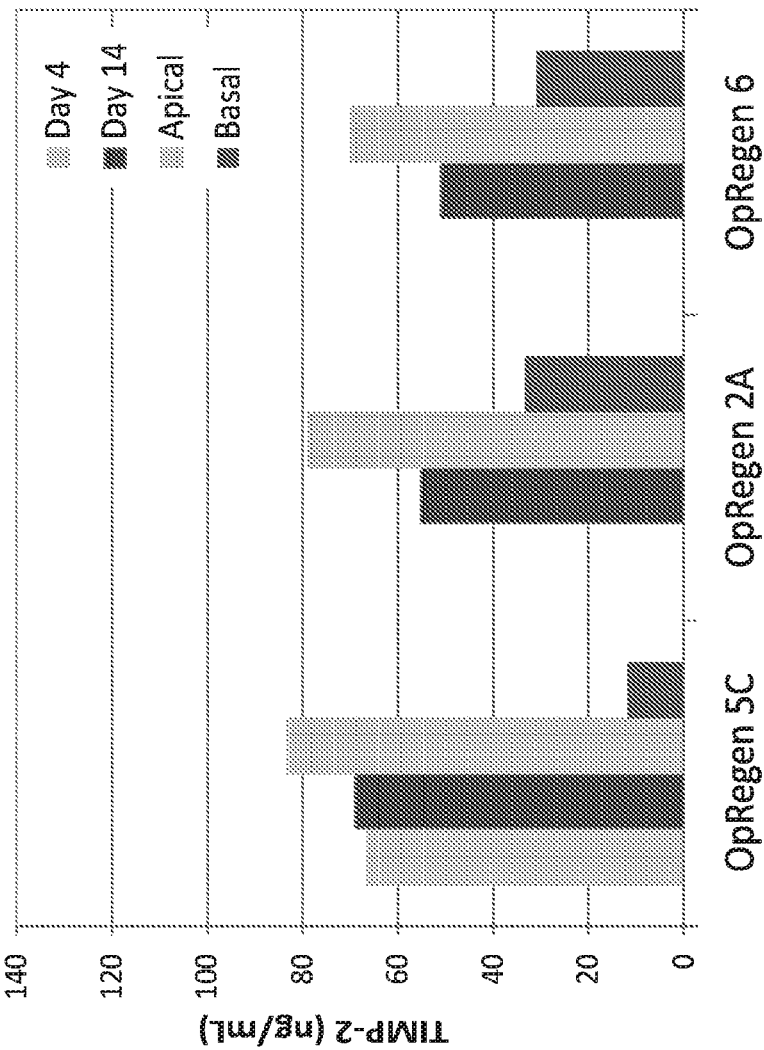
Figure 33B:
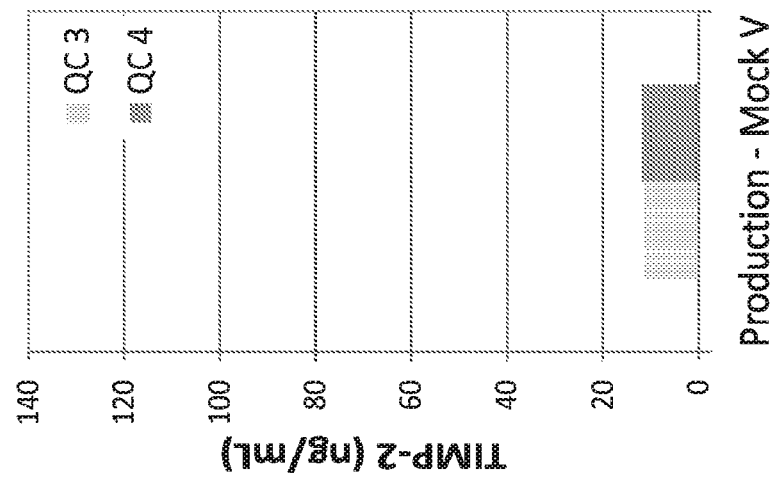
Figure 33E:
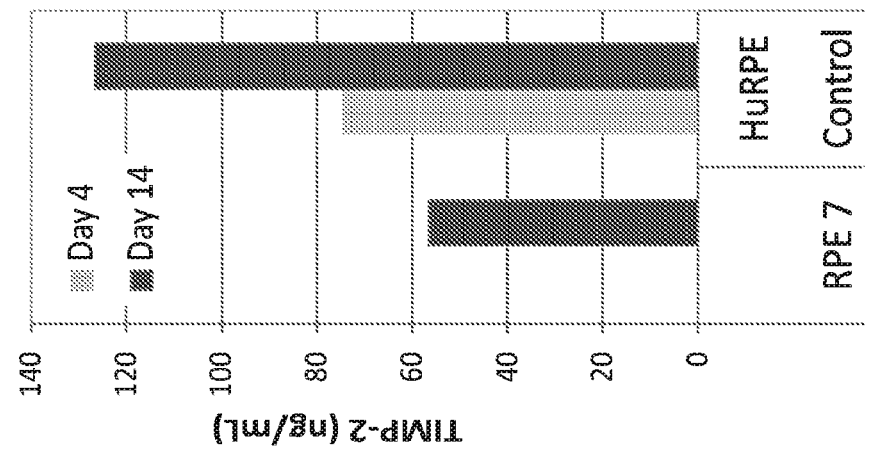
Figure 33D:
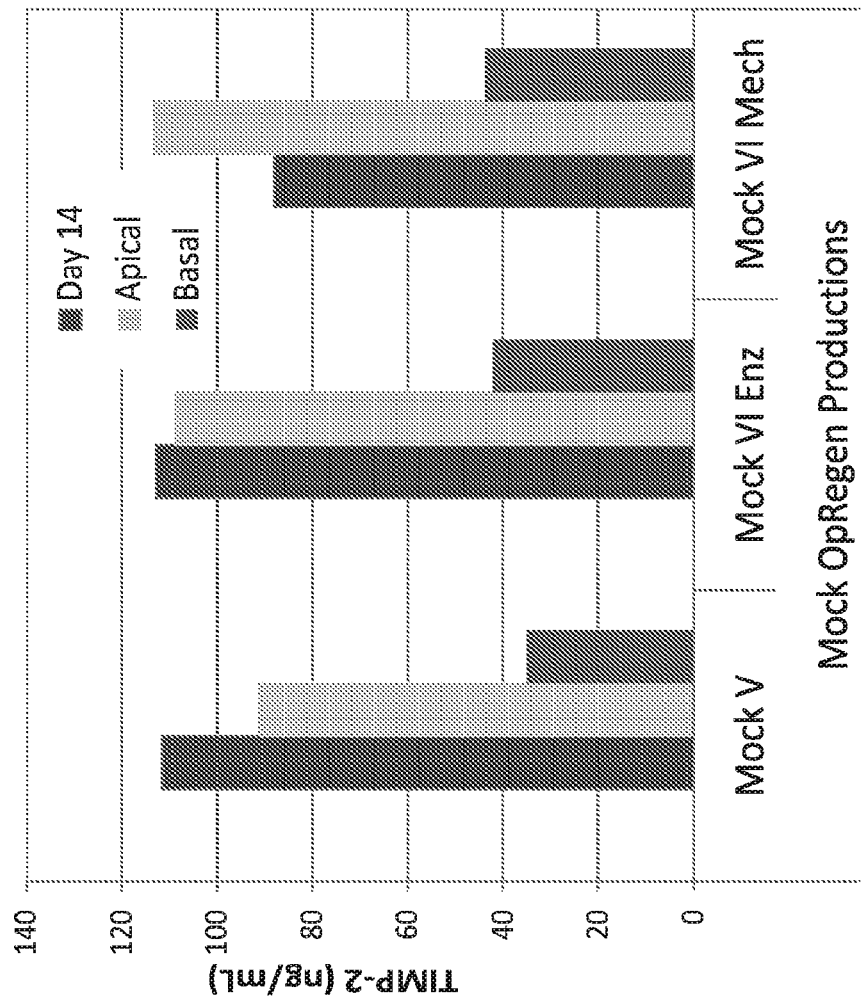

TIMP-1 and TIMP-2 Secretion: Protein array screen demonstrated secretion of TIMP-1 and TIMP-2 from polarized and non-polarized RPE cells (FIG. 33A-E). Interestingly, the array data showed polarized secretion of TIMP-2 to the apical side and TIMP-1 to the basal side (FIG. 33A). ELISA data confirmed that TIMP-2 is secreted mainly to the apical side by all RPE batches tested so far (FIGS. 33C-D apical range of 69.9-113.3 ng/mL and basal range of 11.9-43.7 ng/mL). TIMP-2 was also secreted by non-polarized OpRegen® cells in levels similar to the levels secreted by normal human fetal RPE cells (HuRPE, ScienCell) (FIGS. 33C-E). RPE7 cells also secreted TIMP-2 in levels similar to the OpRegen® cells (FIGS. 33C-E). Interestingly, very low levels of TIMP-2 were detected along the production process at QC3 and QC4 checkpoints (FIG. 33B).

Figure 34B:
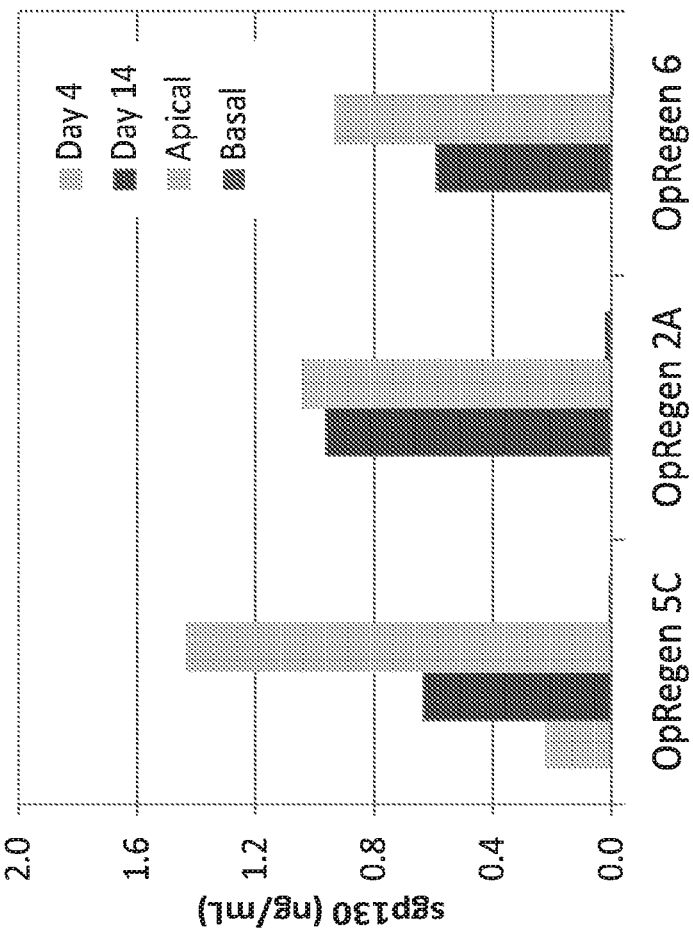
FIGS. 34A-D illustrate sgp130 Secretion by OpRegen® Cells as measured by ELISA. A. sgp130 secretion levels in Mock V production QC points 3 and 4. B-C. Levels of secreted sgp130 by various batches of OpRegen® cells (Passage 3) and on a transwell for 3 weeks during which apical and basal secretion was assessed (Passage 4). D. sgp130 levels secreted from RPE7 and HuRPE control cells (Passage 3, Days 4 & 14).
Figure 34A:
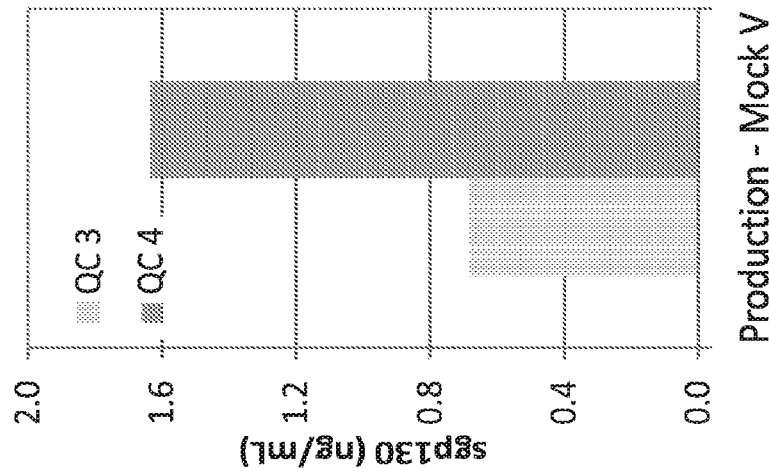
Figure 34D:
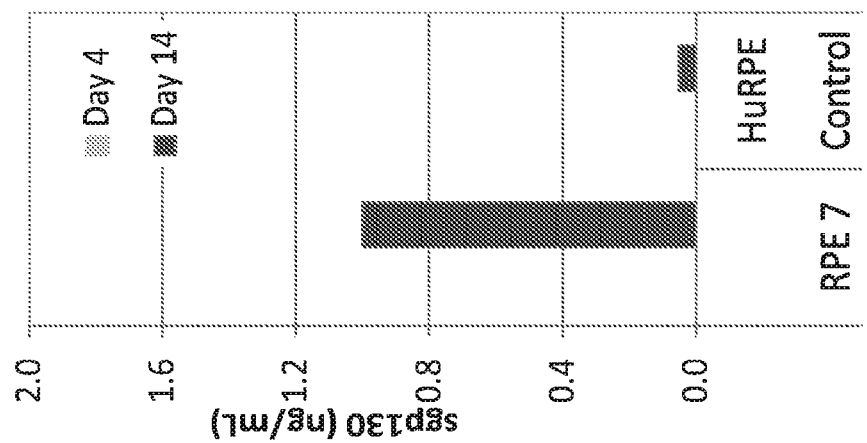
Figure 34C:
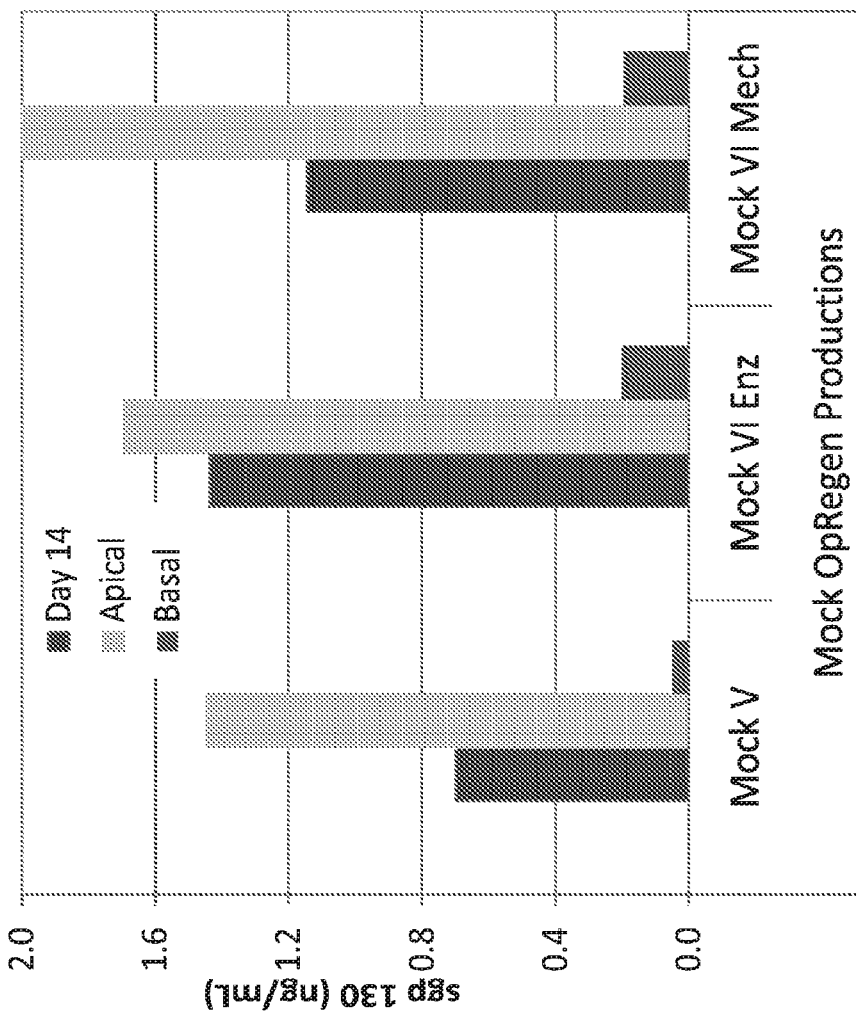

Sgp130 Secretion by OpRegen® Cells: Protein array data demonstrated increased secretion of sgp130 along OpRegen® production process as seen in the IPC/QC check points 3 and 4 (Tables 9 and 10). ELISA data confirmed higher levels of sgp130 secretion following 2 weeks Activin A treatment (IPC/QC4; 1.64 ng/mL) as compared to the levels secreted by the cells following nicotinamide treatment prior to the addition of Activin A (IPC/QC3; 0.68 ng/mL) (FIG. 34A). OpRegen® cells which were cultured for 2 weeks in a 12 well plate (0.5×10⁶ cells/well; Passage 3) post thawing secreted sgp130 (FIGS. 34B-C). RPE7 cells cultured under similar conditions secreted sgp130 in levels that were within the range of OpRegen® cells (1.0 ng/mL at day 14; FIG. 34D). Fetal HuRPE cells secreted low sgp130 levels both on day 4 and on day 14.

Polarized OpRegen® cells secreted sgp130 in a polarized manner to the apical side with low to no secretion to the basal side (apical sgp130 secretion levels were between 0.93-2.06 ng/mL and basal sgp130 levels were in the range of 0-0.2 ng/mL; FIGS. 34B-C).

Figure 35B:
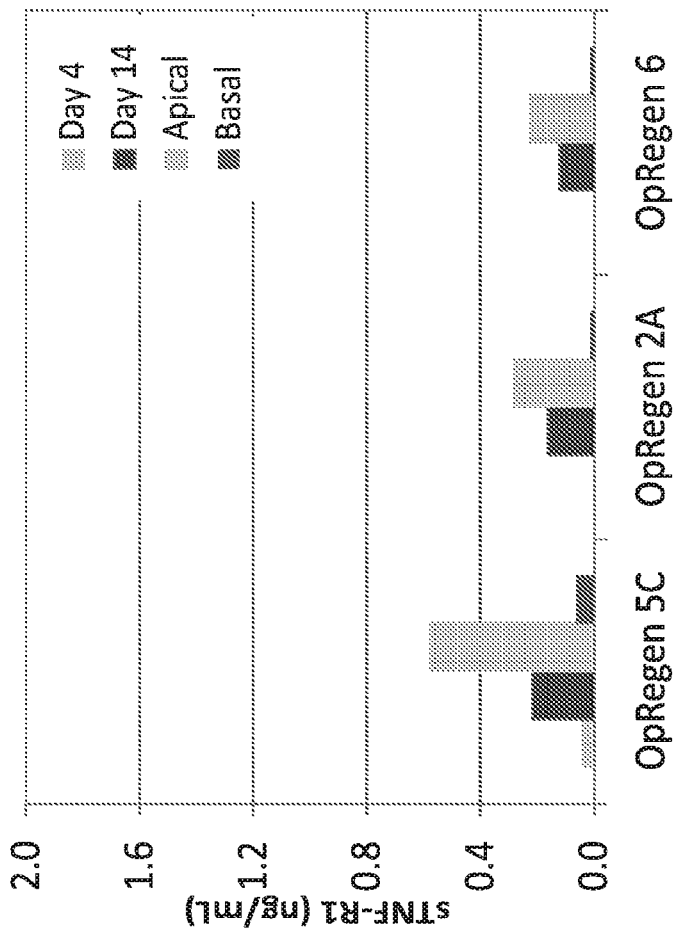
FIGS. 35A-D illustrate sTNF-R1 protein levels in OpRegen® cell supernatant as measured by ELISA. A. sTNF-R1 levels in cell supernatant from Mock V production QC points 3 and 4. B-C. Levels of sTNF-R1 in the supernatant of OpRegen® batches (Passage 3) and on a transwell for 3 weeks during which apical and basal levels were assessed (Passage 4). D. sTNF-R1 levels in day 4 and day 14 RPE7 and control HuRPE cell cultures (Passage 3).
Figure 35A:
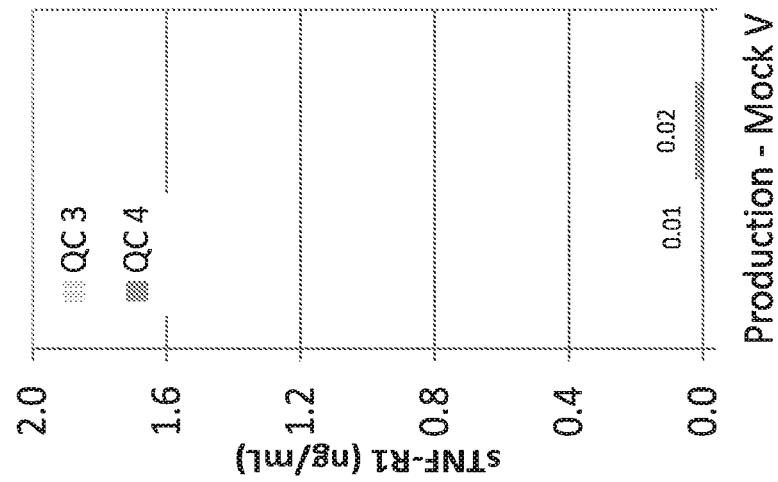
Figure 35D:
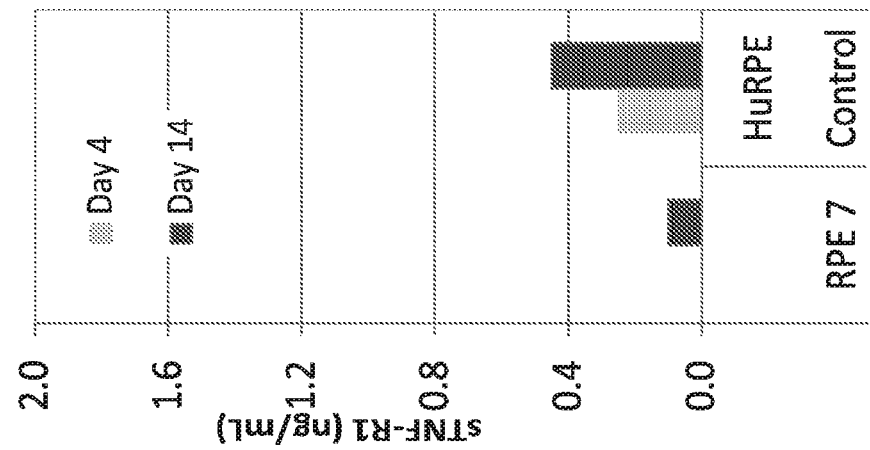
Figure 35C:
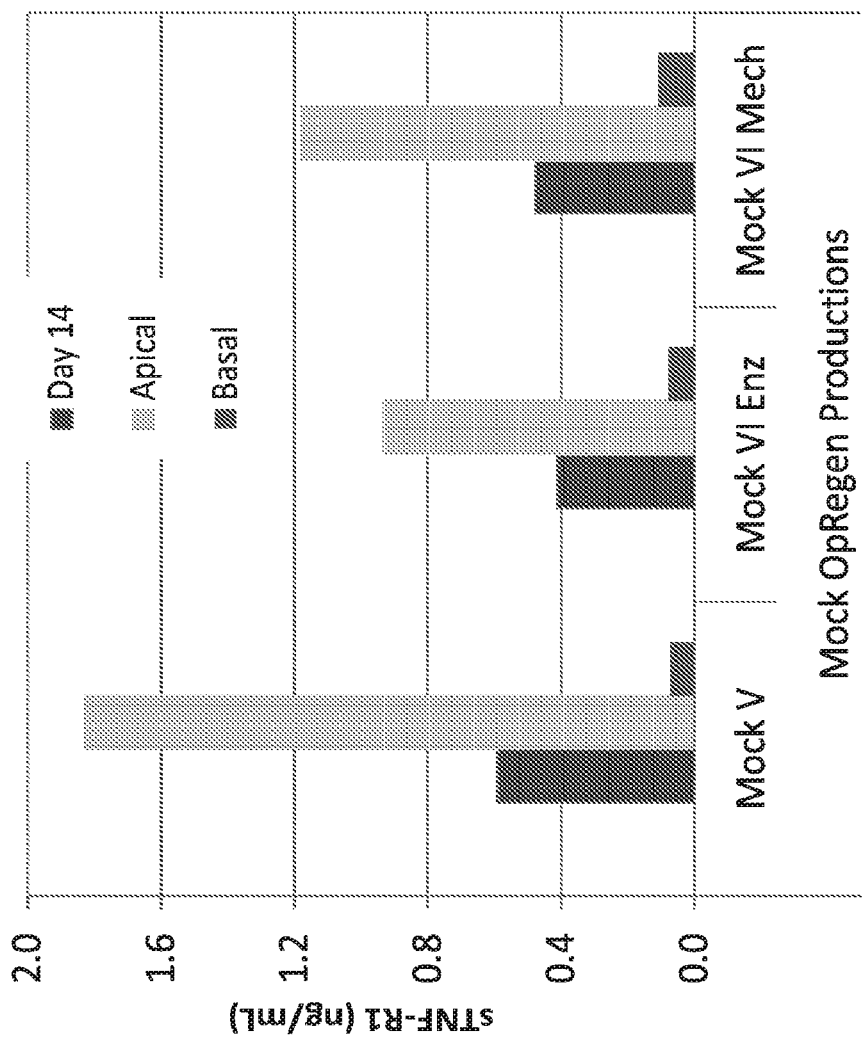

Shed sTNF-R1: Very low levels of shed sTNF-R1 were detected by ELISA in the supernatant of differentiating cells prior (IPC/QC3 0.01 ng/mL) and post two weeks treatment with nicotinamide and Activin A (IPC/QC4 0.02 ng/mL) (FIG. 35A). OpRegen® cells which were cultured for 2 weeks in a 12 well plate (0.5×10⁶ cells/well; Passage 3) post thawing contained sTNF-R1 in the supernatant of culture day 14 (FIGS. 35B-C). HuRPE cells cultured under similar conditions had similar levels of sTNF-R1 in their culture supernatant while RPE7 cells demonstrated relatively low sTNF-R1 levels (FIG. 35D).

Polarized OpRegen® cells secreted shed sTNF-R1 in higher levels to the apical side (apical and basal sTNF-R1 levels were in the range of 0.22-1.83 ng/mL and 0.01-0.11 ng/mL, respectively; FIGS. 35C-D).

sTRAIL-R3: Protein array data detected sTRAIL-R3 in the supernatant of OpRegen® cells (Tables 9 and 10). ELISA confirmed the presence of sTRAIL-R3 along OpRegen® production process (493 pg/mL in QC3 and 238 pg/mL in QC4). In fetal HuRPE culture there was no sTRAIL-R3 and in RPE7 culture, very low levels of sTRAIL-R3 (4 pg/mL).

Detection of MIF: Protein array data detected MIF in the supernatant of OpRegen® cells (Tables 9 and 10). ELISA confirmed the presence of MIF along OpRegen® production process (100.3 ng/mL in QC3 and 44.7 ng/mL in QC4). Polarized OpRegen® cells demonstrated higher levels of MIF in the apical side (apical MIF levels in the range of 26.6-138.3 ng/mL and basal in the range of 1.9-30.5 ng/mL).

Example 10

Comparison of OpRegen® to RPE1 & RPE7

Objective: To compare OpRegen® (RPE cells) with RPE cells generated according to the protocol of Idelson et al, 2009.

Materials and Methods

OpRegen® (RPE cells) were generated as described in Example 3.

RPE cells were generated according to the protocol of Idelson et al, 2009 and named RPE1 and RPE7.

A transwell system (as illustrated in FIG. 28) was used to enable the development of a polarized RPE monolayer with stable barrier properties and polarized PEDF and VEGF secretion. Transepithelial electrical resistance (TEER) measurements were used to assess the barrier function of the RPE monolayer, and Enzyme-Linked Immunosorbent Assay (ELISA) was used to assess polarized PEDF and VEGF secretion. Cells were thawed and cultured for 14 days in the presence of Nicotinamide. PEDF secretion was tested on days 7 and 14. Then cells were transferred to a transwell (Costar 3460, 0.4 μm) for additional 4 weeks during which TEER was measured and medium was collected (for assessment of cytokine secretion) from the upper and lower transwell chambers on a weekly basis up to 4 weeks. When the cells are polarized, TEER should be above 100Ω and the ratio between the apical to basal PEDF secretion and the basal to apical VEGF secretion should be above 1.

All OpRegen® batches that were tested demonstrated the ability to generate barrier function (TEER range of 368-688Ω) and secrete PEDF and VEGF in a polarized manner (Apical/Basal PEDF ratio ranged from 3.47-8.75 and Basal/Apical VEGF ratio of 1.39-2.74) (see Table 11).

TABLE 11

| | Test | Test Method | Criteria for release | OpRegen ® Clinical-Grade Batches | | | OpRegen ® GMP Produced Research-Grade Batches | | | |
|---|---|---|---|---|---|---|---|---|---|---|
| | | | | 2A | 2B | 6 | 5A | 5B | 5C | 5D |
| | RPE Purity % CRLBP⁺PMEL17⁺ | AM-RPE-04 | ≥95% | 98.85% | 98.26% | 99.08 | 98.91% | 99.01% | 99.24% | 99.29% |
| Potency | Polarization-TERR at Week 3 | AM-RPE-15 | For information only | 532 Ω | 458 Ω | 411 Ω | 451 Ω | 468 Ω | 368 Ω | 543 Ω |
| | PEDF Apical/Basal Ratio at Week 3 | | | 8.75 | 6.12 | 5.77 | 3.47 | 4.46 | 3.86 | 4.16 |
| | VEGF Basal/Apical Ratio at Week 3 | | | 2.27 | 2.35 | 2.51 | 1.86 | 1.39 | 1.86 | 1.97 |
| | PEDF secretion day 14 (ng/ml/day) | | | 3033 | 2158 | 2881 | 1562 | 1255 | 1551 | 1370 |

| | Test | Test Method | Criteria for release | Non-GMP Mock Production OpRegen ® Batches | | GMP Produced RPE According to Idelson et al., 2009 | |
|---|---|---|---|---|---|---|---|
| | | | | #4 | #5 | RPE1 | RPE7 |
| | RPE Purity % CRLBP⁺PMEL17⁺ | AM-RPE-04 | ≥95% | 99.61% | 99.76% | 99.91% | 96.29% |
| Potency | Polarization-TERR at Week 3 | AM-RPE-15 | For information only | 688 Ω | 616 Ω | <100 Ω | <100 Ω |
| | PEDF Apical/Basal Ratio at Week 3 | | | 6.78 | 3.93 | ND | ND |
| | VEGF Basal/Apical Ratio at Week 3 | | | 2.57 | 2.74 | ND | ND |
| | PEDF secretion day 14 (ng/ml/day) | | | 2462 | 3936 | 2279 | 2556 |

Figure 36:
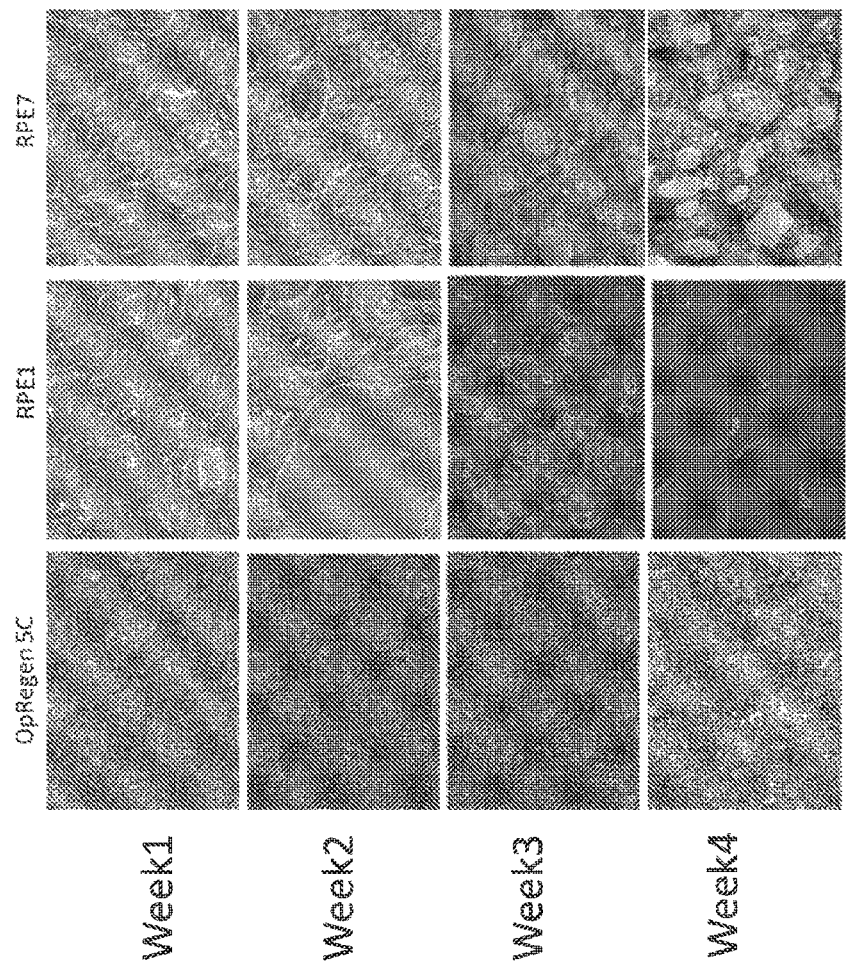
FIG. 36 illustrates the morphology of OpRegen® 5C (Reference Line), RPE1 and RPE7 on Transwell. OpRegen® 5C, RPE1 and RPE7 were imaged weekly (week 1-4) following their seeding on transwell. OpRegen® 5C generated a homogeneous polygonal monolayer from week 1 while RPE1 and RPE7 generated a different non-homogeneous morphology one week post seeding and holes started to appear at week 2. RPE1 cells detached from the transwell after 3 weeks in culture.
Figure 37:
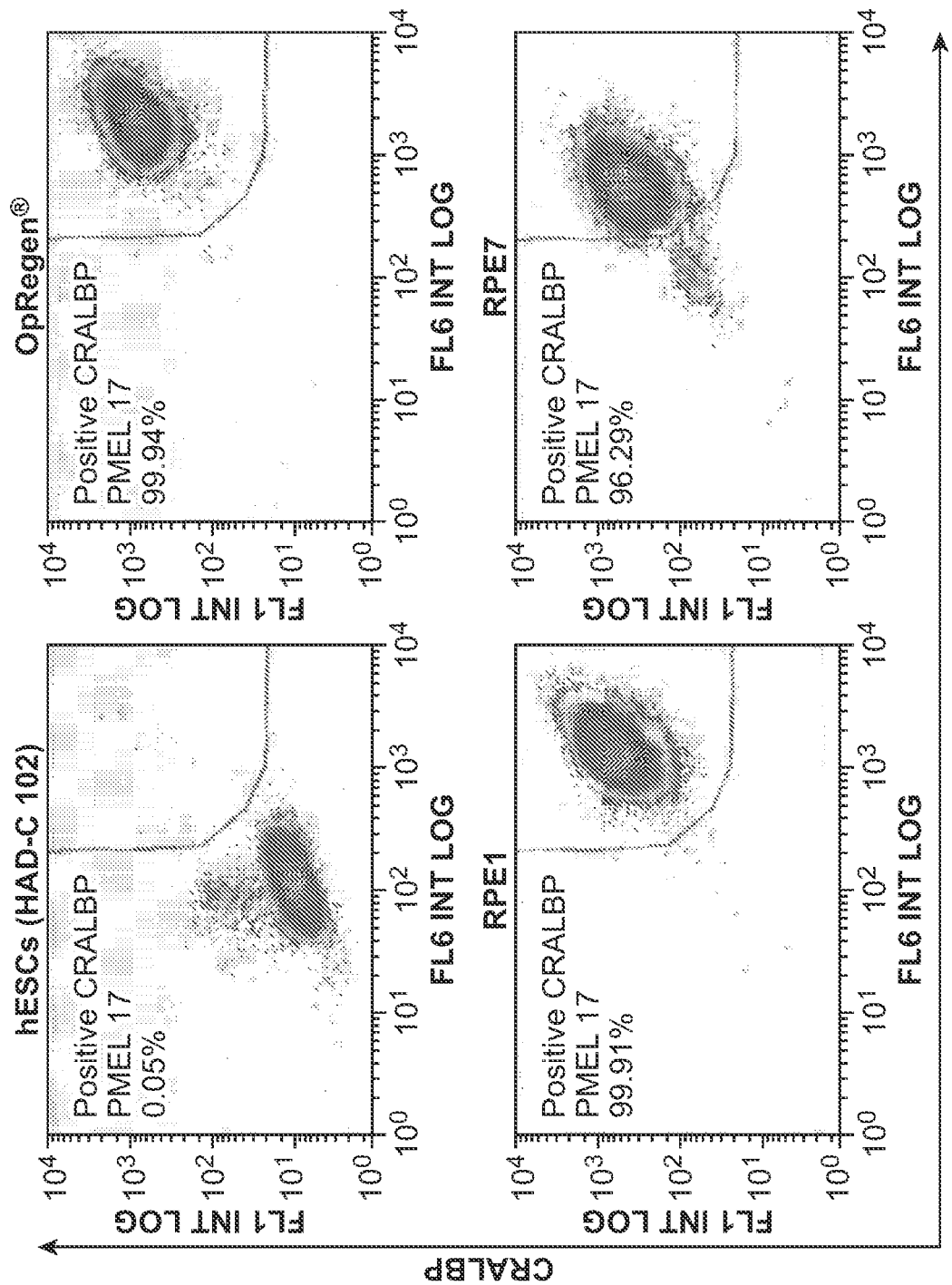
FIG. 37 illustrates that RPE1 and RPE7 cells co-express CRALBP and PMEL-17. FACS Purity assay demonstrated that 99.91% and 96.29% of RPE1 and RPE7 cells, respectively, are double positive for the RPE markers CRALBP and PMEL-17, similar to the levels seen in OpRegen® Mock V cells (Positive Control). HAD-C102 hESCs were used as the negative control.

ND: Not determined since TEER was below 100 Ω and big holes were seen in the culture RPE1 and RP7, that were produced under GMP conditions according to Idelson et al (2009) were unable to generate barrier function (TEER<100Ω) in 3 independent studies. Cells seeded on the transwell were unable to generate a homogeneous closed polygonal monolayer and big holes were seen (FIG. 36). Although the cells could not generate barrier function, RPE1 and RPE7 could secrete PEDF (see Table 11) and VEGF (not shown) in levels similar to OpRegen® and their level of CRALBP+PMEL17+ purity was 99.91% and 96.29%, respectively, similar to OpRegen® (FIG. 37).

Based on these data, it may be concluded that RPE1 and RPE7 are defective in their ability to generate tight junction.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A method of generating retinal pigment epithelium (RPE) cells, comprising:
    (a) culturing human pluripotent stem cells for about 1 week to about 3 weeks in a medium comprising nicotinamide so as to generate differentiating cells, wherein said medium is devoid of Activin A;
    (b) further culturing said differentiating cells for about 1 week to about 4 weeks in a medium comprising Activin A and nicotinamide to generate cells which are further differentiated towards an RPE lineage;
    (c) further culturing said cells which are further differentiated towards the RPE lineage for up to 4 weeks in a medium comprising nicotinamide so as to generate RPE cells, wherein said medium is devoid of Activin A, wherein steps (a)-(c) are effected under conditions wherein the atmospheric oxygen level is less than about 10%, wherein at least 80% of the RPE cells co-express premelanosome protein (PMEL17) and cellular retinaldehyde binding protein (CRALBP) after step (c); and
    (d) expanding said RPE cells.

2. The method of claim 1, wherein at least 95% of the RPE cells co-express PMEL17 and CRALBP after step (c).

3. The method of claim 1, wherein said RPE cells are expanded in step (d) in suspension.

4. The method of claim 1, wherein the expanding of said RPE cells in step (d) is effected on an extracellular matrix.

5. The method of claim 1, wherein the culturing of step (a) comprises:
    i) culturing said population of human pluripotent stem cells in a medium comprising nicotinamide, in the absence of activin A, under non-adherent conditions to generate a cluster of cells comprising differentiating cells; and subsequently
    ii) culturing said differentiating cells of (i) in a medium comprising nicotinamide, in the absence of activin A under adherent conditions.

6. The method of claim 1, further comprising culturing said differentiated cells in a medium under conditions wherein the atmospheric oxygen level is greater than about 10% in the presence of a differentiating agent following step (c).

7. The method of claim 1, further comprising selecting polygonal cells following step (c).

8. The method of claim 1, wherein said human pluripotent stem cells comprise embryonic stem cells.

9. The method of claim 8, wherein said embryonic stem cells are propagated in a medium comprising bFGF and TGFβ prior to step (a).

10. The method of claim 1, wherein steps (a)-(c) are effected under conditions wherein the atmospheric oxygen level is about 5%.

11. The method of claim 1, wherein the differentiating cells are cultured in the medium comprising Activin A and nicotinamide in step (b) for about 1 week to about four weeks.

12. The method of claim 1, wherein the cells which are further differentiated towards the RPE lineage are cultured in a medium comprising nicotinamide and devoid of activin A in step (c) for up to 4 weeks.

13. The method of claim 1, wherein at least 80% of the RPE cells co-express PMEL17 and CRALBP after step (d).

14. The method of claim 13, wherein at least 95% of the RPE cells co-express PMEL17 and CRALBP after step (d).

15. The method of claim 1, wherein said RPE cells are expanded in step (d) in a monolayer.

* * * * *